(12) United States Patent
Lubisch et al.

(10) Patent No.: US 9,487,505 B2
(45) Date of Patent: *Nov. 8, 2016

(54) HETEROARYL-SUBSTITUTED 1,3-DIHYDROINDOL-2-ONE DERIVATIVES AND MEDICAMENTS CONTAINING THEM

(71) Applicants: ABBVIE DEUTSCHLAND GMBH & CO. KG, Wiesbaden (DE); Andrea Hager-Wernet, Neustadt an der Weinstrasse (DE)

(72) Inventors: Wilfried Lubisch, Heidelberg (DE); Wilfried Hornberger, Neustadt (DE); Thorsten K. Oost, Heidelberg (DE); Daryl Richard Sauer, Trevor, WI (US); Liliane Unger, Ludwigshafen (DE); Wolfgang Wernet, Neustadt (DE); Hervé Geneste, Ludwigshafen (DE)

(73) Assignees: ABBVIE DEUTSCHLAND GMBH & CO. KG, Wiesbaden (DE); Andrea Hager-Wernet, Neustadt an der Weinstrasse (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/037,026

(22) Filed: Sep. 25, 2013

(65) Prior Publication Data
US 2014/0187543 A1 Jul. 3, 2014

Related U.S. Application Data

(60) Division of application No. 12/839,595, filed on Jul. 20, 2010, now Pat. No. 8,580,842, which is a division of application No. 10/574,211, filed as application No. PCT/EP2004/010940 on Sep. 30, 2004, now Pat. No. 7,902,379, which is a continuation-in-part of application No. 10/675,300, filed on Sep. 30, 2003, now abandoned.

(51) Int. Cl.
| | |
|---|---|
| *A01N 43/38* | (2006.01) |
| *C07D 403/14* | (2006.01) |
| *C07D 401/04* | (2006.01) |
| *C07D 403/04* | (2006.01) |
| *C07D 403/12* | (2006.01) |
| *C07D 405/14* | (2006.01) |
| *C07D 409/04* | (2006.01) |
| *C07D 401/14* | (2006.01) |
| *C07D 413/14* | (2006.01) |
| *C07D 417/14* | (2006.01) |

(52) U.S. Cl.
CPC .......... *C07D 403/14* (2013.01); *C07D 401/04* (2013.01); *C07D 401/14* (2013.01); *C07D 403/04* (2013.01); *C07D 403/12* (2013.01); *C07D 405/14* (2013.01); *C07D 409/04* (2013.01); *C07D 413/14* (2013.01); *C07D 417/14* (2013.01)

(58) Field of Classification Search
CPC ..................................................... C07D 403/14
USPC ........................................................ 514/414
See application file for complete search history.

(56) References Cited

U.S. PATENT DOCUMENTS

| | | | |
|---|---|---|---|
| 3,964,896 A | 6/1976 | Brouwer et al. | |
| 4,022,901 A | 5/1977 | Narayanan et al. | |
| 4,122,257 A | 10/1978 | Prossel et al. | |
| 5,594,023 A * | 1/1997 | Wagnon et al. | 514/423 |

(Continued)

FOREIGN PATENT DOCUMENTS

| | | |
|---|---|---|
| CA | 2107348 A1 | 7/1993 |
| CA | 2593044 A1 | 7/2006 |

(Continued)

OTHER PUBLICATIONS

Ryckmans (2010, vol. 13, Issue: 5, pp. 538-547.*

(Continued)

*Primary Examiner* — Nizal Chandrakumar
(74) *Attorney, Agent, or Firm* — Neal Gerber & Eisenberg LLP

(57) ABSTRACT

The present invention relates to novel 1,3-dihydroindol-2-one (oxindole) derivatives of the formula (I)

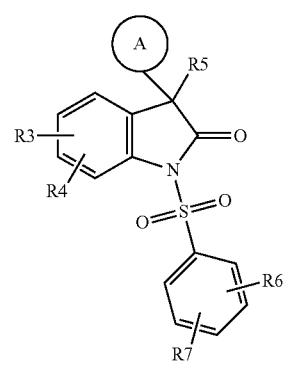

in which
A, $R^3$, $R^4$, $R^5$, $R^6$ and $R^7$ are defined according to claim 1, and to medicaments containing them for the treatment of diseases. In particular, the novel oxindole derivatives can be used for the control and/or prophylaxis of various vasopressin-dependent or oxytocin-dependent diseases.

8 Claims, No Drawings

(56) References Cited

U.S. PATENT DOCUMENTS

| | | | |
|---|---|---|---|
| 5,914,328 A | 6/1999 | Lin et al. | |
| 5,948,793 A | 9/1999 | Abreo et al. | |
| 5,977,144 A | 11/1999 | Meyer et al. | |
| 6,090,818 A | 7/2000 | Foulon et al. | |
| 6,130,217 A | 10/2000 | Arnold et al. | |
| 6,207,863 B1 | 3/2001 | Berrier et al. | |
| 6,538,003 B1 | 3/2003 | Galli et al. | |
| 6,579,880 B2 | 6/2003 | Weidner-Wells et al. | |
| 6,596,732 B2 | 7/2003 | Serradeil-Le-Gal et al. | |
| 6,605,610 B1 | 8/2003 | Coe et al. | |
| 6,624,164 B2 | 9/2003 | Schoentjes et al. | |
| 6,809,105 B2 | 10/2004 | Schrimpf et al. | |
| 6,833,370 B1 | 12/2004 | Schrimpf et al. | |
| 6,864,277 B2 * | 3/2005 | Roux et al. | 514/418 |
| 6,919,359 B2 | 7/2005 | Piotrowski et al. | |
| 7,041,685 B2 | 5/2006 | Cai et al. | |
| 7,119,086 B2 * | 10/2006 | Di Malta et al. | 514/218 |
| 7,902,379 B2 | 3/2011 | Lubisch et al. | |
| 8,017,631 B2 | 9/2011 | Dahl et al. | |
| 8,129,389 B2 | 3/2012 | Lubisch et al. | |
| 8,350,055 B2 | 1/2013 | Oost et al. | |
| 8,546,401 B2 | 10/2013 | Braje et al. | |
| 8,703,774 B2 | 4/2014 | Netz et al. | |
| 8,703,775 B2 | 4/2014 | Oost et al. | |
| 8,815,858 B2 | 8/2014 | Bjornson et al. | |
| 8,859,557 B2 | 10/2014 | Netz et al. | |
| 2003/0109545 A1 | 6/2003 | Serradeil-Le-Gal et al. | |
| 2003/0114683 A1 | 6/2003 | Roux et al. | |
| 2003/0139413 A1 | 7/2003 | Schoentjes et al. | |
| 2003/0162767 A1 | 8/2003 | Roux et al. | |
| 2004/0063601 A1 | 4/2004 | Denome et al. | |
| 2004/0152724 A1 | 8/2004 | Dart et al. | |
| 2004/0180878 A1 | 9/2004 | Di et al. | |
| 2004/0186107 A1 | 9/2004 | Schrimpf et al. | |
| 2004/0204461 A1 | 10/2004 | Karp et al. | |
| 2005/0070718 A1 | 3/2005 | Lubisch et al. | |
| 2006/0019976 A1 | 1/2006 | Karp et al. | |
| 2007/0021465 A1 | 1/2007 | Al-Abed et al. | |
| 2007/0021607 A1 | 1/2007 | Lubisch et al. | |
| 2007/0185126 A1 | 8/2007 | Lubisch et al. | |
| 2008/0167286 A1 | 7/2008 | Gopalakrishnan et al. | |
| 2008/0255203 A1 | 10/2008 | Lee et al. | |
| 2008/0269236 A1 | 10/2008 | Ji et al. | |
| 2008/0318923 A1 | 12/2008 | Sekiguchi et al. | |
| 2009/0005397 A1 | 1/2009 | Lubisch et al. | |
| 2009/0163492 A1 | 6/2009 | Oost et al. | |
| 2009/0215790 A1 | 8/2009 | Lubisch et al. | |
| 2010/0305086 A1 | 12/2010 | Gopalakrishnan et al. | |
| 2011/0077241 A1 | 3/2011 | Lubisch et al. | |
| 2011/0092516 A1 | 4/2011 | Braje et al. | |
| 2011/0124658 A1 | 5/2011 | Netz et al. | |
| 2011/0190314 A1 | 8/2011 | Gopalakrishnan et al. | |
| 2014/0187543 A1 | 7/2014 | Lubisch et al. | |
| 2014/0194440 A1 | 7/2014 | Braje et al. | |
| 2014/0275110 A1 | 9/2014 | Oost et al. | |
| 2014/0315914 A1 | 10/2014 | Netz et al. | |

FOREIGN PATENT DOCUMENTS

| | | | |
|---|---|---|---|
| DE | 10148598 A1 | 10/2002 | |
| EP | 0979814 B1 | 10/2003 | |
| EP | 2226074 A2 | 9/2010 | |
| EP | 2101763 B1 | 7/2012 | |
| EP | 2114921 B1 | 12/2012 | |
| EP | 2546250 A1 | 1/2013 | |
| EP | 2546251 A1 | 1/2013 | |
| EP | 2546252 A1 | 1/2013 | |
| WO | WO-9313083 A1 | 7/1993 | |
| WO | WO-9315051 A1 | 8/1993 | |
| WO | WO-9518105 A1 | 7/1995 | |
| WO | WO-9640682 A1 | 12/1996 | |
| WO | WO-9825901 A1 | 6/1998 | |
| WO | WO-9910338 A2 | 3/1999 | |
| WO | WO-9932480 A1 | 7/1999 | |
| WO | WO-9965876 A1 | 12/1999 | |
| WO | WO-0007600 A1 | 2/2000 | |
| WO | WO-0045799 A2 | 8/2000 | |
| WO | WO-0071534 A1 | 11/2000 | |
| WO | WO-0075110 A1 | 12/2000 | |
| WO | WO-0155130 A2 | 8/2001 | |
| WO | WO-0155134 A2 | 8/2001 | |
| WO | WO-0162736 A1 | 8/2001 | |
| WO | WO-0164668 A2 | 9/2001 | |
| WO | WO-0181334 A2 | 11/2001 | |
| WO | WO-0181347 A2 | 11/2001 | |
| WO | WO-0187295 A1 | 11/2001 | |
| WO | WO-0198295 A1 | 12/2001 | |
| WO | WO-02068417 A2 | 9/2002 | |
| WO | WO-02100826 A2 | 12/2002 | |
| WO | WO-03008407 A2 | 1/2003 | |
| WO | WO-2004018607 A2 | 3/2004 | |
| WO | WO-2005030755 A1 | 4/2005 | |
| WO | WO-2006005609 A2 | 1/2006 | |
| WO | WO-2006047392 A2 | 5/2006 | |
| WO | WO-2006071184 A1 | 7/2006 | |
| WO | WO-2006072458 A2 | 7/2006 | |
| WO | WO-2006086068 A1 | 8/2006 | |
| WO | WO-2006096358 A1 | 9/2006 | |
| WO | WO-2006100080 A1 | 9/2006 | |
| WO | WO-2006100081 A2 | 9/2006 | |
| WO | WO-2006100082 A2 | 9/2006 | |
| WO | WO-2006114400 A1 | 11/2006 | |
| WO | 2007084535 A2 | 7/2007 | |
| WO | WO-2007149395 A2 | 12/2007 | |
| WO | WO-2008028903 A2 | 3/2008 | |
| WO | WO-2008073942 A2 | 6/2008 | |
| WO | WO-2008080970 A1 | 7/2008 | |
| WO | WO-2008080971 A1 | 7/2008 | |
| WO | WO-2008080972 A1 | 7/2008 | |
| WO | WO-2008080973 A1 | 7/2008 | |
| WO | 2009071687 A1 | 6/2009 | |
| WO | 2009071689 A2 | 6/2009 | |
| WO | 2009071690 A2 | 6/2009 | |
| WO | WO-2009148452 A1 | 12/2009 | |
| WO | 2010009775 A1 | 1/2010 | |
| WO | WO-2010138600 A2 | 12/2010 | |
| WO | WO-2010148598 A1 | 12/2010 | |

OTHER PUBLICATIONS

Itoh et al Am. J. Physiol. Endocrinol. Metab, 291, E147-151, 2006.*
Griebel et al. Proc. Natl. Acad. Sci., 2002, 99(9), 6370-7375.*
Venkatesh J. Pharm. Sci. 89, 145-54 (2000).*
Bourdeau et al. Current Opinion in Endocrinology & Diabetes (2002), 9(3), 230-236.*
Final Office Action mailed Nov. 22, 2013 for U.S. Appl. No. 12/746,707, filed Dec. 7, 2010.
Notice of Allowance mailed Dec. 6, 2013 for U.S. Appl. No. 12/521,713, filed Sep. 7, 2010.
Notice of Allowance mailed Nov. 25, 2013 for U.S. Appl. No. 12/746,688, filed Nov. 29, 2010.
Notice of Allowance mailed Nov. 27, 2013 for U.S. Appl. No. 12/746,700, filed Nov. 29, 2010.
Non-Final Office Action mailed Jun. 19, 2014 for U.S. Appl. No. 12/746,707, filed Dec. 7, 2010.
Non-Final Office Action mailed May 22, 2014 for U.S. Appl. No. 12/787,937, filed May 26, 2010.
Notice of Allowance and Examiner Initiated Interview Summary mailed Jun. 6, 2014 for U.S. Appl. No. 13/590,261, filed Aug. 21, 2012.
Final Office Action mailed Mar. 6, 2014 for U.S. Appl. No. 13/080,071, filed Apr. 5, 2011.
Notice of Allowance mailed Apr. 11, 2014 for U.S. Appl. No. 12/521,713, filed Sep. 7, 2010.
Banfi L., et al., "Ugi Multicomponent Reaction Followed by an Intermolecular Nucleophilic Substitution: Convergent Multicomponent Synthesis of 1-sulfonyl 1,4-diazepan-5-ones and of their Benzo-Fuzed Derivatives," Journal of Organic Chemistry, 2007, vol. 72 (6), pp. 2151-2160.
Banker G.S. et al., Modern Pharmaceutics, 3rd Edition, Marcel Dekker, 1996, pp. 596.

(56) References Cited

OTHER PUBLICATIONS

Barberis C., et al., "Structural Bases of Vasopressin/oxytocin Receptor Function," Journal of Endocrinology, 1998, vol. 156 (2), pp. 223-239.
Bitner R.S., et al., "Reduced Nicotinic Receptor-Mediated Antinociception Following in Vivo Antisense Knock-Down in Rat ," Brain Research , 2000, vol. 871, pp. 66-74.
Bonte J.P., et al., "6-Acyl Benzoxazolinones (1st memorandum)," European Journal of Medicinal Chemistry, 1974, vol. 9 (5), pp. 491-496.
Brain C.T., et al., "Novel Procedure for the Synthesis of 1,3,4-oxadiazoles from 1,2-diacylhydrazines Using Polymer-Supported Burgess Reagent Under Microwave Conditions," Tetrahedron Letters, 1999, vol. 40, pp. 3275-3278.
Bundgaard, E. et al., "Design of Prodrugs, Elsevier Science Publishers, Amsterdam, Table of Contents," 1986.
Bundgaard H., ed., in: Design of Prodrugs, Elsevier Science, 1985, Table of Contents.
Chaplan S.R., et al., "Quantitative Assessment of Tactile Allodynia in the Rat Paw," Journal of Neuroscience Methods, 1994, vol. 53 (1), pp. 55-63.
Chattopadhyay S.K., et al., "Formation of Medium-Ring Heterocycles by Diene and Enyne Metathesis," Tetrahedron, 2007, vol. 63, pp. 3919-3952.
Cheung B.S., et al., "Etiologic Significance of Arginine Vasopressin in Motion Sickness," Journal of Clinical Pharmacology, 1994, vol. 34 (6), pp. 664-670.
Co-pending U.S. Appl. No. 61/058,735, filed Jun. 4, 2008.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Cucchiaro G., et al., "The Dorsal Raphe Nucleus as a Site of Action of the Antinociceptive and Behavioral Effects of the Alpha4 Nicotinic Receptor Agonist Epibatidine," Journal of Pharmacology and Experimental Therapeutics, 2005, vol. 313 (1), pp. 389-394.
Curtis L., et al., "Potentiation of Human Alpha4beta2 Neuronal Nicotinic Acetylcholine Receptor by Estradiol," Molecular Pharmacology, 2002, vol. 61 (1), pp. 127-135.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Decker M.W., et al., "Nicotinic Acetylcholine Receptor Agonists: a Potential New Class of Analgesics," Current Topics in Medicinal Chemistry, 2004, vol. 4 (3), pp. 369-384.
Decker M.W., et al., "The Therapeutic Potential of Nicotinic Acetylcholine Receptor Agonists for Pain Control," Expert Opinion on Investigational Drugs, 2001, vol. 10 (10), pp. 1819-1830.
Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.
Dorwold F.Z., "Side Reactions in Organic Synthesis," Wiley-VCH, 2005, Preface.
Dunbar G.C., et al., "Effect of Ispronicline, a Neuronal Nicotinic Acetylcholine Receptor Partial Agonist, in Subjects with Age Associated Memory Impairment (AAMI).," Journal of Psychopharmacology, 2007, vol. 21 (2), pp. 171-178.
Emsley R.A., et al., "Vasopressin Secretion and Memory Impairment in Alcoholic Korsakoffs Syndrome," Alcohol and Alcoholism, 1995, vol. 30 (2), pp. 223-229.
Ersek K., et al., "The Cognitive Effects of Opioids," Pain Management Nursing, 2004, vol. 5 (2), pp. 75-93.

Ettmayer P., et al., "Lessons Learned from Marketed and Investigational Prodrugs," Journal Medicinal Chemistry, 2004, vol. 47 (10), pp. 2393-2404.
European Search Report for Application No. EP10163998, mailed on Jan. 28, 2011, 5 pages.
European Search Report for Application No. EP12177640, mailed on Dec. 12, 2012, 2 pages.
European Search Report for Application No. EP12177642, mailed on Dec. 12, 2012, 2 pages.
European Search Report for Application No. EP12177644, mailed on Dec. 12, 2012, 1 page.
Everts H.G., et al., "Differential Modulation of Lateral Septal Vasopressin Receptor Blockade in Spatial Learning, Social Recognition, and Anxiety-Related Behaviors in Rats," Behavioural Brain Research, 1999, vol. 99 (1), pp. 7-16.
Ex Parte Quayle Action mailed Sep. 11, 2008 for U.S. Appl. No. 10/574,211, filed Jan. 22, 2007.
Ex Parte Quayle Action mailed Aug. 21, 2012 for U.S. Appl. No. 12/839,612, filed Jul. 20, 2010.
Ex Parte Quayle Action mailed Aug. 22, 2012 for U.S. Appl. No. 12/134,678, filed Jun. 6, 2008.
Ferreira M., et al., "Brainstem Nicotinic Receptor Subtypes That Influence Intragastric and Arterial Blood Pressures," Journal of Pharmacology and Experimental Therapeutics, 2000, vol. 294 (1), pp. 230-238.
Final Office Action mailed May 10, 2012 for U.S. Appl. No. 12/746,715, filed Dec. 7, 2010.
Final Office Action mailed Feb. 13, 2012 for U.S. Appl. No. 12/746,688, filed Nov. 29, 2010.
Final Office Action mailed Apr. 19, 2013 for U.S. Appl. No. 12/746,707, filed Dec. 7, 2010.
Final Office Action mailed Feb. 24, 2012 for U.S. Appl. No. 12/746,700, filed Nov. 29, 2010.
Final Office Action mailed Mar. 26, 2013 for U.S. Appl. No. 12/746,688, filed Nov. 29, 2010.
Final Office Action mailed Apr. 27, 2012 for U.S. Appl. No. 12/521,713, filed Sep. 7, 2010.
Final Office Action mailed Feb. 27, 2012 for U.S. Appl. No. 12/746,707, filed Dec. 7, 2010.
Final Office Action mailed Sep. 27, 2012 for U.S. Appl. No. 13/080,071, filed Apr. 5, 2011.
Final Office Action mailed Sep. 29, 2011 for U.S. Appl. No. 12/787,937, filed May 26, 2010.
Franklin S. R., et al., "Positive Allosteric Modulation of Alpha $ Beta 2 Nicotinic Receptors Potrntiates Some CNS Effects of the Alpha 4 Beta 2 Agonist, ABT-594," Biochemical Pharmacology, 2009, vol. 78 (7), pp. 921.
Freshney R.I., et al., Culture of Animal Cells, A Manual of Basic Technique, 1983, Wiley & Sons, Inc., pp. 7-9.
Furniss B.S., et al., Vogel's Textbook of Practical Organic Chemistry, 5th Edition, Longman Scientific & Technical, 1989, Table of Contents.
Gopalakrishnan, M. et al., "Ion channels—Ligand gated. Comprehensive Medicinal Chemistry II, Edited by Triggle D.J. et al." Major Reference Works, 2006, Unit 2.22, pp. 877-918, Elsevier.
Grant P.J., et al., "Effects of Physiological Concentrations of Vasopressin on Haemostatic Function in Man," Clinical Science, 1985, vol. 69 (4), pp. 471-476.
Greene T.W., et al., in: Protective Groups in Organic Synthesis, 3rd Edition, John Wiley and Sons, Inc., 1999, Preface, Table of Contents, Abbreviations.
Greene T.W., et al., "Protection for the Amino group," Protective Groups in Organic Synthesis, 1999, Third Edition, pp. 494-653.
Griebel G., et al., "Anxiolytic- and Antidepressant-Like Effects of the Non-Peptide Vasopressin V1b Receptor Antagonist, SSR149415, Suggest an Innovative Approach for the Treatment of Stress-Related Disorders," Proceedings of the National Academy of Sciences, 2002, vol. 99 (9), pp. 6370-6375.
Hays R.M., et al., "Vasopressin Antagonists--Progress and Promise," The New England Journal of Medicine, 2006, vol. 355 (20), pp. 2146-2148.
Higuchi T., et al., eds., Pro-drugs as Novels Delivery Systems, vol. 14, ACS Symposium Series, 1975, Table of Contents.

(56) References Cited

OTHER PUBLICATIONS

Hulme C., et al., "Quaternary Substituted PDE4 Inhibitors I: the Synthesis and in Vitro Evaluation of a Novel Series of Oxindoles," Bioorganic & Medicinal Chemistry Letters, 1998, vol. 8 (2), pp. 175-178.
Humphrey G.R., et al., "A Novel Synthesis of 3-Bromo-1,2,4-oxadiazoles," Journal of Heterocyclic Chemistry, 1989, vol. 26 (1), pp. 23-24.
International Preliminary Report on Patentability and Written Opinion for Application No. PCT/US08/066002, mailed on Dec. 6, 2010, 8 pages.
International Preliminary Report on Patentability and Written Opinion for Application No. PCT/US2007/087090, mailed on Jun. 16, 2009, 11 pages.
International Preliminary Report on Patentability and Written Opinion for Application No. PCT/US2010/036213, mailed on Nov. 29, 2011, 14 pages.
International Search Report for Application No. PCT/EP2008/066931, mailed on May 12, 2009, 6 pages.
International Search Report for Application No. PCT/EP2008/066934, mailed on Jun. 4, 2009, 6 pages.
International Search Report for Application No. PCT/EP2008/066935 (WO2009/071690), mailed on Jun. 4, 2009, 6 pages.
International Search Report for Application No. PCT/US08/066002, mailed on Jan. 20, 2009, 3 pages.
International Search Report for Application No. PCT/US2007/087090, mailed on Oct. 20, 2008, 5 pages.
International Search Report for Application No. PCT/US2007/087091, mailed on May 8, 2008, 3 pages.
International Search Report for Application No. PCT/US2010/036213, mailed on Nov. 24, 2010, 8 pages.
Isobe T., et al., "2-Chloro-1,3-dimethylimidazolinium Chloride. 1. A Powerful Dehydrating Equivalent to DCC," The Journal of Organic Chemistry, 1999, vol. 64, pp. 6984-6988.
Itoh S., et al., "Attenuated Stress-induced Catecholamine Release in Mice Lacking the Vasopressin V1b Receptor," American Journal of Physiology. Endocrinology and Metabolism, 2006, vol. 291 (1), pp. E147-E151.
Japundzic-Zigon N., et al., "Effects of Nonpeptide and Selective V1 and V2 Antagonists on Blood Pressure Short-Term Variability in Spontaneously Hypertensive Rats," Journal of Pharmacological Sciences, 2004, vol. 95 (1), pp. 47-55.
Jonat S., et al., "Effect of DDAVP on Nocturnal Enuresis in a Patient with Nephrogenic Diabetes Insipidus," Archives of Disease in Childhood, 1999, vol. 81 (1), pp. 57-59.
Khan I.M., et al., "Ablation of Primary Afferent Terminals Reduces Nicotinic Receptor Expression and the Nociceptive Responses to Nicotinic Agonists in the Spinal Cord," Journal of Neurocytology, 2004, vol. 33 (5), pp. 543-556.
Khan M.T., et al., "Structure-Activity Relationships of Tyrosinase Inhibitory Combinatorial Library of 2,5-Disubstituted-1,3,4-Oxadiazole Analogues," Bioorganic & Medicinal Chemistry, 2005, vol. 13 (10), pp. 3385-3395.
Kim S.H., et al., "An Experimental Model for Peripheral Neuropathy Produced by Segmental Spinal Nerve Ligation in the Rat," Pain, 1992, vol. 50 (3), pp. 355-363.
Kirrane T., et al., "Effects of Amphetamine on Cognitive Impairment in Schizotypal Personality Disorder," Biological Psychiatry, 1996, vol. 39 (7), pp. 581.
Kocevar M., et al., "Ring Transformations of Some 4-Aminopteridine 3-Oxides and Derivatives," Tetrahedron, 1982, vol. 39 (5), pp. 823-829.
Koch U., et al., "2-(2-Thienyl)-5,6-dihydroxy-4-carboxypyrimidines as Inhibitors of the Hepatitis C Virus NS5B Polymerase: Discovery, SAR, Modeling, and Mutagenesis," Journal of Medicinal Chemistry, 2006, vol. 49 (5), pp. 1693-1705.
Kocsis J., et al., "Effect of a Vasopressin Antagonist d(CH2)5Tyr(Met)AVP on the Development of Renal Vasospasm Induced by Estrin Plus Vasopressin Administration in Rats," Investigative Radiology, 1987, vol. 22 (12), pp. 973-977.
Kocsis J., et al., "Histochemical and Ultrastructural Study of Renal Cortical Necrosis in Rats Treated with Oestrone + Vasopressin, and its Prevention with a Vasopressin Antagonist," British Journal of Experimental Pathology, 1987, vol. 68 (1), pp. 35-43.
Lauretti G.R., "Highlights in Opioid Agonists and Antagonists," Neurotherapeutics, 2006, vol. 6 (4), pp. 613-622.
Lee C.R., et al., "Vasopressin: a New Target for the Treatment of Heart Failure," American Heart Journal, 2003, vol. 146 (1), pp. 9-18.
Lin Y., et al., "New Synthesis of 1,2,4-Triazoles and 1,2,4-Oxadiazoles," The Journal of Organic Chemistry, 1979, vol. 44 (23), pp. 4160-4164.
Lynch J.J., et al., "ABT-594 (a Nicotinic Acetylcholine Agonist): Anti-allodynia in a Rat Chemotherapy-induced Pain Model," European Journal of Pharmacology, 2005, vol. 509 (1), pp. 43-48.
March J., "Advanced Organic Chemistry: Reactions, Mechanisms, and Structure" 3rd Edition, John Wilsey & Sons, 1985, Table of Contents.
Mark n. F., et al., "Kirk-Othmer Encyclopedia of Chemical Technology" Second Completely Revised Edition, John Wiley & Sons Inc., 1972, Table of Contents.
Marubio L.M., et al., "Reduced Antinociception in Mice Lacking Neuronal Nicotinic Receptor Subunits," Nature, 1999, vol. 398 (6730), pp. 805-810.
Maturi M.F., et al., "Coronary Vasoconstriction Induced by Vasopressin. Production of Myocardial Ischemia in Dogs by Constriction of Nondiseased Small Vessels," Circulation, 1991, vol. 83 (6), pp. 2111-2121.
McClelland R.A., "Kinetics and Mechanism of Amide Acetal Hydrolysis," Journal of the American Chemical Society, 1978, vol. 100 (6), pp. 1844-1849.
Nakamura I., et al., "Transition-Metal-Catalyzed Reactions in Heterocyclic Synthesis," Chemical Reviews, 2004, vol. 104 (5), pp. 2127-2198.
Narahashi T., et al., "Mechanisms of Action of Cognitive Enhancers on Neuroreceptors," Biological & Pharmaceutical Bulletin, 2004, vol. 27 (11), pp. 1701-1706.
Non-Final Office Action mailed Oct. 1, 2012 for U.S. Appl. No. 12/746,700, filed Nov. 29, 2010.
Non-Final Office Action mailed Oct. 1, 2012 for U.S. Appl. No. 12/746,707, filed Dec. 7, 2010.
Non-Final Office Action mailed Mar. 2, 2012 for U.S. Appl. No. 12/134,678, filed Jun. 6, 2008.
Non-Final Office Action mailed Aug. 4, 2009 for U.S. Appl. No. 11/440,569, filed May 25, 2006.
Non-Final Office Action mailed Jun. 5, 2009 for U.S. Appl. No. 10/574,211, filed Jan. 22, 2007.
Non-Final Office Action mailed Dec. 9, 2008 for U.S. Appl. No. 11/440,569, filed May 25, 2006.
Non-Final Office Action mailed Dec. 9, 2010 for U.S. Appl. No. 11/953,625, filed Dec. 10, 2007.
Non-Final Office Action mailed Jan. 10, 2012 for U.S. Appl. No. 12/839,612, filed Jul. 20, 2010.
Non-Final Office Action mailed Feb. 11, 2013 for U.S. Appl. No. 13/590,261, filed Aug. 21, 2012.
Non-Final Office Action mailed Oct. 12, 2012 for U.S. Appl. No. 12/746,688, filed Nov. 29, 2010.
Non-Final Office Action mailed Apr. 15, 2011 for U.S. Appl. No. 12/134,678, filed Jun. 6, 2008.
Non-Final Office Action mailed Apr. 18, 2011 for U.S. Appl. No. 12/787,937, filed May 26, 2010.
Non-Final Office Action mailed Aug. 19, 2011 for U.S. Appl. No. 12/521,713, filed Sep. 7, 2010.
Non-Final Office Action mailed Aug. 19, 2011 for U.S. Appl. No. 12/746,700, filed Nov. 29, 2010.
Non-Final Office Action mailed Mar. 19, 2012 for U.S. Appl. No. 13/080,071, filed Apr. 5, 2011.
Non-Final Office Action mailed Jan. 22, 2009 for U.S. Appl. No. 10/574,211, filed Jan. 22, 2007.
Non-Final Office Action mailed Jul. 22, 2011 for U.S. Appl. No. 12/746,688, filed Nov. 29, 2010.
Non-Final Office Action mailed Jul. 22, 2011 for U.S. Appl. No. 12/746,707, filed Dec. 7, 2010.

(56) References Cited

OTHER PUBLICATIONS

Non-Final Office Action mailed Feb. 24, 2012 for U.S. Appl. No. 12/839,595, filed Jul. 20, 2010.
Non-Final Office Action mailed Aug. 30, 2011 for U.S. Appl. No. 12/746,715, filed Dec. 7, 2010.
Non-Final Office Action mailed Nov. 30, 2010 for U.S. Appl. No. 10/574,211, filed Jan. 22, 2007.
Non-Final Office Action mailed Sep. 30, 2011 for U.S. Appl. No. 12/134,678, filed Jun. 6, 2008.
Notice of Allowance mailed Oct. 1, 2010 for U.S. Appl. No. 11/440,569, filed May 25, 2006.
Notice of Allowance mailed Dec. 2, 2009 for U.S. Appl. No. 10/574,211, filed Jan. 22, 2007.
Notice of Allowance mailed Sep. 4, 2012 for U.S. Appl. No. 12/839,612, filed Jul. 20, 2010.
Notice of Allowance mailed May 5, 2010 for U.S. Appl. No. 10/574,211, filed Jan. 22, 2007.
Notice of Allowance mailed Dec. 10, 2012 for U.S. Appl. No. 12/134,678, filed Jun. 6, 2008.
Notice of Allowance mailed Jan. 10, 2011 for U.S. Appl. No. 10/574,211, filed Jan. 22, 2007.
Notice of Allowance mailed Jul. 10, 2012 for U.S. Appl. No. 12/521,713, filed Sep. 7, 2010.
Notice of Allowance mailed Jun. 11, 2013 for U.S. Appl. No. 12/839,595, filed Jul. 20, 2010.
Notice of Allowance mailed Mar. 12, 2010 for U.S. Appl. No. 11/440,569, filed May 25, 2006.
Notice of Allowance mailed Nov. 13, 2012 for U.S. Appl. No. 12/521,713, filed Sep. 7, 2010.
Notice of Allowance mailed Apr. 15, 2013 for U.S. Appl. No. 12/746,688, filed Nov. 29, 2010.
Notice of Allowance mailed Apr. 15, 2013 for U.S. Appl. No. 12/746,700, filed Nov. 29, 2010.
Notice of Allowance mailed Jun. 24, 2010 for U.S. Appl. No. 11/440,569, filed May 25, 2006.
Notice of Allowance mailed Jun. 25, 2013 for U.S. Appl. No. 12/521,713, filed Sep. 7, 2010.
Notice of Allowance mailed Jun. 26, 2012 for U.S. Appl. No. 12/839,595, filed Jul. 20, 2010.
Notice of Allowance mailed May 28, 2013 for U.S. Appl. No. 12/746,715, filed Dec. 7, 2010.
Office action mailed Dec. 1, 2011 for European Application No. 08770247.8 filed Jun. 6, 2008.
Office action mailed Sep. 10, 2012 for European Application No. 10720520.5 filed May 26, 2010.
Office action mailed Nov. 17, 2011 for European Application No. 10163998.7 filed Dec. 12, 2007.
Office action mailed Jun. 18, 2012 for European Application No. 10163998.7 filed Dec. 12, 2007.
Office action mailed Mar. 29, 2012 for European Application No. 08770247.8 filed Jun. 6, 2008.
Oshikawa S., et al., "Vasopressin Stimulates Insulin Release from Islet Cells through V1b Receptors: a Combined Pharmacological/knockout Approach," Molecular Pharmacology, 2004, vol. 65 (3), pp. 623-629.
Pasternak G.W., "Pharmacological Mechanisms of Opioid Analgesics," Clinical Neuropharmacology, 1993, vol. 16 (1), pp. 1-18.
Pavo I., et al., "Vasopressin Deficiency Decreases the Frequency of Gastroduodenal Ulceration in Humans," Journal of Physiology, 2000, vol. 94 (1), pp. 63-66.
Poulain R.F., et al., "Parallel Synthesis of 1,2,4-oxadiazoles from carboxylic Acids Using an Improved, Uronium-based Activation," Tetrahedron Letters, 2001, vol. 42 (8), pp. 1495-1498.
Prescott D.M., "Methods in Cell Biology", Academic Press, 1976, Table of Contents.
Qian X., et al., "Syntheses and Insecticidal Activities of Novel 2,5-Disubstituted- 1,3,4-Oxadiazoles," Journal of Chemical Technology and Biotechnology, 1996, vol. 67 (2), pp. 124-130.

Rashid M.H., et al., "Tonic Inhibitory Role of Alpha4beta2 Subtype of Nicotinic Acetylcholine Receptors on Nociceptive Transmission in the Spinal Cord in Mice," Pain, 2006, vol. 125 (1-2), pp. 125-135.
Reynaud P. et al., "A New Synthetic Route to 1,3,4-oxadiazoles. Pharmacological Study of Some New Derivatives", Journal of Heterocyclic Chemistry, 1992, vol. 29 (4), pp. 991-993.
Ring R.H., et al., "The Central Vasopressinergic System: Examining the Opportunities for Psychiatric Drug Development," Current Pharmaceutical Design, 2005, vol. 11 (2), pp. 205-225.
Roche E.B., ed., Bioreversible Carries in Drug Design Theory and Application, Pergamon Press, 1987, Table of Contents.
Rueter L.E., et al., "Abt-089: Pharmacological Properties of a Neuronal Nicotinic Acetylcholine Receptor Agonist for the Potential Treatment of Cognitive Disorders," CNS Drug Review, 2004, vol. 10 (2), pp. 167-182.
Ryckmans T., et al., "Modulation of the Vasopressin System for the Treatment of CNS Diseases," Current opinion in drug discovery & development, 2010, vol. 13 (5), pp. 538-547.
Scheurer M.A., et al., "Vasopressin to Attenuate Pulmonary Hypertension and Improve Systemic Blood Pressure after Correction of Obstructed Total Anomalous Pulmonary Venous Return," The Journal of Thoracic and Cardiovascular Surgery, 2005, vol. 129 (2), pp. 464-466.
Serradeil-Le Gal C., et al., "Characterization of (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist," Journal of Pharmacology and Experimental Therapeutics, 2002, vol. 300 (3), pp. 1122-1130.
Skoubis P.D., et al., "Mapping Brain Activity Following Administration of a Nicotinic Acetylcholine Receptor Agonist, ABT-594, Using Functional Magnetic Resonance Imaging in Awake Rats," Neuroscience, 2006, vol. 137 (2), pp. 583-591.
Smalley S.L., "Genetic Influences in Childhood-Onset Psychiatric Disorders: Autism and Attention-Deficit/hyperactivity Disorder," American Journal of Human Genetics, 1997, vol. 60 (6), pp. 1276-1282.
Sobol E., et al., "Tetramethylcyclopropyl Analogue of a Leading Antiepileptic Drug, Valproic Acid. Synthesis and Evaluation of Anticonvulsant Activity of Its Amide Derivatives," Journal of Medicinal Chemistry, 2004, vol. 47 (17), pp. 4316-4326.
Stella V.J., "Prodrugs as Therapeutics," Expert Opinion on Therapeutic Patents, 2004, vol. 14 (3), pp. 277-280.
Street L.J., et al., "Synthesis and Serotonergic Activity of 5-(Oxadiazolyl)tryptamines: Patent Agonists for 5-HTID Receptors," Journal of Medicinal Chemistry, 1993, vol. 36 (11), pp. 1529-1538.
Supplementary Partial European Search Report for Application No. 08770247, mailed on Mar. 16, 2012, 4 pages.
Testa B., et al., "Prodrug Research: Futile or Fertile?," Biochemical Pharmacology, 2004, vol. 68, pp. 2097-2106.
Thibonnier M., "Development and Therapeutic Indications of Orally-active Non-peptide Vasopressin Receptor Antagonists," Expert Opinion on Investigational Drugs, 1998, vol. 7 (5), pp. 729-740.
Thibonnier M., et al., "Vasopressin Receptor Antagonists in Heart Failure," Current Opinion in Pharmacology, 2003, vol. 3 (6), pp. 683-687.
Venkatesh S., et al., "Role of the Development Scientist in Compound Lead Selection and Optimization," Journal of Pharmaceutical Sciences, 2000, vol. 89 (2), pp. 145-154.
Wakefield B., Fluorinated Pharmaceuticals, Innovations in Pharmaceutical Technology, 2000, pp. 74-78.
Wang Y., et al., "A Simple and Effcient One Step Synthesis of 1,3,4-Oxadiazoles Utilizing Polymer-Supported Reagents and Microwave Heating," Tetrahedron Letters, 2006, vol. 47 (1), pp. 105-108.
Webster M., "Ninth New Collegiate Dictionary" Definition of Prevention, Springfield, Massachusetts, 2000, pp. 933.
Wersinger S.R., et al., "Vasopressin V1b Receptor Knockout Reduces Aggressive Behavior in Male Mice," Molecular Psychiatry, 2002, vol. 7 (9), pp. 975-984.

(56) References Cited

OTHER PUBLICATIONS

Wiffen P.J., et al., Gabapentin for Acute and Chronic Pain (Review), Cochrane Database of Systematic Reviews, 2005, vol. 20 (3), pp. 1-23.

Wilens T.E., et al., "ABT-089, A Neuronal Nicotinic Receptor Partial Agonist, for the Treatment of Attnetion-Defecit/Hyperactivity Disorder in Adults: Results of a Pilot Study," Biological Psychiatry, 2006, vol. 59 (11), pp. 1065-1070.

Wolff, Mandred E.,, "Burger's Medicinal Chemistry and Drug Discovery," Principles and Practice, 1995, 975-977, 5th Ed,vol. 1, John Wiley & Sons.

Yatagai T., et al., "Close Association of Severe Hyponatremia with Exaggerated Release of Arginine Vasopressin in Elderly Subjects with Secondary Adrenal Insufficiency," European Journal of Endocrinology, 2003, vol. 148 (2), pp. 221-226.

Final Office Action mailed Dec. 3, 2012 for U.S. Appl. No. 13/361,488, filed Jan. 30, 2012.

Final Rejection mailed Oct. 10, 2013 for U.S. Appl. No. 13/590,261, filed Aug. 21, 2012.

Griebel G., et al., "The Vasopressin V1b Receptor as a Therapeutic Target in Stress-Related Disorders," Current Drug Targets. CNS and Neurological Disorders, 2003, vol. 2 (3), pp. 191-200.

Non-Final Office Action mailed Aug. 1, 2013 for U.S. Appl. No. 12/521,713, filed Sep. 7, 2010.

Non-Final Office Action mailed Aug. 2, 2013 for U.S. Appl. No. 12/746,700, filed Nov. 29, 2010.

Non-Final Office Action mailed Oct. 8, 2013 for U.S. Appl. No. 13/080,071, filed Apr. 5, 2011.

Non-Final Office Action mailed Jul. 20, 2012 for U.S. Appl. No. 13/361,488, filed Jan. 30, 2012.

Notice of Allowance mailed Aug. 20, 2013 for U.S. Appl. No. 12/746,700, filed Nov. 29, 2010.

Office action mailed Aug. 1, 2013 for European Application No. 10163998.7 filed Dec. 12, 2007.

Lemmens-Gruber R., et al., "Vasopressin Antagonists," Cellular and Molecular Life Sciences, 2006, vol. 63 (15), pp. 1766-1779.

Non-Final Office Action mailed Sep. 12, 2014 for U.S. Appl. No. 14/251,384, filed Apr. 11, 2014.

Non-Final Office Action mailed Sep. 25, 2014 for U.S. Appl. No. 14/040,412, filed Sep. 27, 2013.

Notice of Allowance mailed Sep. 2, 2014 for U.S. Appl. No. 13/080,071, filed Apr. 5, 2011.

Non-Final Office Action mailed Dec. 3, 2014 for U.S. Appl. No. 14/252,425, filed Apr. 14, 2014.

Notice of Allowance and Examiner Initiated Interview Summary mailed Jan. 5, 2015 for U.S. Appl. No. 12/787,937, filed May 26, 2010.

Notice of Allowance mailed Dec. 24, 2014 for U.S. Appl. No. 12/746,707, filed Dec. 7, 2010.

European Search Report for Application No. EP15180552, mailed on Dec. 15, 2015, 12 pages.

Non-Final Office Action mailed Feb. 2, 2016 for U.S. Appl. No. 14/877,783, filed Oct. 7, 2015.

Non-Final Office Action mailed Dec. 17, 2015 for U.S. Appl. No. 14/040,412, filed Sep. 27, 2013.

Gruber R.L., et al., "Drugs of the Future: Review Vasopressin Antagonists," Cellular and Molecular Life Sciences, 2006, vol. 63, pp. 1769-1773.

Koob G.F., et al., "A Role for Brain Stress Systems in Addiction," Neuron, 2008, vol. 59 (1), pp. 11-34.

Non Final Rejection mailed Jan. 16, 2015 for U.S. Appl. No. 14/481,847, filed Sep. 9, 2014.

Notice of Allowance mailed Apr. 13, 2015 for U.S. Appl. No. 13/080,071, filed Apr. 5, 2011.

Office Action mailed Apr. 13, 2015 for U.S. Appl. No. 14/554,734, filed Nov. 26, 2014.

Office Action mailed Apr. 15, 2015 for U.S. Appl. No. 14/040,412, filed Sep. 27, 2013.

Office Action mailed Apr. 21, 2015 for U.S. Appl. No. 14/252,425, filed Apr. 14, 2014.

Office Action mailed Apr. 24, 2015 for U.S. Appl. No. 14/251,384, filed Apr. 11, 2014.

Zhou Y., et al., "Involvement of Arginine Vasopressin and V1b Receptor in Heroin withdrawal and Heroin Seeking Precipitated by Stress and by Heroin," Neuropsychopharmacology, 2008, vol. 33 (2), pp. 226-236.

United States Patent Office Action for U.S. Appl. No. 14/251,384 dated Aug. 26, 2015 (7 pages).

United States Patent Office Notice of Allowance for U.S. Appl. No. 13/080,071 dated Jul. 13, 2015 (8 pages).

United States Patent Office Action for U.S. Appl. No. 14/252,425 dated Aug. 27, 2015 (6 pages).

Final Office Action mailed Sep. 22, 2015 for U.S. Appl. No. 14/554,734, filed Nov. 26, 2014.

Ofice Action mailed Oct. 8, 2015 for U.S. Appl. No. 14/740,598, filed Jun. 16, 2015.

* cited by examiner

HETEROARYL-SUBSTITUTED 1,3-DIHYDROINDOL-2-ONE DERIVATIVES AND MEDICAMENTS CONTAINING THEM

CROSS REFERENCE TO RELATED APPLICATIONS

This is a divisional of U.S. patent application Ser. No. 12/839,595, filed on Jul. 20, 2010, which is a divisional of U.S. patent application Ser. No. 10/574,211, filed on Jan. 22, 2007, now U.S. Pat. No. 7,902,379, which is a 371 of International Patent Application No. PCT/EP2004/010940, filed on Sep. 30, 2004, which is a continuation-in-part of U.S. patent application Ser. No. 10/675,300, filed on Sep. 30, 2003, the contents of all of which are fully incorporated herein by reference.

The present invention relates to novel 1,3-dihydroindol-2-one (oxindole) derivatives and to medicaments containing them for the treatment of diseases.

The role of vasopressin in various pathological states has been the subject of intensive research in recent years, and the selective antagonism of the various vasopressin receptors opens up novel clinical prospects. At present, three receptors (V1a, V1b or V3 and V2) by which vasopressin mediates its effect are known. In contrast to the other two receptors, the vasopressin V1b receptor is mainly found in the CNS. This suggests that in particular CNS effects of vasopressin are mediated by the V1b receptor. Thus, it has also been found that an antagonist of the V1b receptor shows anxiolytic and antidepressant effects (Griebel et al., PNAS 99, 6370 (2002); Serradeil-Le Gal et al., J. Pharm. Exp. Ther. 300, 1122 (2002)). Since the models used allow a certain forecast of a clinical effect, antagonists of the vasopressin V1b receptor might be useful for the treatment of emotional disturbances, e.g. stress, anxiety and depression.

WO 93/15051 and WO 98/25901 have already described 1-phenylsulfonyl-1,3-dihydro-2H-indol-2-ones in which the oxindole framework is substituted in position 3 by two alkyl radicals, which may also be a cycloalkyl radical (spiro linkage), as ligands of vasopressin receptors. An alternative possibility is for the spiro ring to contain heteroatoms such as oxygen and nitrogen (optionally with substituents).

WO 95/18105 describes 1-phenylsulfonyl-1,3-dihydro-2H-indol-2-ones which have a nitrogen atom in position 3 as ligands of vasopressin receptors. Additionally bonded in position 3 are radicals which may be alkyl, cycloalkyl, phenyl or benzyl radicals (optionally with substituents in each case).

Other publications describe compounds which have nitrogen-containing rings (e.g. proline, homoproline, morpholine, tetrahydroisoquinoline, dihydroindole; optionally with substituents in each case) bonded via their nitrogen atom to position 3 of the oxindole framework, but which have phenylsulfonyl or phenyl radicals (optionally with substituents) both in position 1 and position 3 on the oxindole ring.

The object of the present invention is to provide additional compounds for the treatment or prophylaxis of various vasopressin-dependent or oxytocin-dependent diseases which have high activity.

The object has been achieved by a compound of the formula (I)

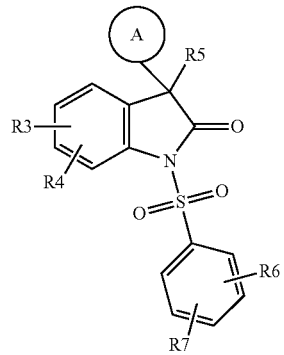

in which

A is an aromatic heteromonocyclic, or an aromatic or partially aromatic heterobicyclic ring,
  where the heterocycles are 5- or 6-membered rings and comprise up to 4 heteroatoms selected from the group consisting of N, O and S, and up to 2 oxo groups, where not more than one of the heteroatoms is an oxygen atom,
  and A may be substituted by radicals $R^{11}$, $R^{12}$ and/or $R^{13}$, where
  $R^{11}$, $R^{12}$ and $R^{13}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, $R^3$ and $R^4$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, or $R^3$ and $R^4$ are connected to give —CH=CH—CH=CH—, —(CH$_2$)$_4$— or —(CH$_2$)$_3$—, $R^5$ is a radical (W)—(X)—(Y)—Z, where
  W is selected from the group consisting of $C_1$-$C_4$-alkylen, $C_2$-$C_4$-alkenylen, $C_2$-$C_4$-alkynylen, O, O—($C_1$-$C_4$-alkylen), S, S—($C_1$-$C_4$-alkylen), $NR^{54}$, $NR^{54}$—($C_1$-$C_4$-alkylen) and a bond,
  X is selected from the group consisting of CO, CO—O, $SO_2$, $NR^{54}$, $NR^{54}$—CO, $NR^{54}$—$SO_2$, CO—$NR^{58}$ and a bond,
  Y is $C_1$-$C_6$-alkylen, $C_2$-$C_6$-alkenylen, $C_2$-$C_6$-alkynylen, or a bond,
  Z is selected from the group consisting of hydrogen, E, O—$R^{52}$, $NR^{51}R^{52}$, S—$R^{52}$, where
  E is an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, said ring may comprise up to two oxo groups, and may be substituted by radicals $R^{55}$, $R^{56}$, $R^{57}$, and/or up to three radicals $R^{53}$,
  $R^{51}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{53}$, $R^{52}$ at each occurrence is independently selected from the group consisting of hydrogen, $C_1$-$C_6$-alkyl, $C_2$-$C_6$-alkenyl, $C_2$-$C_6$-alkynyl, E and $C_1$-$C_4$-alkylen-E, $R^{53}$ at each occurrence is independently selected from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, $R^{54}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{59}$, $R^{55}$ at each occurrence is independently selected from the group consisting of hydrogen, $C_1$-$C_6$-alkyl, $C_2$-$C_6$-alkenyl, $C_2$-$C_6$-alkynyl, phenyl, $C_1$-$C_4$-alkylen-phenyl, where the ring may be substituted by up to two radicals $R^{60}$, and OH, O—$C_1$-$C_4$-alkyl, O-phenyl, O—$C_1$-$C_4$-alkylen-phenyl, $NH_2$, $NH(C_1$-$C_4$-alkyl) and $N(C_1$-$C_4$-alkyl)$_2$, $R^{56}$ at each occurrence is independently a group $Q^1$-$Q^2$-$Q^3$, $Q^3$, where $Q^1$ is selected from the group consisting of a bond, $C_1$-$C_4$-alkylen, $C_2$-$C_4$-alkenylen, $C_2$-$C_4$-alkynylen, $C_1$-$C_4$-alkylen-N($C_1$-$C_4$-alkyl), N($C_1$-$C_4$-alkyl), $C_1$-$C_4$-alkylen-NH, NH, N($C_1$-$C_4$-alkyl)-$C_1$-$C_4$-alkylen, NH—$C_1$-$C_4$-alkylen, O, $C_1$-$C_4$-alkylen-O, O—$C_1$-$C_4$-alkylen, CO—NH, CO—N($C_1$-$C_4$-alkyl), NH—CO, N($C_1$-$C_4$-alkyl)-CO, CO, $SO_2$, SO, S, O, $SO_2$—NH, $SO_2$—N($C_1$-$C_4$-alkyl), NH—$SO_2$, N($C_1$-$C_4$-alkyl)-$SO_2$, O—CO—NH, O—CO—N($C_1$-$C_4$-alkyl), NH—CO—O, N($C_1$-$C_4$-alkyl)-CO—O, N($C_1$-$C_4$-alkyl)-CO—N($C_1$-$C_4$-alkyl), NH—CO—N($C_1$-$C_4$-alkyl), N($C_1$-$C_4$-alkyl)-CO—NH, and NH—CO—NH, $Q^2$ is selected from the group consisting of $C_1$-$C_4$-alkylen, $C_2$-$C_4$-alkenylen, $C_2$-$C_4$-alkynylen, and a bond, $Q^3$ is a hydrogen or an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, which may comprise up to two oxo groups and may be substituted by the radicals $R^{63}$, $R^{64}$ and/or $R^{65}$, $R^{57}$ at each occurrence is independently selected from the group consisting of hydrogen, $C_1$-$C_6$-alkyl, phenyl, $C_1$-$C_4$-alkylen-phenyl, COOH, CO—O—$C_1$-$C_4$-alkyl, $CONH_2$, CO—NH—$C_1$-$C_4$-alkyl, CO—N($C_1$-$C_4$-alkyl)$_2$, CO—$C_1$-$C_4$-alkyl, $CH_2$—$NH_2$, $CH_2$—NH—$C_1$-$C_4$-alkyl and $CH_2$—N($C_1$-$C_4$-alkyl)$_2$, $R^{58}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{62}$, $R^{59}$, $R^{60}$ and $R^{62}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, $R^{63}$, $R^{64}$ and $R^{65}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, $R^6$ and $R^7$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, and their tautomeric forms, enantiomeric and diastereomeric forms, and prodrugs thereof.

Ring A is preferably selected from the group consisting of aromatic heteromonocyclic and aromatic heterobicyclic systems comprising 1 or 2 heteroatoms, where one of the 2 heteroatoms is nitrogen, more preferably from benzothiazole, pyrimidine, pyridine, pyridazine, pyrazine, isoquinoline, quinoline, thiazole, benzimidazole, imidazole, benzoxazole, benzothiophene, thiophene, benzofuran and furan.

In a more preferred embodiment ring A is selected from the group consisting of pyridine, pyrimidine, pyrazine, thiophene, benzofuran and benzothiazole.

In a further preferred embodiment of the compound of formula (I), $R^{11}$ and $R^{12}$ are selected independently of one another from the group consisting of fluorine, chlorine, OH, O—$C_1$-$C_4$-alkyl and $C_1$-$C_4$-alkyl. More preferably, $R^{11}$ and/or $R^{12}$ are independently of one another methyl, methoxy or ethoxy.

Examples of ring A, substituted by $R^{11}$ and/or $R^{12}$, in the compound of formula (I) are 2-methoxypyridine-3-yl, 2-ethoxypyridine-3-yl, 2-hydroxypyridine-3-yl, 2,4-dimethoxypyrimidine-5-yl, 2,6-dimethoxypyridine-3-yl, 3-methoxypyridine-2-yl, 3-methoxypyridine-4-yl, 4-methoxypyridine-3-yl, 3-methoxypyrazine-2-yl, 3-methylthiophen-2-yl, 3-methylpyridin-2-yl, pyridin-2-yl or 6-chlor-2-methoxypyridin-3-yl, preferably 2-methoxypyridine-3-yl, 2-ethoxypyridine-3-yl, 2,4-dimethoxy-pyrimidine-5-yl or 2,6-dimethoxypyridine-3-yl, and more preferably 2-methoxypyridine-3-yl.

In case of $R^{11}$ or $R^{12}$ being OH, the resultant substituted ring A may predominantly be present in form of its tautomer like, for example, 1,2-dihydro-2-oxopyridine-3-yl.

In a further preferred embodiment of the compounds of formulae (I) $R^6$ and $R^7$ are independently of one another hydrogen, fluorine, chlorine, bromine, iodine, $C_1$-$C_4$-alkyl, O—$C_1$-$C_4$-alkyl, CN, $CF_3$ or $OCF_3$, preferably hydrogen, fluorine, chlorine, methyl, methoxy, ethoxy or CN.

Furthermore, for the compounds of formula (I) $R^6$ is preferably hydrogen, methoxy, methyl, F, Cl or CN and/or $R^7$ is preferably hydrogen, methoxy, methyl, F or Cl.

The present application additionally relates to a compound of the formula (II)

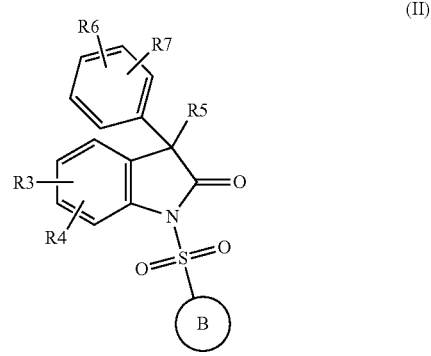

in which

B is selected from the group consisting of thiophene, furan, pyrrole, pyridine, quinoline, tetrahydroquinoline, isoquinoline, tetrahydroisoquinoline, benzothiophene, benzofuran, dihydrobenzofuran, indole, dihydroisoindole,
an aromatic heteromonocyclic and an aromatic or partially aromatic heterobicyclic ring,
  where the heterocycles are 5- or 6-membered rings and comprise 2 to 4 heteroatoms selected from the group consisting of N, O and S, and up to 2 oxo groups, and
B may be substituted by the radicals $R^{21}$, $R^{22}$ and/or $R^{23}$,
$R^{21}$, $R^{22}$ and $R^{23}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, morpholin-4-yl, pyrrolidin-1-yl, piperidin-1-yl, 4-piperazin-1-yl, 4-($C_1$-$C_4$-alkyl)-piperazin-1-yl,
$R^3$ and $R^4$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, or
$R^3$ and $R^4$ are connected to give —CH═CH—CH═CH—, —$(CH_2)_4$— or —$(CH_2)_3$—,
$R^5$ is a radical (W)—(X)—(Y)—Z, where
  W is selected from the group consisting of $C_1$-$C_4$-alkylen, $C_2$-$C_4$-alkenylen, $C_2$-$C_4$-alkynylen, O, O—($C_1$-$C_4$-alkylen), S, S—($C_1$-$C_4$-alkylen), $NR^{54}$, $NR^{54}$—($C_1$-$C_4$-alkylen) and a bond,
  X is selected from the group consisting of CO, CO—O, $SO_2$, $NR^{54}$, $NR^{54}$—CO, $NR^{54}$—$SO_2$, CO—$NR^{58}$ and a bond,
  Y is $C_1$-$C_6$-alkylen, $C_2$-$C_6$-alkenylen, $C_2$-$C_6$-alkynylen, or a bond,
  Z is selected from the group consisting of hydrogen, E, O—$R^{52}$, $NR^{51}R^{52}$, S—$R^{52}$, where
    E is an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, said ring may comprise up to two oxo groups, and may be substituted by radicals $R^{55}$, $R^{56}$, $R^{57}$ and/or up to three radicals $R^{53}$ and,
  $R^{51}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{53}$,
  $R^{52}$ at each occurrence is independently selected from the group consisting of hydrogen, $C_1$-$C_6$-alkyl, $C_2$-$C_6$-alkenyl, $C_2$-$C_6$-alkynyl, E and $C_1$-$C_4$-alkylen-E,
  $R^{53}$ at each occurrence is independently selected from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$,
  $R^{54}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{59}$,
  $R^{55}$ at each occurrence is independently selected from the group consisting of $C_1$-$C_6$-alkyl, $C_2$-$C_6$-alkenyl, $C_2$-$C_6$-alkynyl, phenyl, $C_1$-$C_4$-alkylen-phenyl, where the ring may be substituted by up to two radicals $R^{60}$, and OH, O—$C_1$-$C_4$-alkyl, O-phenyl, O—$C_1$-$C_4$-alkylen-phenyl, $NH_2$, NH($C_1$-$C_4$-alkyl) and N($C_1$-$C_4$-alkyl)$_2$, $R^{56}$ is a group $Q^1$-$Q^2$-$Q^3$, $Q^3$, where
  $Q^1$ is selected from the group consisting of a bond, $C_1$-$C_4$-alkylen, $C_2$-$C_4$-alkenylen, $C_2$-$C_4$-alkynylen, $C_1$-$C_4$-alkylen-N($C_1$-$C_4$-alkyl), N($C_1$-$C_4$-alkyl), $C_1$-$C_4$-alkylen-NH, NH, N($C_1$-$C_4$-alkyl)-$C_1$-$C_4$-alkylen, NH—$C_1$-$C_4$-alkylen, O, $C_1$-$C_4$-alkylen-O, O—$C_1$-$C_4$-alkylen, CO—NH, CO—N($C_1$-$C_4$-alkyl), NH—CO, N($C_1$-$C_4$-alkyl)-CO, CO, $SO_2$, SO, S, O, $SO_2$—NH, $SO_2$—N($C_1$-$C_4$-alkyl), NH—$SO_2$, N($C_1$-$C_4$-alkyl)-$SO_2$, O—CO—NH, O—CO—N($C_1$-$C_4$-alkyl), NH—CO—O, N($C_1$-$C_4$-alkyl)-CO—O, N($C_1$-$C_4$-alkyl)-CO—N($C_1$-$C_4$-alkyl), NH—CO—N($C_1$-$C_4$-alkyl), N($C_1$-$C_4$-alkyl)-CO—NH, and NH—CO—NH,
  $Q^2$ is selected from the group consisting of $C_1$-$C_4$-alkylen, $C_2$-$C_4$-alkenylen, $C_2$-$C_4$-alkynylen, and a bond,
  $Q^3$ is a hydrogen or an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, which may comprise up to two oxo groups and may be substituted by the radicals $R^{63}$, $R^{64}$ and/or $R^{65}$,
  $R^{57}$ at each occurrence is independently selected from the group consisting of hydrogen, $C_1$-$C_6$-alkyl, phenyl, $C_1$-$C_4$-alkylen-phenyl, COOH, CO—O—$C_1$-$C_4$-alkyl, $CONH_2$, CO—NH—$C_1$-$C_4$-alkyl, CO—N($C_1$-$C_4$-alkyl)$_2$, CO—$C_1$-$C_4$-alkyl, $CH_2$—$NH_2$, $CH_2$—NH—$C_1$-$C_4$-alkyl and $CH_2$—N($C_1$-$C_4$-alkyl)$_2$,
  $R^{58}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{62}$,
  $R^{59}$, $R^{69}$ and $R^{62}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$,
  $R^{63}$, $R^{64}$ and $R^{65}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$,
$R^6$ and $R^7$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$,
and their tautomeric forms, enantiomeric and diastereomeric forms, and prodrugs thereof.

Ring B is preferably selected from the group consisting of thiophene, furan, pyrrole, pyrazole, isoxazole, pyridine, pyrimidine, quinoline, isoquinoline, tetrahydroisoquinoline, benzothiophene, benzofuran, indole, imidazole, thiazole, imidazothiazole, benzooxazine and quinoxaline.

In a more preferred embodiment ring B is selected from the group consisting of pyridine, imidazole, thiophene, benzothiophene and quinoline.

Even more preferably, ring B is selected from

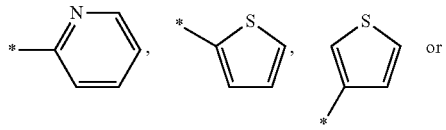

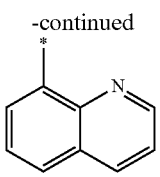

In a further preferred embodiment of the compound of formula (II), $R^{21}$ and $R^{22}$ are selected independently of one another from the group consisting of hydrogen, chlorine, bromine, $C_1$-$C_4$-alkyl and O—$C_1$-$C_4$-alkyl. Particularly, $R^{21}$ and $R^{22}$ are independently of one another hydrogen, chlorine, bromine, methyl or methoxy.

In further particularly preferred embodiments, B is

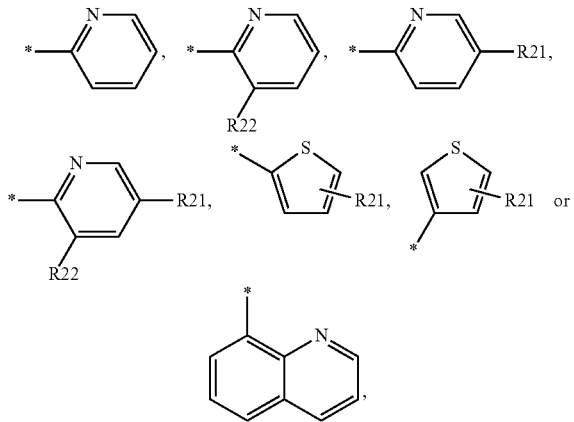

wherein
$R^{21}$ is selected from methyl, methoxy, chlorine or bromine, and
$R^{22}$ is methyl.

In a further preferred embodiment of the compounds of formula (II) $R^6$ and $R^7$ are independently of one another hydrogen, fluorine, chlorine, bromine, iodine, $C_1$-$C_4$-alkyl, O—$C_1$-$C_4$-alkyl, $CF_3$ or $OCF_3$, preferably hydrogen, fluorine, chlorine, methyl, ethyl, propyl, i-propyl, methoxy, ethoxy, propoxy, i-propoxy.

For the compounds of formula (II) $R^6$ is preferably hydrogen, methoxy, ethoxy, propoxy, i-propoxy, methyl, ethyl, fluorine or chlorine, most preferably methoxy or ethoxy. Further, $R^6$ is more preferably in position 2 of the phenyl ring.

For the compounds of formula (II) $R^7$ is preferably hydrogen, methoxy, F or Cl, most preferably hydrogen.

The present invention additionally relates to a compound of the formula (III),

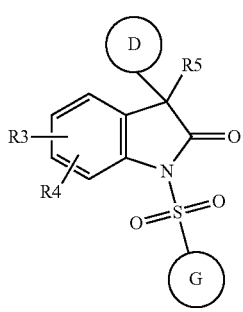

(III)

in which
D is an aromatic heteromonocyclic, or an aromatic or partially aromatic heterobicyclic ring, where the heterocycles are 5- or 6-membered rings and comprise up to 4 heteroatoms selected from the group consisting of N, O and S, and up to 2 oxo groups, and D may be substituted by radicals $R^{21}$, $R^{22}$ and/or $R^{23}$, G is an aromatic heteromonocyclic, aromatic or partially aromatic heterobicyclic ring,
where the heterocycles are 5- or 6-membered rings and comprise up to 4 heteroatoms selected from the group consisting of N, O and S, and up to 2 oxo groups and G may be substituted by radicals $R^{71}$, $R^{72}$ and/or $R^{73}$, $R^{21}$, $R^{22}$, $R^{23}$, $R^{71}$, $R^{72}$ and $R^{73}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, morpholin-4-yl, pyrrolidin-1-yl, piperidin-1-yl, 4-piperazin-1-yl, 4-($C_1$-$C_4$-alkyl)-piperazin-1-yl, $R^3$ and $R^4$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, or $R^3$ and $R^4$ are connected to give —CH=CH—CH=CH—, —($CH_2$)$_4$— or —($CH_2$)$_3$—, $R^5$ is a radical (W)—(X)—(Y)—Z, where
W is selected from the group consisting of $C_1$-$C_4$-alkylen, $C_2$-$C_4$-alkenylen, $C_2$-$C_4$-alkynylen, O, O—($C_1$-$C_4$-alkylen), S, S—($C_1$-$C_4$-alkylen), $NR^{54}$, $NR^{54}$—($C_1$-$C_4$-alkylen) and a bond, X is selected from the group consisting of CO, CO—O, $SO_2$, $NR^{54}$, $NR^{54}$—CO, $NR^{54}$—$SO_2$, CO—$NR^{58}$ and a bond, Y is $C_1$-$C_6$-alkylen, $C_2$-$C_6$-alkenylen, $C_2$-$C_6$-alkynylen, or a bond, Z is selected from the group consisting of hydrogen, E, O—$R^{52}$, $NR^{51}R^{52}$, S—$R^{52}$, where
E is an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, which may comprise up to two oxo groups, and
E may be substituted by radicals $R^{55}$, $R^{56}$, $R^{57}$ and/or up to three radicals $R^{53}$, $R^{51}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{53}$, $R^{52}$ at each occurrence is independently selected from the group consisting of hydrogen, $C_1$-$C_6$-alkyl, $C_2$-$C_6$-alkenyl, $C_2$-$C_6$-alkynyl, E and $C_1$-$C_4$-alkylen-E, $R^{53}$ at each occurrence is independently selected from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, $R^{54}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{59}$, $R^{55}$ at each occurrence is independently selected from the group consisting of hydrogen, $C_1$-$C_6$-alkyl, $C_2$-$C_6$-alkenyl, $C_2$-$C_6$-alkynyl, phenyl, $C_1$-$C_4$-alkylen-phenyl, where the ring may be substituted by up to two radicals $R^{60}$, and OH, O—$C_1$-$C_4$-alkyl, O-phenyl, O—$C_1$-$C_4$-alkylen-phenyl, $NH_2$, $NH(C_1$-$C_4$-alkyl) and $N(C_1$-$C_4$-alkyl)$_2$, $R^{56}$ is a group $Q^1$-$Q^2$-$Q^3$, where $Q^1$ is selected from the group consisting of a bond, $C_1$-$C_4$-alkylen, $C_2$-$C_4$-alkenylen, $C_2$-$C_4$-alkynylen, $C_1$-$C_4$-alkylen-N($C_1$-$C_4$-alkyl), N($C_1$-$C_4$-alkyl), $C_1$-$C_4$-alkylen-NH, NH, N($C_1$-$C_4$-alkyl)-$C_1$-$C_4$-alkylen, NH—$C_1$-$C_4$-alkylen, O, $C_1$-$C_4$-alkylen-O, O—$C_1$-$C_4$-alkylen, CO—NH, CO—N($C_1$-$C_4$-alkyl), NH—CO, N($C_1$-$C_4$-alkyl)-CO, CO, $SO_2$, SO, S, O, $SO_2$—NH, $SO_2$—N($C_1$-$C_4$-alkyl), NH—$SO_2$, N($C_1$-$C_4$-alkyl)-$SO_2$, O—CO—NH, O—CO—N($C_1$-$C_4$-alkyl), NH—CO—O, N($C_1$-$C_4$-alkyl)-CO—O, N($C_1$-$C_4$-alkyl)-CO—N($C_1$-$C_4$-alkyl), NH—CO—N($C_1$-$C_4$-alkyl), N($C_1$-$C_4$-alkyl)-CO—NH, and NH—CO—NH, $Q^2$ is selected from the group consisting of $C_1$-$C_4$-alkylen, $C_2$-$C_4$-alkenylen, $C_2$-$C_4$-alkynylen, and a bond, $Q^3$ is a hydrogen or an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, which may comprise up to two oxo groups and may be substituted by the radicals $R^{63}$, $R^{64}$ and/or $R^{65}$, $R^{57}$ at each occurrence is independently selected from the group consisting of $C_1$-$C_6$-alkyl, phenyl, $C_1$-$C_4$-alkylen-phenyl, COOH, CO—O—$C_1$-$C_4$-alkyl, $CONH_2$, CO—NH—$C_1$-$C_4$-alkyl, CO—N($C_1$-$C_4$-alkyl)$_2$, CO—$C_1$-$C_4$-alkyl, $CH_2$—$NH_2$, $CH_2$—NH—$C_1$-$C_4$-alkyl and $CH_2$—N($C_1$-$C_4$-alkyl)$_2$, $R^{58}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{62}$, $R^{59}$, $R^{60}$ and $R^{62}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, $R^{63}$, $R^{64}$ and $R^{65}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$, and their tautomeric forms, enantiomeric and diastereomeric forms, and prodrugs thereof.

Ring D is preferably selected from the group consisting of aromatic heteromonocyclic and aromatic heterobicyclic systems comprising 1 or 2 heteroatoms, where one of the 2 heteroatoms is nitrogen, more preferably from benzothiazole, pyrimidine, pyridine, pyridazine, pyrazine, isoquinoline, quinoline, thiazole, benzimidazole, imidazole, benzoxazole, benzothiophene, thiophene, benzofuran and furan.

In a particularly preferred embodiment ring D is selected from the group consisting of pyridine, pyrimidine, pyrazine, thiophene, benzofuran and benzothiazole.

In a further preferred embodiment of the compound of formula (III) $R^{21}$ and $R^{22}$ are selected independently of one another from the group consisting of hydroxy, fluorine, chlorine, $C_1$-$C_4$-alkyl and O—$C_1$-$C_4$-alkyl. Particularly, $R^{21}$ and $R^{22}$ are independently of one another hydrogen, hydroxy, chlorine, methyl, methoxy or ethoxy, most preferably hydrogen, methyl, methoxy or ethoxy.

Examples of ring D, substituted by $R^{21}$ and/or $R^{22}$, are 2-methoxypyridine-3-yl, 2-ethoxypyridine-3-yl, 2-hydroxypyridine-3-yl, 2,4-dimethoxypyrimidine-5-yl, 2,6-dimethoxypyridine-3-yl, 3-methoxypyridine-2-yl, 3-methoxypyridine-4-yl, 4-methoxypyridine-3-yl, 3-methoxypyrazine-2-yl, 3-methylthiophen-2-yl, 3-methylpyridin-2-yl, pyridin-2-yl or 6-chlor-2-methoxypyridin-3-yl, preferably 2-methoxypyridine-3-yl, 2-ethoxypyridine-3-yl, 2,4-dimethoxy-pyrimidine-5-yl or 2,6-dimethoxypyridine-3-yl, and more preferably 2-methoxypyridine-3-yl.

In case of $R^{21}$ or $R^{22}$ being OH, the resultant substituted ring D may predominantly be present in form of its tautomer like, for example, 1,2-dihydro-2-oxopyridine-3-yl.

Ring G is preferably selected from the group consisting of thiophene, furan, pyrrole, pyrazole, isoxazole, pyridine, pyrimidine, quinoline, isoquinoline, tetrahydroisoquinoline, benzothiophene, benzofuran, indole, imidazole, thiazole, imidazothiazole, benzooxazine and quinoxaline.

In a particularly preferred embodiment ring G is selected from the group consisting of imidazole, pyridine, thiophene, benzothiophene and quinoline.

Even more preferably, ring G is selected from

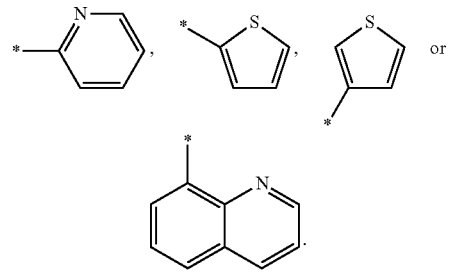

In a further preferred embodiment $R^{71}$ and $R^{72}$ are selected independently of one another from the group consisting of $C_1$-$C_4$-alkyl, O—$C_1$-$C_4$-alkyl, chlorine and bromine. Particularly, $R^{71}$ and $R^{72}$ are independently of one another methyl, methoxy, chlorine or bromine.

In a further particularly preferred embodiment ring G is

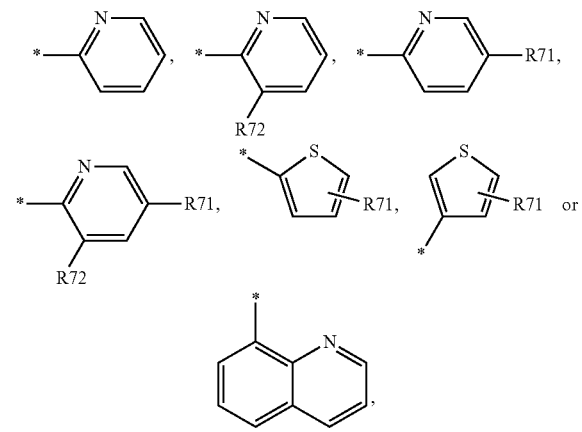

wherein $R^{71}$ is methyl, methoxy, chlorine or bromine, and $R^{72}$ is methyl.

In preferred embodiments of the compounds of formulae (I), (II) or (III), $R^3$ is selected from the group consisting of hydrogen, $C_{1-4}$-alkyl, $C_{2-4}$-alkenyl, $C_{2-4}$-alkynyl, O—$C_{1-4}$-alkyl, fluorine, chlorine, bromine, iodine, CN, $CF_3$ and $OCF_3$. More preferably, $R^3$ is selected from the group consisting of methyl, methoxy, fluorine, chlorine, bromine, iodine, CN and $OCF_3$.

Furthermore, in the compounds of formulae (I), (II) or (III) $R^3$ is preferably present in position 5 of the oxindole ring:

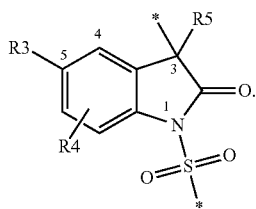

$R^4$ is in the compounds of formulae (I), (II) or (III) preferably hydrogen.

First Preferred Embodiment of $R^5$ in the Compounds of Formulae (I), (II) or (III):

According to this preferred embodiment, $R^5$ is a radical (W)—(X)—(Y)—Z as defined in the compounds of formulae (I), (II) or (III) wherein at least one, preferably two, more preferably three and particularly all of W, X, Y and Z have the following definition:

W is $NR^{54}$—($C_1$-$C_4$-alkylen);
X is CO;
Y is a bond; and/or
Z is E, O—$R^{52}$ or $NR^{51}R^{52}$.

A preferred combination of W, X, Y and Z results in a group $R^5$ having the following definition:

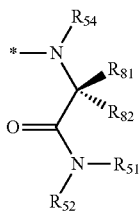

wherein
$R^{81}$ is hydrogen or $C_1$-$C_3$-alkyl, preferably methyl,
$R^{82}$ is hydrogen or $C_1$-$C_3$-alkyl, preferably hydrogen or methyl,
and $R^{81}$ and $R^{82}$ contain together up to 3 carbon atoms,
E is a saturated monocyclic ring having a maximum of 8, preferably a maximum of 6 and particularly 4 or 5 carbon atoms and 0 to 5, preferably 1 or 2 and particularly 1 nitrogen atom, and is preferably connected to the adjacent carbon atom of the carbonyl group via a nitrogen atom, and
$R^{51}$, $R^{52}$ and $R^{54}$ are as defined in the compounds of formulae (I), (II) or (III).

Preferably one, more preferably two and most preferably all of $R^{51}$, $R^{52}$ and $R^{54}$ have the following definition:
$R^{51}$ is hydrogen, $C_1$-$C_4$-alkyl, preferably methyl;
$R^{52}$ is hydrogen, $C_1$-$C_4$-alkyl, preferably methyl; and/or
$R^{54}$ is hydrogen or $C_1$-$C_4$-alkyl, preferably hydrogen or methyl, In a further preferred embodiment E is azetidine, piperazine, pyrrolidine, piperidine or morpholine.

Furthermore, particularly preferred are combinations of preferred embodiments of the above defined groups in the first preferred embodiment of $R^5$.

Second Preferred Embodiment of $R^5$ in the Compounds of Formulae (I), (II) or (III):

According to this preferred embodiment, $R^5$ is a radical (W)—(X)—(Y)—Z as defined in the compounds of formulae (I), (II) or (III) wherein at least one, preferably two, more preferably three and particularly all of W, X, Y and Z have the following definition:

W is a bond;
X is a bond;
Y is a bond; and/or
Z is E.

Preferably, E is a saturated or partially unsaturated monocyclic ring having a maximum of 8, preferably a maximum of 6 and particularly 4 or 5 carbon atoms, and 0 to 3, preferably 1 or 2 and particularly 1 nitrogen atom.

In a further preferred embodiment E is azetidine, piperazine, pyrrolidine or piperidine.

In a further preferred embodiment E is piperidine bonded to Z via the ring nitrogen atom.

In one preferred embodiment E is unsubstituted.

In another preferred embodiment E is substituted by one or two radicals $R^{53}$, with $R^{53}$ being defined as in the compounds of formulae (I), (II) or (III). More preferably $R^{53}$ is fluorine, OH, $C_1$-$C_4$-alkyl, O—$C_1$-$C_4$-alkyl or CN, more preferably fluorine, OH, methyl or methoxy and most preferably fluorine or OH. In a further preferred embodiment E is substituted by two radicals $R^{53}$ in geminal position, particularly with $R^{53}$ being fluorine. In a further preferred embodiment E is substituted by one radical $R^{55}$ as defined in the compounds of formulae (I), (II) or (III). More preferably $R^{55}$ is phenyl, O-phenyl or O-benzyl.

Furthermore, E is preferably substituted by one radical $R^{56}$ as defined in the compounds of formulae (I), (II) or (III) wherein at least one, preferably two and particularly all of $Q^1$, $Q^2$ and $Q^3$ have the following definition:
$Q^1$ is CO,
$Q^2$ is a bond, and/or
$Q^3$ is a saturated or partially unsaturated monocyclic ring having a maximum of 8, preferably a maximum of 6 and particularly 4 or 5 carbon atoms and 0 to 5, preferably 1 or 2 and particularly 1 nitrogen atom and is preferably connected to $Q^2$ via a nitrogen atom.

In a further preferred embodiment $Q^3$ is azetidine, piperazine, pyrrolidine, piperidine or morpholine.

Moreover, E is preferably substituted by one radical $R^{57}$ as defined in the compounds of formulae (I), (II) or (III). More preferably $R^{57}$ is CO—$N(C_1$-$C_4$-alkyl)$_2$ or CO—O—$C_1$-$C_4$-alkyl, and in particular CO—$N(CH_3)_2$.

Preferred combinations of W, X, Y, Z, $R^{53}$, $R^{55}$ and/or $R^{57}$ result in groups $R^5$ having the following definition:

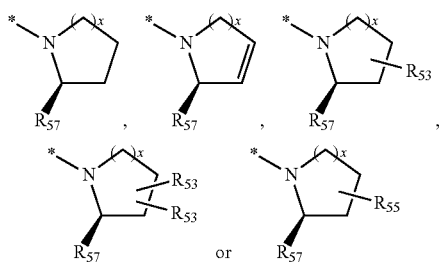

wherein
x is 1 or 2.

More preferred combinations of W, X, Y, Z, $R^{53}$ and/or $R^{57}$ result in groups $R^5$ having the following definition:

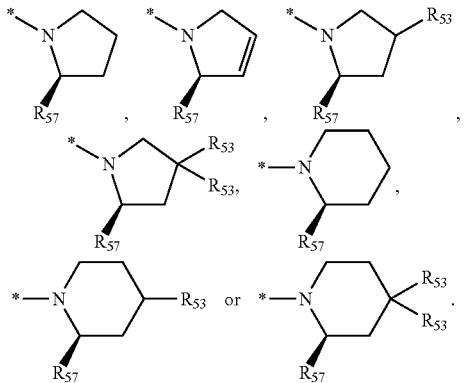

Particularly preferred combinations of W, X, Y, Z, $R^{53}$ and/or $R^{57}$ result in groups $R^5$ having the following definition:

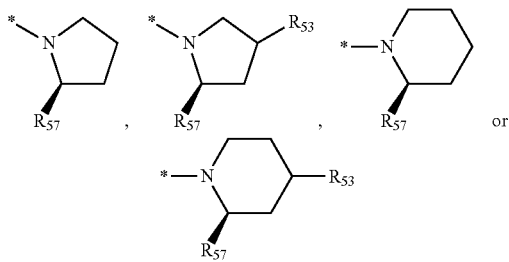

Furthermore, particularly preferred are combinations of preferred embodiments of the above defined groups in the second preferred embodiment of $R^5$.

In a further preferred embodiment a compound of the formula (I), (II) or (III) is disclosed, wherein E is pyrrolidine bonded to Z via the ring nitrogen atom, with $R^{53}$ at position C-4 and selected from the group consisting of fluorine, OH, $C_1$-$C_4$-alkyl, O—$C_1$-$C_4$-alkyl or CN, and with $R^{56}$ at position C-2 selected from the group consisting of hydrogen, $C_1$-$C_6$-alkyl, phenyl, $C_1$-$C_4$-alkylen-phenyl, COOH, CO—O—$C_1$-$C_4$-alkyl, CONH$_2$, CO—NH—$C_1$-$C_4$-alkyl, CO—N($C_1$-$C_4$-alkyl)$_2$, CO—$C_1$-$C_4$-alkyl, CH$_2$—NH$_2$, CH$_2$—NH—$C_1$-$C_4$-alkyl and CH$_2$—N($C_1$-$C_4$-alkyl)$_2$.

Third Preferred Embodiment of $R^5$ in the Compounds of Formulae (I), (II) or (III):

According to this preferred embodiment, $R^5$ is a radical (W)—(X)—(Y)—Z as defined in the compounds of formulae (I), (II) or (III) wherein at least one, preferably two, more preferably three and particularly all of W, X, Y and Z have the following definition:

W is O, CH$_2$, NR$^{54}$ or NR$^{54}$(C$_1$-C$_4$-alkylen), preferably O or NH;
X is CO;
Y is a bond; and/or
Z is E.

Preferably, E is a saturated or partially unsaturated monocyclic ring having a maximum of 8, preferably a maximum of 6 and particularly 4 or 5 carbon atoms, and 0 to 3, preferably 1 or 2 nitrogen atoms.

More preferably E is selected from the group consisting of

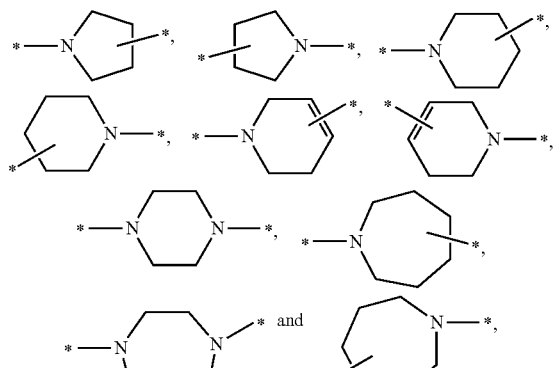

even more preferably from the group consisting of

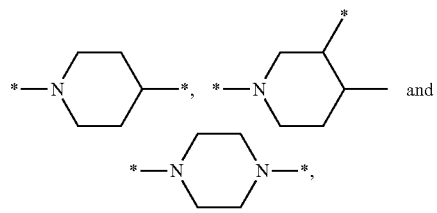

and most preferably E is

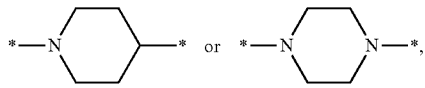

wherein one bond '—*' defines the bonding position to group Y and the second bond '—*' defines the bonding position to an optional substituent $R^{56}$.

Further, according to one embodiment E is

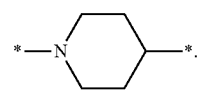

Moreover, according to another embodiment E is

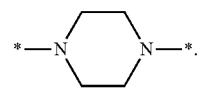

Preferably, E is substituted by $R^{56}$ as defined in compounds of formulae (I), (II) or (III), wherein at least one, preferably two and particularly all of $Q^1$, $Q^2$ and $Q^3$ have the following definition:
$Q^1$ is a bond,
$Q^2$ is a bond,
$Q^3$ is a unsaturated, saturated or partially unsaturated monocyclic ring having a maximum of 8, preferably 6 and particularly 4 or 5 carbon atoms, 0 to 5 and preferably 1 or 2 nitrogen atoms, 0 to 2 and preferably 0 or 1 oxygen atoms, and 0 to 2 and preferably 0 or 1 sulfur atom.

Preferably, $Q^3$ is substituted by $R^{63}$ as defined in compounds of formulae (I), (II) or (III).

$R^{63}$ is preferably $C_1$-$C_4$-alkyl and particularly methyl.

More preferably, $Q^3$ is selected from the group consisting of

[chemical structures]

and even more preferably from the group consisting of

[chemical structures]

Still more preferably $Q^3$ is

[chemical structures]

According to one embodiment $Q^3$ is

[chemical structure]

According to another embodiment $Q^3$ is

[chemical structure]

Particularly preferred are combinations of W, X, Y, Z and $R^{63}$ resulting in the following groups $R^5$:

[chemical structures]

Furthermore, particularly preferred are combinations of preferred embodiments of the above defined groups in the third preferred embodiment of $R^5$.

Particularly preferred are compounds of formula (I) wherein at least two and most preferably all of A, $R^3$, $R^4$, $R^5$, $R^6$ and $R^7$ are defined according to above described preferred embodiments of these groups.

Particularly preferred are further compounds of formula (II) wherein at least two and most preferably all of B, $R^3$, $R^4$, $R^5$, $R^6$ and $R^7$ are defined according to above described preferred embodiments of these groups.

Particularly preferred are moreover compounds of formula (III) wherein at least two and most preferably all of A, $R^3$, $R^4$, $R^5$, $R^6$ and $R^7$ are defined according to above described preferred embodiments of these groups.

The terms "alkyl", "alkylene", "alkenyl", "alkenylene", "alkynyl" and "alkynylene" as used herein always include unbranched or branched "alkyl", "alkylene", "alkenyl", "alkenylene", "alkynyl" or "alkynylene".

$C_1$-$C_4$-alkyl as used herein is preferably methyl, ethyl, n-propyl, i-propyl, n-butyl, sec-butyl or t-butyl.

$C_1$-$C_4$-alkylene as used herein is preferably methylene, ethylene, or branched or unbranched propylene or butylene.

$C_2$-$C_4$-alkenyl as used herein is preferably ethenyl, or branched or unbranched propenyl or butenyl.

$C_2$-$C_4$-alkenylene as used herein is preferably ethenylene, or branched or unbranched propenylene or butenylene.

$C_2$-$C_4$-alkynyl as used herein is preferably ethynyl, or branched or unbranched propynyl or butynyl.

$C_2$-$C_4$-alkynylene as used herein is preferably ethynylene, or branched or unbranched propynylene or butynylene.

$C_1$-$C_6$-alkyl as used herein is preferably branched or unbranched hexyl or pentyl, more preferably $C_1$-$C_4$-alkyl, and in particular methyl, ethyl, n-propyl, i-propyl, n-butyl, sec-butyl or t-butyl.

$C_1$-$C_6$-alkylene as used herein is preferably branched or unbranched hexylene or pentylene, more preferably $C_1$-$C_4$-alkylene, and in particular methylene, ethylene, or branched or unbranched propylene or butylene.

$C_2$-$C_6$-alkenyl as used herein is preferably branched or unbranched hexenyl or pentenyl, more preferably $C_2$-$C_4$-alkenyl, and in particular ethenyl, or branched or unbranched propenyl or butenyl.

$C_2$-$C_6$-alkenylene as used herein is preferably branched or unbranched hexenylene or pentenylene, more preferably $C_2$-$C_4$-alkenylene, and in particular ethenylene, or branched or unbranched propenylene or butenylene.

$C_2$-$C_6$-alkynyl as used herein is preferably branched or unbranched hexynyl or pentynyl, more preferably $C_2$-$C_4$-alkynyl, and in particular ethynyl, or branched or unbranched propynyl or butynyl.

$C_2$-$C_6$-alkynylene as used herein is preferably branched or unbranched hexynylene or pentynylene, more preferably $C_2$-$C_4$-alkynylene, and in particular ethynylene, or branched or unbranched propynylene or butynylene.

As used herein, "benzothiazole" means 2-, 3-, 4-, 5-, 6- or 7-benzothiazole, "pyrimidine" means 2-, 4-, 5-, or 6-pyrimidine, "pyridine" means 2-, 3-, 4-, 5- or 6-pyridine, "pyridazine" means 3-, 4-, 5- or 6-pyridazine, "pyrazine" means 2-, 3-, 5- or 6-pyrazine, "isoquinoline" means 1-, 3-, 4-, 5-, 6-, 7-, or 8-isoquinoline, "quinoline" means 2-, 3-, 4-, 5-, 6-, 7-, or 8-quinoline, "thiazole" means 2-, 4- or 5-thiazole, "benzimidazole" means 2-, 4-, 5-, 6- or 7-benzimidazole, "imidazole" means 2-, 4- or 5-imidazole, "benzoxazole" means 2-, 4-, 5-, 6- or 7-benzoxazole, "benzothiophene" means 2-, 3-, 4-, 5-, 6-, or 7-benzothiophene, "thiophene" means 2-, 3-, 4- or 5-thiophene, "benzofuran" means 2-, 3-, 4-, 5-, 6- or 7-benzofuran and "furan" means 2-, 3-, 4- or 5-furan.

Further, as used herein, "pyrrole" means 2-, 3-, 4- or 5-pyrrole, "tetrahydroquinoline" means 1-, 2-, 3-, 4-, 5-, 6-, 7- or 8-tetrahydroquinoline, "tetrahydroisoquinoline" means 1-, 2-, 3-, 4-, 5-, 6-, 7- or 8-tetrahydroisoquinoline, "dihydrobenzofuran" means 2-, 3-, 4-, 5-, 6- or 7-dihydrobenzofuran, "indole" means 1-, 2-, 3-, 4-, 5-, 6- or 7-indole, "dihydroisoindole" means 1-, 2-, 3-, 4-, 5-, 6- or 7-dihydroisoindole.

Further, as used herein, "pyrazole" means 1-, 3-, 4- or 5-pyrazole, "isoxazole" means 3-, 4- or 5-isoxazole, "imidazothiazole" means 2-, 4-, 5- or 6-imidazothiazole, "benzoxazine" means 2-, 3-, 4-, 5-, 6-, 7- or 8-benzoxazine, "quinoxaline" means 2-, 3-, 5-, 6-, 7- or 8-quinoxaline.

Further, as used herein, "azetidine" means 1-, 2-, 3- or 4-azetidine, "piperazine" means 1-, 2-, 3-, 4-, 5- or 6-piperazine, "pyrrolidine" means 1-, 2-, 3-, 4- or 5-pyrrolidine, "piperidine" means 1-, 2-, 3-, 4-, 5- or 6-piperidine and "morpholine" means 2-, 3-, 4-, 5- or 6-morpholine.

At each occurrence in the present application, the formulations "$NR^{54}$" and $CO-NR^{58}$ shall, particularly in a preferred embodiment, include $NHR^{54}$ and $CO-NHR^{58}$, respectively.

At each occurrence in the present application, the formulation "N(definition of residue)$_{number}$" (e.g. "$N(C_1-C_4-alkyl)_2$") shall, particularly in a preferred embodiment, be understood that each of the residues according to the given "number" may have independently of each other either the same or different meanings. For example, "$N(C_1-C_4-alkyl)_2$" shall represent "$N(C_1-C_4-alkyl)(C_1-C_4-alkyl)$" wherein both residues "$(C_1-C_4-alkyl)$" are each bonded to the nitrogen atom and may have either the same or different meanings.

At each occurrence in the present application, the formulation "E is an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, said ring may comprise up to two oxo groups, and may be substituted by radicals $R^{55}$, $R^{56}$, $R^{57}$, and/or up to three radicals $R^{53}$" shall, particularly as a preferred embodiment, have the meaning of "E is an unsaturated, saturated or partially unsaturated mono-, bi- or tricyclic ring having as ring members any of from 2 to (a maximum of) 14 carbon atoms and any of 0, 1, 2, 3, 4 and 5 nitrogen atoms, any of 0, 1 and 2 oxygen atoms and any of 0, 1 and 2 sulfur atoms, said ring comprising any of 0, 1 and 2 oxo groups and be optionally substituted at the ring carbon atom and/or ring nitrogen atom by from one to three radicals selected from the group consisting of $R^{55}$, $R^{56}$ and $R^{57}$, and with 1, 2 or 3 radicals $R^{53}$ which independently of each other may have either identical or different meanings, wherein E can be bonded to Y via a carbon ring atom or a nitrogen ring atom" and, more preferably, the meaning of "E is an unsaturated, saturated or partially unsaturated mono-, bi- or tricyclic ring having as ring members 2, 3, 4, 5, 6, 7, 8, 9, 10, 11, 12, 13 or a maximum of 14 carbon atoms and 0, 1, 2, 3, 4 or 5 nitrogen atoms, 0, 1 or 2 oxygen atoms and/or 0, 1 or 2 sulfur atoms, said ring comprise 0, 1 or 2 oxo groups and be optionally substituted at the ring carbon atom and/or ring nitrogen atom by radicals $R^{55}$, $R^{56}$ and/or $R^{57}$, and/or with 1, 2 or 3 radicals $R^{53}$ which independently of each other may have either identical or different meanings, wherein E can be bonded to Y via a carbon ring atom or a nitrogen ring atom".

At each occurrence in the present application, the formulation "$Q^3$ is a hydrogen or an unsaturated, saturated or partially unsaturated mono-, bi- or tricyclic ring having as ring members a maximum of 14 carbon atoms and 0 to 5 nitrogen atoms, 0 to 2 oxygen atoms and/or 0 to 2 sulfur atoms, which may comprise up to two oxo groups and may be substituted by the radicals $R^{63}$, $R^{64}$ and/or $R^{65}$" shall have, particularly as a preferred embodiment, the meaning of "$Q^3$ is a hydrogen or an unsaturated, saturated or partially unsaturated mono-, bi- or tricyclic ring having as ring members any from 2 to (a maximum of) 14 carbon atoms and any of 0, 1, 2, 3, 4 and 5 nitrogen atoms, and any of 0, 1 and 2 oxygen atoms and any of 0, 1 and 2 sulfur atoms, said ring may comprise any of 0, 1 and 2 oxo groups and may be substituted at the carbon ring atom and/or the nitrogen ring atom by the radicals $R^{63}$, $R^{64}$ and/or $R^{65}$ which independently of each other may have either identical or different meanings, wherein $Q^3$ can be bonded to $Q^2$ via a carbon ring atom or a nitrogen ring atom" and, more preferably, the meaning of "$Q^3$ is a hydrogen or an unsaturated, saturated or partially unsaturated mono-, bi- or tricyclic ring having as ring members any of from 2, 3, 4, 5, 6, 7, 8, 9, 10, 11, 12, 13 and 14 carbon atoms and any of 0, 1, 2, 3, 4 and 5 nitrogen atoms, and any of 0, 1 and 2 oxygen atoms and any of 0, 1 and 2 sulfur atoms, said ring may comprise any of 0, 1 and 2 oxo groups and may be substituted at the carbon ring atom and/or nitrogen ring atom by the radicals $R^{63}$, $R^{64}$ and/or $R^{65}$ which independently of each other may have either identical or different meanings, wherein $Q^3$ can be bonded to $Q^2$ via a carbon ring atom or a nitrogen ring atom".

At each occurrence in the present application, the formulation "where the heterocycles are 5- or 6-membered rings and comprise up to 4 heteroatoms selected from the group consisting of N, O and S, and up to 2 oxo groups, where not more than one of the heteroatoms is an oxygen atom" shall have, particularly as a preferred embodiment, the meaning of "where the heterocycles as forming part of the heteromonocyclic or heterobicyclic ring are 5- or 6-membered rings and per heteromonocyclic or heterobicyclic ring may comprise any of 1, 2, 3 and 4 heteroatoms which independently of each other are selected from the group consisting of N, O and S, said heterocycles may further comprise any of 0, 1 and 2 oxo groups, whereby not more than one of the heteroatoms is an oxygen atom".

At each occurrence in the present application, the formulation "where the heterocycles are 5- or 6-membered rings and comprise 2 to 4 heteroatoms selected from the group consisting of N, O and S, and up to 2 oxo groups" shall have, particularly as a preferred embodiment, the meaning of "where the heterocycles as forming part of the heteromonocyclic or heterobicyclic ring are 5- or 6-membered rings and per heteromonocyclic or heterobicyclic ring may comprise any of 2, 3 and 4 heteroatoms which independently of each other are selected from the group consisting of N, O and S, said heterocycles may further comprise any of 0, 1 and 2 oxo groups".

At each occurrence in the present application, the formulation "where the heterocycles are 5- or 6-membered rings and comprise up to 4 heteroatoms selected from the group consisting of N, O and S, and up to 2 oxo groups" shall have, particularly as a preferred embodiment, the meaning of "where the heterocycles as forming part of the heteromonocyclic or heterobicyclic ring are 5- or 6-membered rings and per heteromonocyclic or heterobicyclic ring may comprise any of 1, 2, 3 and 4 heteroatoms which independently of each other are selected from the group consisting of N, O and S, said heterocycles may further comprise any of 0, 1 and 2 oxo groups".

At each occurrence in the present application, in a preferred embodiment the residue $R^3$ is placed at position C-5 of the 1,3-dihydroindol-2-one and selected from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, $NH(C_1$-$C_4$-alkyl) and $N(C_1$-$C_4$-alkyl)$_2$ and $R^4$ is hydrogen.

The formulation "partially aromatic" as used herein means an aromatic system comprising two or more double bonds wherein at least one of said double bonds has been hydrogenated by addition of hydrogen, whereby the remaining one or more double bounds may be either standing alone (in case of one double bound only), conjugated, partially conjugated or no longer conjugated with each other.

The formulation the "[said] ring may comprise up to two oxo groups" as used herein means that said ring has up to two carbon atoms which are each connected to an oxygen atom via a double bond.

Divalent radicals are to be read from the left to the right with respect to their bonds to other substructures of the molecule. Thus, for example "CO—$NR^{58}$" in the definition of X in $R^5$ of the compound of formulae (I) to (IIII) is connected to W and Y as follows: (W)—CO—$N(R^{58})$—(Y)—Z.

By prodrugs are meant those compounds which are metabolized in vivo to the compounds of the invention. Typical examples of prodrugs are described in C. G. Wermuth (ed.): The Practice of Medicinal Chemistry, Academic Press, San Diego, 1996, p. 671-715. These include, for example, phosphates, carbamates or amino acids, esters and others.

The invention further relates to the physiologically tolerated salts of the compounds of the invention which can be obtained by reacting the compounds of the invention with a suitable acid or base. Suitable acids and bases are listed for example in Fortschritte der Arzneimittelforschung, 1966, Birkhäuser Verlag. vol. 10, pages 224-285. These include for example hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and 2-amino-2-(hydroxymethyl)-1,3-propanediol (Tris).

The invention further relates to the compound of any of general formulae (I) to (III) as therapeutic or prophylactic agent.

Furthermore, the invention relates to a medicament comprising the compound of any of general formulae (I) to (III).

The compound of any of general formulae (I) to (III) can be used for producing a medicament for the control and/or prophylaxis of various vasopressin-dependent or oxytocin-dependent diseases.

The invention further relates to the use of the compound of any of general formulae (I) to (III) for the control and/or prophylaxis of various vasopressin-dependent or oxytocin-dependent diseases.

A further aspect of the invention is a method for the therapeutic and/or prophylactic treatment of a mammal requiring a treatment by administering the compound of any of formulae (I) to (III) for the treatment of diseases.

Furthermore, the compound of any of formulae (I) to (III) can be used for the treatment of:
depressions and/or bipolar disorders such as, for example, dysthymic disorders, subsyndromal depression, seasonal affected disorders, premenstrual dysphoric disorders and/or psychotic disorders;
anxiety and/or stress-related disorders such as, for example, general anxiety disorders, panic disorders, obsessive-compulsive disorders, post-traumatic disorders, acute stress disorders and/or social phobia;
memory disorders and/or Alzheimer's disease;
psychoses and/or psychotic disorders; and/or
Cushing's syndrome.

The compounds of the invention are effective after administration in various ways, especially orally.

The compounds according to the present invention can be useful for the treatment or prevention of various vasopressin-dependent or oxytocin-dependent complaints, such as mental disorders. Examples of such mental disorders according to the American Psychiatric Association DSM-IV, Diagnostic and Statistical Manual of Mental Disorders, 4th ed., 1994 are attention-deficit and disruptive behavior disorders; delirium, dementia, and amnestic and other cognitive disorders; substance-related disorders, such as alcohol use disorders and alcohol-induced disorders; schizophrenia and other psychotic disorders, such as schizophrenia, schizophreniform disorder, schizoaffective disorder and delusional disorder; mood disorders, such as depressive disorders (major depressive disorder, dysthymic disorder, seasonal affective disorder, premenstrual dysphoric disorder, depressive disorder not otherwise specified), bipolar disorder (bipolar I disorder, bipolar II disorder, cyclothymic disorder, bipolar disorder not otherwise specified, substance-induced mood disorder, mood disorder not otherwise specified); stress-related disorders, such as acute stress disorder; anxiety disorders, such as panic disorder without agoraphobia, panic disorder with agoraphobia, agoraphobia without history of panic disorder, specific phobia, social phobia, obsessive-compulsive disorder, posttraumatic stress disorder, acute stress disorder, generalized anxiety disorder, substance-induced anxiety disorder; somatoform disorders, such as somatization disorder, undifferentiated somatoform disorder, conversion disorder, pain disorder; eating disorders; sleep disorders, such as primary sleep disorders (dyssomnias, parasomnias), sleep disorders related to another mental disorder. Furthermore, compounds according to the present invention can be useful for the treatment of Cushing syndrome.

The present invention also relates to pharmaceutical compositions which comprise an effective dose of a compound of the invention or of a pharmaceutically acceptable salt thereof and suitable pharmaceutical carriers.

These pharmaceutical carriers are chosen according to the pharmaceutical form and the desired mode of administration.

With the pharmaceutical compositions of the present invention for oral, sublingual, subcutaneous, intramuscular, intravenous, topical, intratracheal, intranasal, transdermal or rectal administration it is possible to administer the compounds of the formula (I), (II) or (III) or, where suitable, the salts thereof to animals or humans in unitary administration forms, mixed with conventional pharmaceutical carriers, for the prophylaxis or treatment of the above disorders or diseases.

The suitable unitary administration forms include forms for oral administration, such as tablets, gelatin capsules, powders, granules and solutions or suspensions for oral intake, forms for sublingual, buccal, intratracheal or intranasal administration, aerosols, implants, forms for subcutaneous, intramuscular or intravenous administration and forms for rectal administration.

For topical administration, the compounds of the invention can be used in creams, ointments or lotions.

In order to achieve the desired prophylactic or therapeutic effect, the dose of the basic active ingredient may vary between 0.01 and 50 mg per kg of bodyweight and per day.

Each unit dose may comprise from 0.05 to 5 000 mg, preferably 1 to 1 000 mg, of the active ingredient in combination with a pharmaceutical carrier. This unit dose may be administered 1 to 5 times a day so that a daily dose of from 0.5 to 25 000 mg, preferably 1 to 5 000 mg, is administered.

If a solid composition is prepared in the form of tablets, the main ingredient is mixed with a pharmaceutical carrier such as gelatin, starch, lactose, magnesium stearate, talc, silica or the like.

The tablets may be coated with sucrose, a cellulose derivative or another suitable substance or treated otherwise in order to display persistent or delayed activity and in order to release a predetermined amount of the basic active ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable color.

The water-dispersible powders or granules may comprise the active ingredients mixed with dispersants or wetting agents, or suspending agents, such as polyvinylpyrrolidones, and sweeteners or masking flavors.

Rectal administration is achieved by using suppositories which are prepared with binders which melt at the rectal temperature, for example cocoa butter or polyethylene glycols. Parenteral administration is effected by using aqueous suspensions, isotonic salt solutions or sterile and injectable solutions which comprise pharmacologically acceptable dispersants and/or wetting agents, for example propylene glycol or polyethylene glycol.

The basic active ingredient may also be formulated as microcapsules or liposomes, if suitable with one or more carriers or additives.

In addition to the compounds of the general formula (I) or their pharmaceutically acceptable salts, the compositions of the invention may comprise other basic active ingredients which may be beneficial for the treatment of the abovementioned disorders or diseases.

The present invention thus further relates to pharmaceutical compositions in which a plurality of basic active ingredients are present together, where one of these is the compound of the invention.

The compounds of the invention were tested for their activity in the following vasopressin V1b receptor binding assay.

Vasopressin V1b Receptor Binding Assay

The binding of the compounds of this invention to the vasopressin V1b receptor was determined with the following assay:

Dissolution of Compounds

Compounds were dissolved in a concentration of $10^{-2}$ M or $10^{-3}$ M in DMSO. Further dilutions were performed with water Binding Assays The procedure for the binding assay was based on the method of Tahara et al. (Tahara A et al., *Brit. J. Pharmacol.* 125, 1463-1470 (1998)). Assays (0.250 ml) consisted of membranes (58 µg protein) from CHO-K1 cells permanently expressing human V1b receptors (preparation V1b-3H2, containing protease inhibitors, Roche complete Mini #1836170), 1.5 nM $^3$H-AVP (8-Arg-vasopressin, NET 800) in incubation buffer (total binding) and different concentrations of test compound (displacement). Non-specific binding was defined with $10^{-6}$ M AVP. Assays were performed in triplicate.

Incubation buffer: 50 mM Tris, 10 mM $MgCl_2$, 0.1% BSA adjusted to pH 7.4 with HCl.

After incubation, 60 min at room temperature, bound and free radioligand was separated by filtration under vacuum through Whatman GF/B glass fibre mats using a Skatron cell harvester 7000.

Liquid scintillation counting was performed in beta-counters, Tricarb model 2000 or 2200CA (Packard). Dpm were calculated by a programme with standardisation using a standard quench series.

Evaluation

Evaluation of binding parameters was performed by non-linear regression analysis with SAS. The strategy of this program is similar to the program LIGAND described by Munson and Rodbard (Munson P J and Rodbard D, *Analytical Biochem* 107, 220-239 (1980)).

The compounds of the invention bind to the vasopressin V1b receptor. In the following Table 1 the binding affinity of selected examples for the vasopressin V1b receptor is shown.

TABLE 1

Binding affinity of selected examples for the vasopressin V1b receptor

| Example # | Binding affinity for the vasopressin V1b receptor |
|---|---|
| 2 | +++ |
| 3 | +++ |
| 5 | +++ |
| 6 | ++ |
| 9 | +++ |
| 10 | +++ |
| 13 | +++ |
| 28 | +++ |
| 29 | +++ |
| 31 | +++ |
| 32 | ++ |
| 33 | ++ |
| 47 | +++ |
| 48 | +++ |
| 51 | +++ |
| 52 | +++ |
| 53 | +++ |
| 56 | +++ |
| 59 | + |
| 63 | + |
| 65 | ++ |
| 75 | +++ |
| 76 | +++ |
| 82 | +++ |

TABLE 1-continued

Binding affinity of selected examples for the vasopressin V1b receptor

| Example # | Binding affinity for the vasopressin V1b receptor |
|---|---|
| 83 | +++ |
| 103 | +++ |
| 104 | +++ |
| 105 | +++ |
| 107 | +++ |
| 113 | +++ |
| 115 | +++ |
| 122 | ++ |
| 123 | ++ |
| 125 | +++ |
| 126 | +++ |
| 127 | +++ |
| 130 | +++ |
| 134 | +++ |
| 136 | +++ |
| 143 | +++ |
| 145 | +++ |
| 154 | +++ |
| 158 | +++ |
| 165 | ++ |
| 166 | ++ |
| 168 | +++ |
| 169 | ++ |
| 170 | ++ |
| 171 | +++ |
| 172 | ++ |
| 220 | +++ |
| 221 | +++ |
| 222 | +++ |
| 224 | +++ |
| 225 | ++ |
| 226 | ++ |
| 227 | +++ |
| 230 | +++ |
| 232 | +++ |
| 234 | +++ |
| 236 | +++ |
| 237 | +++ |
| 238 | +++ |
| 239 | +++ |
| 240 | +++ |
| 241 | ++ |
| 242 | +++ |
| 243 | +++ |
| 245 | +++ |
| 246 | +++ |
| 247 | +++ |
| 248 | +++ |
| 252 | +++ |
| 253 | +++ |
| 255 | ++ |
| 256 | +++ |
| 270 | +++ |
| 277 | ++ |
| 280 | +++ |
| 281 | ++ |
| 282 | +++ |
| 286 | ++ |
| 288 | +++ |
| 289 | +++ |

+ indicates binding affinity >500 nM
++ indicates binding affinity between 50 and 500 nM
+++ indicates binding affinity <50 nM Functional Assay for the Human $V_{1b}$ Receptor Functional activity was determined by testing the effect of the compounds on calcium release in CHO-K1 cells stably transfected with human $V_{1b}$ receptor. Cells were seeded into 96-well plates at 50,000 cells/well and grown overnight in tissue culture medium (DMEM/Nut mix F12 Medium with Glutamax I (Invitrogen), containing 10% FCS, 100 units/ml Penicillin, 100 μg/ml Streptomycine, 800 μg/ml Geneticin) at 37° C. and 5% $CO_2$. Cells were loaded with a fluorescent calcium-sensitive dye in the presence of 1% probenicid according to the manufacturers protocol ($Ca^{++}$-Plus-Assay Kit, Molecular Devices). Serial compound dilutions (final concentrations $10^{-10}$ to $10^{-5}$ M) were added to the cells either alone or in the presence of Arg-vasopressin ($10^{-8}$M) and the maximum calcium response was determined using a FLIPR-96 instrument (Molecular Devices). Concentration-response curves were fitted using a three-parameter logistic equation (GraphPad Prism). Kb values were calculated from IC50 values according to Cheng & Prusoff (Kb=IC50/(1+L/EC50)).

Antidepressant Effects of Compounds of this Invention in the Rat Forced Swim Model The potential antidepressant effects of some examples of this invention were examined in the rat forced swim test. When rats are forced to swim in a cylinder from which no escape is possible they readily adopt a characteristic immobile posture and make no further attempts to escape except for small movements needed to keep floating. The immobility is considered to reflect a 'depressive mood' (Porsolt R D, LePichon M, Jalfre M (1977). Depression: a new animal model sensitive to antidepressant treatment. *Nature* 266, 730-732.), in which animals cease to struggle to escape the aversive situation. The immobility induced by the procedure is influenced by a wide variety of antidepressants (Porsolt R D, Lenegre A, McArthur R A (1991). Pharmacological models of depression. In: Animal models in Psychopharmacology. B. Olivier, J. Mos, J. L. Slangen (eds) Birkhauser Verlag, Basel, pp. 137-159.) and has a good predictive validity in that it detects antidepressants with different mechanisms of action. Administration of antidepressants such as fluoxetine increases the time an animal struggles (decreases the immobility time) when forced to swim in a confined space. Lack of struggling is thought to represent a state of despair.

Procedure:

Male Sprague Dawley rats (Janvier) weighing 160-200 gram (n=6) were placed individually into a glass water tank (40 cm×21.5 cm) filled with tap water (25° C.) up to 18 cm. This pre-test lasted for 15 min. Twenty-four hours later, animals were re-tested for 5 min in the same water tank while the total immobility time, swimming time and climbing time were recorded. Rats were considered immobile when they made no further attempts to escape, except for movements necessary to keep their heads above water (Porsolt R D, Anton G, Blavet N & Jalfre M. (1978). Behavioural despair in rats: a new model sensitive to anti-depressant treatments. *European Journal of Pharmacology* 47, 379-391). The absence of hind limb movements was recorded as immobility using a stopwatch by a single observer. The water in the bath was changed after each trial. Drugs were administered via intraperitoneal route as suspensions in hydroxypropylmethylcellulose (HPMC) three times before re-testing (for example 24, 4 and 0.5 hours before re-testing, depending on the test compound).

Some of the compounds of the invention, when tested in the rat forced swim model, yielded results strongly suggestive of antidepressant activity. The compounds of Examples 5 and 29 decreased the immobility time in a dose-dependent manner with an ED50 of <30 mg/kg. In comparison, SSR149415 (Griebel et al., PNAS 99, 6370 (2002)), an antidepressant-like compound that is structurally related to some compounds of this invention, showed an ED50 value of >30 mg/kg in our rat forced swim model.

These data show that subtle changes, such as replacing the 2-methoxy-phenyl group in SSR149415 with a 2-methoxy-pyridin-3-yl group or replacing the 2,4-dimethoxy-benzene-sulfonyl moiety with a thiophene-2-sulfonyl moiety, can lead to compounds having significantly enhanced activity in the rat forced swim model. Lower ED50 values, in turn, are likely to result in lower doses being required to obtain antidepressant effects, thus offering the possibility of an improved therapeutic index.

The synthesis of the compounds of the invention is described below.

The 1,3-dihydroindol-2-ones of the invention can be prepared in various ways, as outlined in synthesis schemes 1-5.

SYNTHESIS SCHEME 1 (terminology according to claim 1)

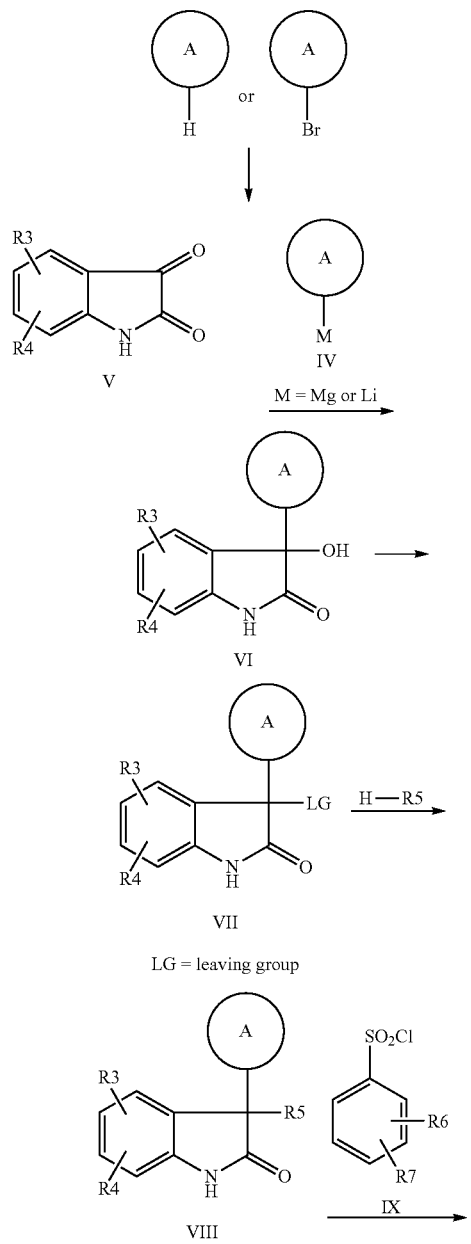

-continued

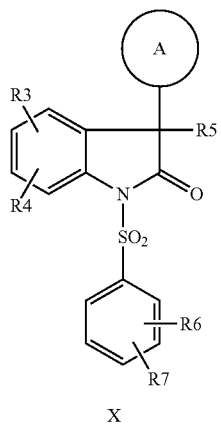

X

The 3-hydroxy-1,3-dihydroindol-2-ones VI can be obtained by addition of metalated heterocycles IV to the 3-keto group of isatins V. Examples of metalated heterocycles which can be employed are the corresponding magnesium and lithium compounds. The isatins V were either purchased or prepared by methods described in the literature (Advances in Heterocyclic Chemistry, A. R. Katritzky and A. J. Boulton, Academic Press, New York, 1975, 18, 2-58; J. Brazil. Chem. Soc. 12, 273-324 (2001)). The metalated heterocycles IV were prepared in various ways (see review article by G. Queguiner et al. in Advances in Heterocyclic Chemistry, Vol. 52, ed. A. R. Katritzky, Academic Press, 1991, 187-304.: J. Heterocyclic Chem. 37, 615 (2000); Heterocyles 37, 2149, (1994)): (i) reaction of heteroaryl halides with magnesium affords in certain cases (for example 2-bromo-3-methylthiophene) the corresponding Grignard compounds (M=Mg); (ii) reaction of heteroaryl bromides and iodides with alkyllithium reagents such as, for example, n-butyllithium, tert-butyllithium or mesityllithium at low temperatures affords in certain cases (for example 5-bromo-2,4-dimethoxypyrimidine) the lithiated heterocycles by halogen-lithium exchange; (iii) reaction of substituted heterocycles with the aforementioned alkyllithium reagents and lithium bases such as, for example, lithium diisopropylamide or lithium tetramethylpiperidylamide likewise affords in certain cases (for example 2-methoxypyrazine) the lithiated heterocycles, especially when the heteroaromatic system is substituted by ortho-directing groups such as, for example, a methoxy group.

The 3-hydroxy-1,3-dihydroindol-2-ones VI were converted in the next step into compounds VII which bear a leaving group LG in position 3. Examples for LG are halides, mesylate and tosylate. Thus, for example, in the case where LG is chlorine the intermediate VII can be prepared by treating the tertiary alcohol VI with thionyl chloride in the presence of a base such as, for example, pyridine. Alternatively, alcohols VI can be activated by conversion into the mesylate using methanesulfonyl chloride in the presence of a base such as, for example, triethylamine. The leaving group LG in the compounds VII can then be replaced by various nucleophiles R5-H, resulting in the compounds VIII which have the radical R5 in position 3. For example, replacement reactions with primary and secondary amines R5-H in the presence of a base such as, for example, N,N-diisopropylethylamine in a solvent such as, for example dichloromethane afford the analogous 3-amino-1,3-dihydroindol-2-ones VIII. The reaction is not confined to nitrogen nucleophiles; it is also possible for oxygen or sulfur nucleophiles R5-H, where appropriate after deprotonation with a suitable base such as, for example, sodium hydride. Final sulfonylation by treating the compounds VIII with the sulfonyl chlorides IX after deprotonation with a strong base such as, for example, potassium tert-butoxide or sodium hydride in a solvent such as, for example, DMF affords the compounds X of the invention.

SYNTHESIS SCHEME 2 (terminology according to claim 6)

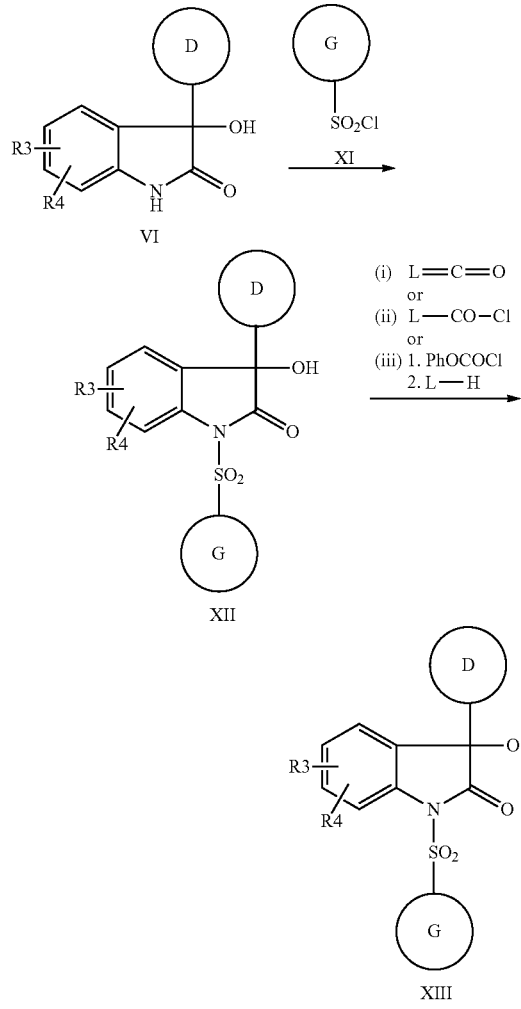

The 3-urethane derivatives XIII were prepared by initially reacting the 3-hydroxy-1,3-dihydroindol-2-ones VI with heterocyclic sulfonyl chlorides XI under the conditions already described above. Heterocyclic sulfonyl chlorides were either purchased or prepared by standard methods (see, for example, J. Med. Chem. 40, 1149 (1997); J. March, Advanced Organic Chemistry, 1992, 4th ed., Wiley, New York, p 724). The compounds XIII of the invention were prepared in various ways starting from the sulfonylated compounds XII: (i) reaction with isocyanates L=C=O (L contains nitrogen); (ii) reaction with carbamoyl chlorides L-CO—Cl (L contains nitrogen) in the presence of a base such as, for example, triethylamine; (iii) activation with phenyl chloroformate in the presence of a base such as, for example, pyridine and subsequent reaction of the carbonate intermediate with amines L-H, where appropriate at elevated temperature. Heteroaryl-substituted piperidines, that can be employed as amines L-H, can be prepared as described in Tetrahedron Lett. 34, 5287 (1993) and Bioorg. Med. Chem. Lett. 11, 2213 (2001) for 4-(4'-piperidinyl)-pyridine.

Compounds XXII of the invention bearing a functionalized nitrogen atom in position 3 (e.g. amides, sulfonamides, carbamates and ureas) were prepared as described in synthesis scheme 3. The 3-amino-1,3-dihydroindol-2-ones XX were prepared for example by reacting compounds VII (LG is a leaving group such as, for example, chloride or mesylate) with primary amines $R^{54}$—$NH_2$ in the presence of a base such as, for example, N,N-diisopropylethylamine in suitable solvents such as, for example, dichloromethane. Treatment of compounds XX with sulfonyl chlorides XI after deprotonation with a strong base such as, for example, potassium tert-butoxide or sodium hydride in a solvent such as, for example, DMF afforded the 3-amino-1,3-dihydroindol-2-ones XXI sulfonylated in position 1. The amino derivatives XXII of the invention were prepared from the amines XXI by reaction with customary reagents for derivatizing amino groups, such as, for example, carboxylic acids, carbonyl chlorides, carboxylic anhydrides, sulfonyl chlorides, chloroformates, isocyanates, carbamoyl chlorides by the relevant methods (J. March, Advanced Organic Chemistry, 1992, 4th ed., Wiley, New York, pp. 417-421; 499; 903).

N-heteroaryl-substituted piperidine carboxylic acids, that can be employed as coupling partner for the amines XXI, can be prepared for example as described in J. Med. Chem. 43, 2087 (2000) for 4-carboxy-N-(4-pyridyl)piperidine.

In addition, the 3-amino group in the compounds XXI can be substituted by treatment with alkylating agents such as, for example, alkyl bromides, iodides or mesylates, and by reaction with aldehydes or ketones in the presence of reducing agents such as, for example, sodium cyanoborohydride in the sense of a reductive amination (J. March, Advanced Organic Chemistry, 1992, 4th ed., Wiley, New York, p. 411; 898).

SYNTHESIS SCHEME 3 (terminology according to claim 6)

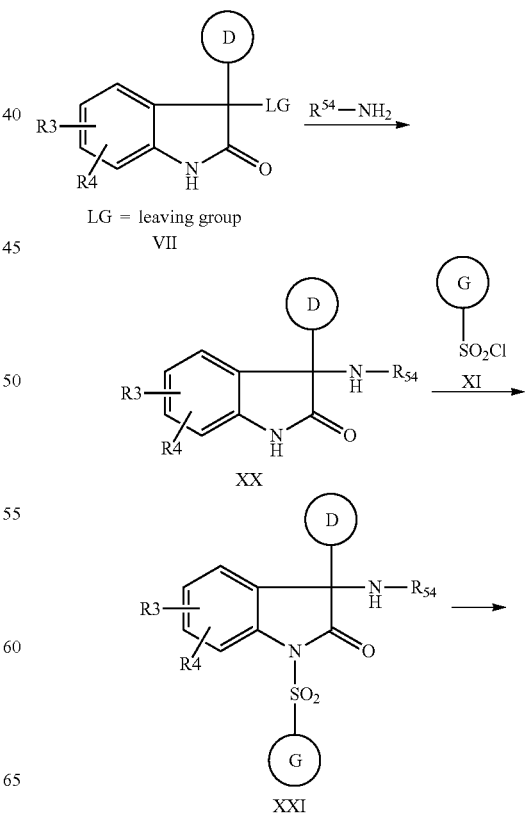

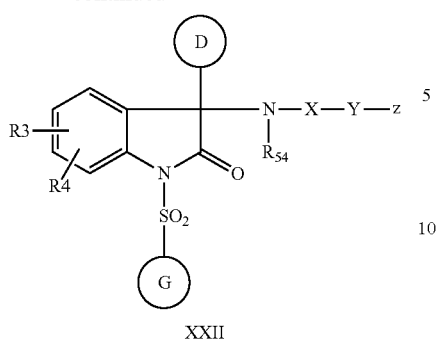

XXII

Compounds XXVII of the invention in which X—Y—Z radicals are linked via an alkylene bridge W to position 3 of the 1,3-dihydroindol-2-one framework were prepared for example by alkylation of the deoxygenated compounds XXIII and, where appropriate, derivatized further. An example for the preparation of compounds of the XXVII type in which W is a methylene group and X is a carbonyl group is described in synthesis scheme 4: Deoxygenation of the 3-hydroxy-1,3-dihydroindol-2-ones VI took place with triethylsilane in trifluoroacetic acid. The esters XXIV were prepared by alkylation of the 1,3-dihydroindol-2-ones XXIII with ethyl bromoacetate in the presence of bases such as, for example, potassium carbonate and, where appropriate, potassium iodide. After hydrolysis of the ester function, for example by treatment with lithium hydroxide in a water/THF/methanol mixture, the acids XXV were coupled with amines H—Y—Z employing relevant methods (J. March, Advanced Organic Chemistry, 1992, 4th ed., Wiley, New York, pp. 417-421). Final sulfonylation of the compounds XXVI with sulfonyl chlorides XI afforded the compounds XXVII of the invention.

SYNTHESIS SCHEME 4 (terminology according to claim 6)

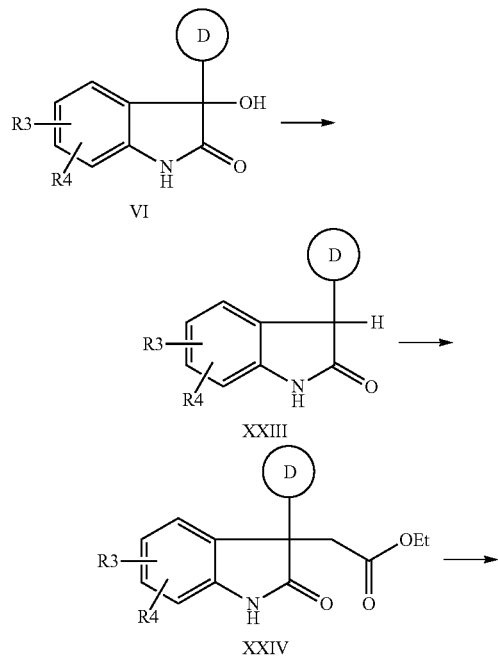

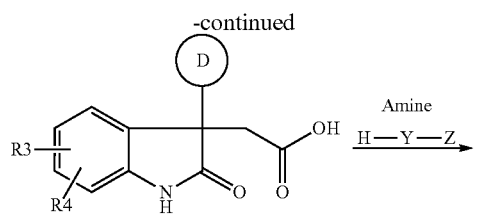

XXV

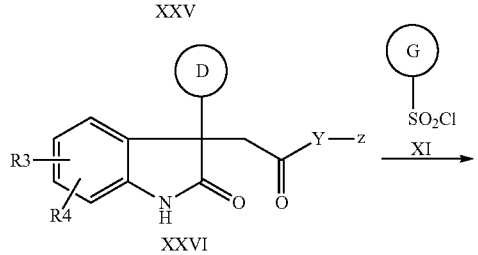

XXVI

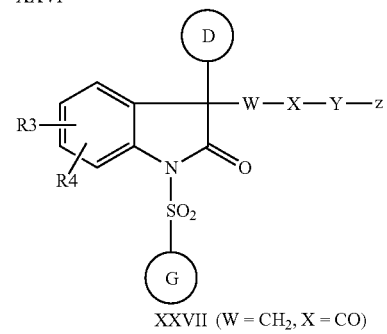

XXVII (W = CH₂, X = CO)

Compounds of the invention in which X—Y—Z radicals are linked via an oxygen atom (W=O) to position 3 of the 1,3-dihydroindol-2-one framework were prepared for example by alkylation of the 1-sulfonyl-3-hydroxy-1,3-dihydroindol-2-ones XII with alkylating agents such as, for example, aralkyl bromides, iodides or mesylates after deprotonation of the tertiary hydroxyl group with bases such as, for example, sodium hydride.

Enantiopure compounds can be obtained for example by carrying out a conventional racemic resolution using suitable optically active acids or bases with compounds of the invention or intermediates which comprise basic or acidic functional groups such as, for example, an amino or carboxyl group.

EXAMPLES (2S,4R)-4-Hydroxy-pyrrolidine-2-carboxylic acid dimethylamide hydrochloride A) BOP (172 g, 0.389 mol) was added in portions to a solution of (2S,4R)-1-(tert-butoxycarbonyl)-4-hydroxy-pyrrolidine-2-carboxylic acid (90 g, 0.398 mol) in dichloromethane (450 ml) and DIPEA (68 ml, 0.523 mol) at 0° C. and stirred at 0° C. for 1 hour. Then a 2 M solution of dimethylamine in THF (800 ml, 1.6 mol) was added dropwise at 0° C., and the mixture was stirred at room temperature overnight. The reaction mixture was stirred into ice-water, and the mixture was extracted several times with dichloromethane. The collected organic phase was washed with saturated brine, dried over magnesium sulfate and concentrated under reduced pressure.

B) The intermediate from step A was mixed with 500 ml of 5-6 M HCl in isopropanol and stirred at room temperature for 4 hours. After cooling to 0° C., the precipitate was filtered off, washed with isopropanol and diethyl ether and dried. 37 g of the desired product were obtained.

Example 1 and Example 2

(2S,4R)-1-[3-Benzothiazol-2-yl-5-chloro-1-(2,4-dimethoxy-benzenesulfonyl)-2-oxo-2,3-dihydro-1H-indol-3-yl]-4-hydroxy-pyrrolidine-2-carboxylic acid dimethylamide A) 3-Benzothiazol-2-yl-5-chloro-3-hydroxy-1,3-dihydroindol-2-one A 1.6 M solution of n-butyllithium in hexane (35 ml, 56 mmol) was added dropwise to a solution of benzothiazole (6.2 ml, 56 mmol) in THF (100 ml) at −78° C. After stirring at −78° C. for 1.5 h, the solution of the lithiated benzothiazole was transferred via a needle into an ice-cold suspension of 5-chloroisatin (3.63 g, 20 mmol) in THF (70 ml). The reaction mixture was stirred at 0° C. for 1 h and then saturated ammonium chloride solution was added. The mixture was extracted three times with ethyl acetate and the combined organic layers were washed with saturated brine. The organic phase was dried over magnesium sulfate, filtered and concentrated under reduced pressure, during which the intermediate starts to crystallize. Filtration and drying yielded 4.47 g of the intermediate as yellow crystalline solid.

B) 3-Benzothiazol-2-yl-3,5-dichloro-1,3-dihydroindol-2-one

Pyridine (0.57 ml) and thionyl chloride (0.42 ml) were successively added to an ice-cooled solution of the intermediate from step A (1.27 g, 4.0 mmol) in dichloromethane (40 ml). The reaction mixture was stirred at 0° C. for 1 h and then saturated ammonium chloride solution was added. The organic phase was dried over magnesium sulfate, filtered and concentrated under reduced pressure. The crude intermediate was rapidly employed without further purification in the next step.

C) (2S,4R)-1-(3-Benzothiazol-2-yl-5-chloro-2-oxo-2,3-dihydro-1H-indol-3-yl)-4-hydroxy-pyrrolidine-2-carboxylic acid dimethylamide (2S,4R)-4-hydroxy-pyrrolidine-2-carboxylic acid dimethylamide hydrochloride (0.78 g, 4.0 mmol) was added to a solution of the intermediate from step B in a mixture of dichloromethane (9 ml), THF (2 ml) and DIPEA (2 ml). The reaction mixture was stirred at room temperature for 48 h. After addition of water, the mixture was extracted four times with ethyl acetate. The combined organic layer was dried over magnesium sulfate, filtered and concentrated under reduced pressure. The less polar diastereomer, as judged by thin-layer-chromatography using 5% MeOH in dichloromethane, precipitated on concentration and was filtered off. Purification by chromatography (silica gel, 5% MeOH in dichloromethane) resulted in 0.28 g of the less polar diastereomer. Purification by chromatography (silica gel, 5% MeOH in dichloromethane) of the mother liquor resulted in 0.36 g of the more polar diastereomer.

Example 1

(2S,4R)-1-[3-Benzothiazol-2-yl-5-chloro-1-(2,4-dimethoxy-benzenesulfonyl)-2-oxo-2,3-dihydro-1H-indol-3-yl]-4-hydroxy-pyrrolidine-2-carboxylic acid dimethylamide, dextrorotatory diastereomer Sodium hydride (12 mg of 60% dispersion in mineral oil, 0.3 mmol) was added to an ice-cold solution of the less polar diastereomer intermediate from step C (115 mg, 0.25 mmol) in DMF (1.5 ml). The reaction mixture was stirred at 0° C. for 1 h and then 2,4-dimethoxy-benzene-sulfonyl chloride (71 mg, 0.3 mmol) was added. After the reaction mixture had been stirred at room temperature for one hour, water was added and the mixture was extracted with ethyl acetate. The organic layer was washed with water and saturated brine and dried over magnesium sulfate. Purification by chromatography (silica gel, 5% MeOH in dichloromethane) resulted in 93 mg of Example 1 as a white solid.

$^1$H NMR (400 MHz, DMSO-$d_6$) δ 8.15 (1H), 7.95 (1H), 7.75 (2H), 7.50 (3H), 7.20 (1H), 6.80 (1H), 6.75 (1H), 4.80 (1H), 4.25 (1H), 3.90 (3H), 3.85 (1H), 3.50 (3H), 3.25 (1H), 2.60 (3H), 1.85 (1H), 1.75 (1H); MS (API-ES, pos) m/z=657 [M+H]

Example 2

(2S,4R)-1-[3-Benzothiazol-2-yl-5-chloro-1-(2,4-dimethoxy-benzenesulfonyl)-2-oxo-2,3-dihydro-1H-indol-3-yl]-4-hydroxy-pyrrolidine-2-carboxylic acid dimethylamide, levorotatory diastereomer The diastereomer product was prepared by the method described in the previous paragraph starting from the more polar diastereomer intermediate from step C. Purification by chromatography (silica gel, 5% MeOH in dichloromethane) resulted in Example 2 as a white solid.

$^1$H NMR (400 MHz, DMSO-$d_6$) δ 8.10 (1H), 7.95 (1H), 7.75 (1H), 7.65 (1H), 7.45 (4H), 6.80 (1H), 6.75 (1H), 4.85 (1H), 4.70 (1H), 4.30 (1H), 3.90 (3H), 3.60 (1H), 3.40 (3H), 2.83 (1H), 2.55 (3H), 2.45 (3H), 2.10 (1H), 1.80 (1H); MS (API-ES, pos) m/z=657 [M+H]

Example 3 and Example 4

(2S,4R)-1-[5-Chloro-1-(2,4-dimethoxy-benzenesulfonyl)-3-(2,4-dimethoxy-pyrimidin-5-yl)-2-oxo-2,3-dihydro-1H-indol-3-yl]-4-hydroxy-pyrrolidine-2-carboxylic acid dimethylamide A) 5-Chloro-3-(2,4-dimethoxy-pyrimidin-5-yl)-3-hydroxy-1,3-dihydroindol-2-one A 1.6 M solution of n-butyllithium in hexane (10 ml, 16 mmol) was added dropwise to a solution of 5-bromo-2,4-dimethoxypyrimidine (3.29 g, 15 mmol) in THF (50 ml) at −78° C. After stirring at −78° C. for 0.5 h, a suspension of 5-chloroisatin (1.27 g, 7.0 mmol) in THF (50 ml) was added dropwise. The reaction mixture was allowed to warm to room temperature and then saturated ammonium chloride solution was added. The mixture was extracted three times with ethyl acetate, and the combined organic layers were washed with saturated brine. The organic phase was dried over magnesium sulfate, filtered and concentrated under reduced pressure. Purification by chromatography (silica gel, 50% ethyl acetate in dichloromethane) resulted in 0.97 g of the intermediate.

B) 3,5-Dichloro-3-(2,4-dimethoxy-pyrimidin-5-yl)-1,3-dihydroindol-2-one

Pyridine (0.28 ml) and thionyl chloride (0.18 ml) were added successively to an ice-cold solution of the intermediate from step A (0.64 g, 2.0 mmol) in dichloromethane (20 ml). The reaction mixture was stirred at 0° C. for 1 h and then saturated ammonium chloride solution was added. The organic phase was dried over magnesium sulfate, filtered and concentrated under reduced pressure. The crude intermediate was rapidly employed without further purification in the next step.

C) (2S,4R)-1-[5-Chloro-3-(2,4-dimethoxy-pyrimidin-5-yl)-2-oxo-2,3-dihydro-1H-indol-3-yl]-4-hydroxy-pyrrolidine-2-carboxylic acid dimethylamide (2S,4R)-4-Hydroxy-pyrrolidine-2-carboxylic acid dimethylamide hydrochloride (0.39 g, 2.0 mmol) was added to a solution of the intermediate from step B in a mixture of dichloromethane (4 ml), THF (1 ml) and DIPEA (1 ml). The reaction mixture was stirred at room temperature for 18 h. After addition of water, the mixture was extracted four times with ethyl acetate. The combined organic phase was dried over magnesium sulfate, filtered and concentrated under reduced pressure. Purification by chromatography (silica gel, 7% MeOH in dichloromethane) resulted in 0.45 g of the mixture of diastereomers (ratio about 2:1).

D) (2S,4R)-1-[5-Chloro-1-(2,4-dimethoxy-benzenesulfonyl)-3-(2,4-dimethoxy-pyrimidin-5-yl)-2-oxo-2,3-dihydro-1H-indol-3-yl]-4-hydroxy-pyrrolidine-2-carboxylic acid dimethylamide Sodium hydride (12 mg of 60% dispersion in mineral oil, 0.3 mmol) was added to an ice-cold solution of the mixture of diastereomers from step C (139 mg, 0.30 mmol) in DMF (1.5 ml). The reaction mixture was stirred at 0° C. for 0.5 h and then 2,4-dimethoxy-benzenesulfonyl chloride (71 mg, 0.3 mmol) was added. After the reaction mixture had been stirred at room temperature for one hour, water was added, and the mixture was extracted with ethyl acetate. The organic layer was washed with water and saturated brine and dried over magnesium sulfate. Purification by chromatography (silica gel, 5% MeOH in dichloromethane) resulted in 63 mg of the less polar diastereomer (levorotatory isomer) and 25 mg of the more polar diastereomer (dextrorotatory isomer) as colorless waxes.

Example 3

(2S,4R)-1-[5-Chloro-1-(2,4-dimethoxy-benzenesulfonyl)-3-(2,4-dimethoxy-pyrimidin-5-yl)-2-oxo-2,3-dihydro-1H-indol-3-yl]-4-hydroxy-pyrrolidine-2-carboxylic acid dimethylamide, levorotatory diastereomer This diastereomer is the less polar diastereomer from step D.
$^1$H NMR (400 MHz, DMSO-$d_6$) δ 8.80 (1H), 7.97 (1H), 7.75 (1H), 7.45 (1H), 7.20 (1H), 6.75 (2H), 4.95 (1H), 4.55 (1H), 4.30 (1H), 3.90 (6H), 3.75 (3H), 3.37 (3H), 3.05 (1H), 1.75 (1H), 1.65 (1H); MS (API-ES, pos) m/z=662 [M+H]

Example 4

(2S,4R)-1-[5-Chloro-1-(2,4-dimethoxy-benzenesulfonyl)-3-(2,4-dimethoxy-pyrimidin-5-yl)-2-oxo-2,3-dihydro-1H-indol-3-yl]-4-hydroxy-pyrrolidine-2-carboxylic acid dimethylamide, dextrorotatory diastereomer This diastereomer is the more polar diastereomer from step D.

$^1$H NMR (400 MHz, DMSO-$d_6$) δ 8.95 (1H), 7.95 (1H), 7.80 (1H), 7.50 (1H), 6.80 (2H), 6.70 (1H), 4.70 (1H), 4.20 (1H), 3.90 (6H), 3.75 (3H), 3.65 (1H), 3.40 (3H), 3.00 (1H), 2.80 (1H), 2.65 (3H), 2.45 (3H), 1.70 (2H); MS (API-ES, pos) m/z=662 [M+H]

Example 5 and Example 6

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide A) 5-Chloro-3-(2-methoxy-pyridin-3-yl)-3-hydroxy-1,3-dihydroindol-2-one A 1.7 M solution of tert-butyllithium in pentane (28.9 ml, 49.1 mmol) was added to THF (100 ml) at −78° C. 2-Bromomesitylene (3.6 ml, 23.4 mmol) was added dropwise and the mixture stirred at −78° C. for 1 h. 2-Methoxypyridine (1.92 ml, 18 mmol) was added at −78° C. and then the mixture was stirred at 0° C. for 1 h and at ambient temperature for 0.5 h. A suspension of 5-chloroisatin (1.27 g, 9.0 mmol) in THF (50 ml) was added dropwise at −78° C. The reaction mixture was allowed to warm to room temperature and then saturated ammonium chloride solution was added. The mixture was extracted three times with ethyl acetate, and the collected extracts were washed with saturated brine. The organic phase was dried over magnesium sulfate, filtered and concentrated under reduced pressure. Purification by crystallization from dichloromethane yielded 1.1 g of the intermediate.

B) 3,5-Dichloro-3-(2-methoxy-pyridin-3-yl)-1,3-dihydroindol-2-one

Pyridine (0.33 ml) and thionyl chloride (0.30 ml) were added successively to an ice-cold solution of the intermediate from step A (1.1 g, 3.44 mmol) in dichloromethane (10 ml). The reaction mixture was stirred at 0° C. for 1 h and then saturated ammonium chloride solution was added. The organic phase was dried over magnesium sulfate, filtered and concentrated under reduced pressure. The crude intermediate was rapidly employed without further purification in the next step.

C) (2S,4R)-1-[5-Chloro-3-(2-methoxy-pyridin-3-yl)-2-oxo-2,3-dihydro-1H-indol-3-yl]-4-hydroxy-pyrrolidine-2-carboxylic acid dimethylamide (2S,4R)-4-Hydroxy-pyrrolidine-2-carboxylic acid dimethylamide hydrochloride (0.67 g, 3.44 mmol) was added to a solution of the intermediate from step B in a mixture of dichloromethane (10 ml), THF (2 ml) and DIPEA (1.6 ml). The reaction mixture was stirred at room temperature for 18 h. After addition of water, the mixture was extracted four times with ethyl acetate. The combined organic phase was dried over magnesium sulfate, filtered and concentrated under reduced pressure. Purification by chromatography (silica gel, 5% MeOH in dichloromethane) resulted in 0.58 g of the more polar diastereomer, 0.2 g of the less polar diastereomer and 0.4 g of a mixture of diastereomers (ratio about 1:1).

Example 5

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer Sodium hydride (14.4 mg of 60% dispersion in mineral oil, 0.36 mmol) was added to an ice-cold solution of the more polar diastereomer intermediate from step C (150 mg, 0.35 mmol) in DMF (3.2 ml). The reaction mixture was stirred at 0° C. for 1 h and then 2,4-dimethoxy-benzenesulfonyl chloride (86.2 mg, 0.364 mmol) was added. After the reaction mixture had been stirred at room temperature for one hour, water was added, and the mixture was extracted with ethyl acetate. The organic layer was washed with water and brine and dried over magnesium sulfate. Purification by chromatography (silica gel, 5% MeOH in dichloromethane) and trituration with diethyl ether (6 ml) and hexane (6 ml) resulted in 130 mg of the levorotatory diastereomer as a white solid.

$[\alpha]_D^{20°\,C.}$ (c=0.1, CHCl$_3$): −233;
$^1$H NMR (400 MHz, DMSO-d$_6$) δ 8.20 (1H), 8.10 (1H), 8.00 (1H), 7.80 (1H), 7.45 (1H), 7.00 (2H), 6.75 (2H), 4.95 (1H), 4.55 (1H), 4.35 (1H), 3.85 (3H), 3.75 (3H), 3.35 (3H), 3.00 (1H), 2.55 (3H), 2.45 (3H), 1.65 (2H); MS (API-ES, pos) m/z=631 [M+H]

Example 6

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, dextrorotatory diastereomer The diastereomer product was prepared by the method described in the previous paragraph starting from the less polar diastereomer intermediate from step C. Purification by chromatography (silica gel, 5% MeOH in dichloromethane) and trituration with diethyl ether/hexane resulted in the dextrorotatory diastereomer as a white solid.

$[\alpha]_D^{20°\,C.}$ (c=0.1, CHCl$_3$): +142;
$^1$H NMR (400 MHz, DMSO-d$_6$) δ 8.45 (1H), 8.13 (1H), 7.97 (1H), 7.80 (1H), 7.50 (1H), 7.20 (1H), 6.80 (2H), 6.55 (1H), 4.70 (1H), 4.25 (1H), 3.90 (3H), 3.80 (3H), 3.65 (1H), 3.35 (3H), 3.00 (1H), 2.75 (1H), 2.65 (3H), 2.40 (3H), 1.70 (2H); MS (API-ES, pos) m/z=631 [M+H]

The following compounds can be prepared in an analogous fashion to examples 1 to 6 employing the synthetic route that is outlined in synthesis scheme 1:

Example 7

(2S,4R)-1-[5-Chloro-1-(2,4-dimethoxy-benzenesulfonyl)-3-(2-methyl-pyridin-3-yl)-2-oxo-2,3-di hydro-1H-indol-3-yl]-4-hydroxy-pyrrolidine-2-carboxylic acid dimethylamide

Example 8

(2S,4R)-1-[5-Chloro-1-(2,4-dimethoxy-benzenesulfonyl)-3-(2-chloropyridin-3-yl)-2-oxo-2,3-dihydro-1H-indol-3-yl]-4-hydroxy-pyrrolidine-2-carboxylic acid dimethylamide

Example 9

(2S,4R)-1-[5-Chloro-1-(2,4-dimethoxy-benzenesulfonyl)-3-(3-methoxy-pyridin-2-yl)-2-oxo-2,3-dihydro-1H-indol-3-yl]-4-hydroxy-pyrrolidin-2-carboxylic acid dimethylamide, levorotatory diastereomer A) 5-Chloro-3-hydroxy-3-(3-methoxy-pyridin-2-yl)-1,3-dihydro-indol-2-one A 1.7 M solution of tert-butyllithium in pentane (57.8 mL) was added to THF (200 ml) at −78° C. 2-Bromomesitylene (3.6 mL) was added dropwise, keeping the temperature below −60° C., and the mixture stirred at −78° C. for 1 h. 3-Methoxypyridine (3.6 mL) was added dropwise at −78° C. and then the mixture was stirred between −30° C. and −20° C. The reaction mixture was re-cooled to −78° C. and a slurry of 5-chloroisatin (3.26 g) in THF (100 mL) was added portionwise, keeping the temperature below −60° C. The reaction mixture was stirred at −78° C. for 1 h. The cooling bath was removed and the reaction mixture was stirred for 30 min. The reaction mixture was quenched with 10% aqueous ammonium chloride solution and extracted several times with ethyl acetate. The combined organic layers were washed with water, dried over magnesium sulfate and evaporated to low volume. Upon standing, 1.05 g of a cream-colored solid separated which was filtered off, washed with ethyl acetate and dried in vacuo.

The subsequent steps were performed in analogous fashion to Examples 5 and 6.

Example 9

$^1$H NMR (400 MHz, DMSO-d$_6$) δ 8.15 (1H), 7.95 (1H), 7.75 (1H), 7.43 (3H), 6.90 (1H), 6.75 (2H), 5.75 (1H), 4.70 (1H), 4.20 (1H), 3.90 (3H), 3.75 (3H), 3.25 (3H), 3.05 (1H), 2.70 (3H), 2.45 (3H), 1.95 (1H), 1.60 (1H); MS (API-ES, pos) m/z=631 [M+H]

Example 10

(2S,4R)-1-[5-Chloro-1-(2,4-dimethoxy-benzenesulfonyl)-3-(4-methoxy-pyridin-3-yl)-2-oxo-2,3-dihydro-1H-indol-3-yl]-4-hydroxy-pyrrolidine-2-carboxylic acid dimethylamide, levorotatory diastereomer A) 5-Chloro-3-hydroxy-3-(4-methoxy-pyridin-3-yl)-1,3-dihydro-indol-2-one A 1.7 M solution of tert-butyllithium in pentane (43.4 mL) was added to THF (150 ml) at −78° C. 2-Bromomesitylene (5.4 mL) was added dropwise, keeping the temperature below −60° C., and the mixture stirred at −78° C. for 1 h. 4-Methoxypyridine (2.75 mL) was added dropwise at −78° C. and then the mixture was stirred at −30° C. to −20° C. for 3.5 h. The reaction mixture was re-cooled to −78° C. and a slurry of 5-chloroisatin (2.44 g) in THF (120 mL) was added portionwise, keeping the temperature below −65° C. The reaction mixture was stirred at −78° C. for 30 min. The reaction mixture was allowed to warm to −20° C. and then 10% aqueous ammonium chloride solution (75 mL) was added. After stirring for 10 min, the white solid was filtered off, washed with water (excess) and ethyl acetate (20 mL). Yield after drying in vacuo: 1.8 g (42%). MS (API-ES, pos) m/z=383 [M+H]

The subsequent steps were performed in analogous fashion to Examples 5 and 6.

Example 10

$^1$H NMR (400 MHz, DMSO-d$_6$) δ 8.85 (1H), 8.40 (1H), 8.00 (1H), 7.75 (1H), 7.45 (1H), 7.05 (1H), 6.95 (1H), 6.75 (2H), 4.95 (1H), 4.60 (1H), 4.35 (1H), 3.85 (3H), 3.75 (3H), 3.35 (3H), 3.00 (1H), 2.55 (3H), 2.45 (3H), 1.60 (2H); MS (API-ES, pos) m/z=631 [M+H]

Example 11

(2S,4R)-1-[5-Chloro-1-(2,4-dimethoxy-benzenesulfonyl)-3-(4-methyl-pyridin-3-yl)-2-oxo-2,3-di hydro-1H-indol-3-yl]-4-hydroxy-pyrrolidine-2-carboxylic acid dimethylamide

Example 12

(2S,4R)-1-[5-Chloro-1-(2,4-dimethoxy-benzenesulfonyl)-3-pyrazin-2-yl-2-oxo-2,3-dihydro-1H-indol-3-yl]-4-hydroxy-pyrrolidine-2-carboxylic acid dimethylamide

Example 13

(2S,4R)-1-[5-Chloro-1-(2,4-dimethoxy-benzenesulfonyl)-3-(3-methoxy-pyrazin-2-yl)-2-oxo-2,3-dihydro-1H-indol-3-yl]-4-hydroxy-pyrrolidine-2-carboxylic acid dimethylamide, levorotatory diastereomer A) 5-Chloro-3-hydroxy-3-(3-methoxy-pyrazin-2-yl)-1,3-dihydro-indol-2-one n-BuLi (26 mmol, 16.3 mL of a 1.6M solution in hexanes) was added dropwise to a solution of 2,2,6,6-tetramethylpiperidine (26 mmol, 4.4 mL) in THF (150 mL) at 0° C. After stirring for 30 min at 0° C., the solution was cooled to −78° C. and a solution of 2-methoxypyrazine (20 mmol, 1.93 mL) in THF (30 mL) was added dropwise. After stirring at −78° C. for 15 min, a suspension of 5-chloroisatin (10 mmol, 1.82 g) in THF (50 mL) was added. The reaction mixture was stirred at 0° C. for 2 h, then saturated ammonium chloride solution was added. The mixture was extracted three times with ethyl acetate, and the collected extracts were washed with saturated brine. The organic phase was dried over magnesium sulfate, filtered and concentrated under reduced pressure. Purification by crystallization from diethyl ether yielded 1.14 g of the required intermediate.

The subsequent steps were performed in analogous fashion to Examples 5 and 6.

Example 13

$^1$H NMR (500 MHz, DMSO-d$_6$) δ 8.23 (1H), 8.17 (1H), 7.95 (1H), 7.75 (1H), 7.47 (1H), 7.15 (1H), 6.75 (2H), 5.05 (1H), 4.65 (1H), 4.25 (1H), 3.87 (3H), 3.67 (3H), 3.50 (3H), 3.00 (1H), 2.65 (3H), 1.90 (1H), 1.65 (1H); MS (API-ES, pos) m/z=632 [M+H]

Example 14

(2S,4R)-1-[5-Chloro-1-(2,4-dimethoxy-benzenesulfonyl)-3-(3,6-dimethoxy-pyridazin-4-yl)-2-oxo-2,3-dihydro-1H-indol-3-yl]-4-hydroxy-pyrrolidine-2-carboxylic acid dimethylamide

Example 15

(2S,4R)-1-[5-Chloro-1-(2,4-dimethoxy-benzenesulfonyl)-3-(isoquinolin-4-yl)-2-oxo-2,3-dihydro-1H-indol-3-yl]-4-hydroxy-pyrrolidine-2-carboxylic acid dimethylamide

Example 16

(2S,4R)-1-[5-Chloro-1-(2,4-dimethoxy-benzenesulfonyl)-3-(quinolin-3-yl)-2-oxo-2,3-dihydro-1H-indol-3-yl]-4-hydroxy-pyrrolidine-2-carboxylic acid dimethylamide

Example 17

(2S,4R)-1-[5-Chloro-1-(2,4-dimethoxy-benzenesulfonyl)-3-(thiazol-2-yl)-oxo-2,3-dihydro-1H-indol-3-yl]-4-hydroxy-pyrrolidine-2-carboxylic acid dimethylamide

Example 18

(2S,4R)-1-[5-Chloro-1-(2,4-dimethoxy-benzenesulfonyl)-3-(1-methyl-1H-benzimidazol-2-yl)-oxo-2,3-dihydro-1H-indol-3-yl]-4-hydroxy-pyrrolidine-2-carboxylic acid dimethylamide

Example 19

(2S,4R)-1-[5-Chloro-1-(2,4-dimethoxy-benzenesulfonyl)-3-(1-methyl-1H-imidazol-2-yl)-oxo-2,3-dihydro-1H-indol-3-yl]-4-hydroxy-pyrrolidine-2-carboxylic acid dimethylamide

Example 20

(2S,4R)-1-[5-Chloro-1-(2,4-dimethoxy-benzenesulfonyl)-3-(benzoxazol-2-yl)-oxo-2,3-dihydro-1H-indol-3-yl]-4-hydroxy-pyrrolidine-2-carboxylic acid dimethylamide

Example 21

(2S,4R)-1-[5-Chloro-1-(2,4-dimethoxy-benzenesulfonyl)-3-(3-methyl-benzo[b]thiophen-2-yl)-oxo-2,3-dihydro-1H-indol-3-yl]-4-hydroxy-pyrrolidine-2-carboxylic acid dimethylamide

Example 22

(2S,4R)-1-[5-Chloro-1-(2,4-dimethoxy-benzenesulfonyl)-3-(3-methyl-thiophen-2-yl)-oxo-2,3-di hydro-1H-indol-3-yl]-4-hydroxy-pyrrolidine-2-carboxylic acid dimethylamide

Example 23

(2S,4R)-1-[5-Chloro-1-(2,4-dimethoxy-benzenesulfonyl)-3-(benzo[b]thiophen-7-yl)-oxo-2,3-di hydro-1H-indol-3-yl]-4-hydroxy-pyrrolidine-2-carboxylic acid dimethylamide

Example 24

(2S,4R)-1-[5-Chloro-1-(2,4-dimethoxy-benzenesulfonyl)-3-(benzofuran-7-yl)-oxo-2,3-dihydro-1H-indol-3-yl]-4-hydroxy-pyrrolidine-2-carboxylic acid dimethylamide

Example 25

(2S,4R)-1-[5-Chloro-1-(2,4-dimethoxy-benzenesulfonyl)-3-(benzofuran-2-yl)-oxo-2,3-dihydro-1H-indol-3-yl]-4-hydroxy-pyrrolidine-2-carboxylic acid dimethylamide

Example 26

(2S,4R)-1-[5-Chloro-1-(2,4-dimethoxy-benzenesulfonyl)-3-(3-methyl-furan-2-yl)-oxo-2,3-dihydro-1H-indol-3-yl]-4-hydroxy-pyrrolidine-2-carboxylic acid dimethylamide

Example 27

(2S,4R)-1-[5-Chloro-1-(2,4-dimethoxy-benzenesulfonyl)-3-furan-3-yl-oxo-2,3-dihydro-1H-indol-3-yl]-4-hydroxy-pyrrolidine-2-carboxylic acid dimethylamide

Example 28

(2S,4R)-1-[5-Chloro-3-(2-methoxy-phenyl)-2-oxo-1-(quinoline-8-sulfonyl)-2,3-dihydro-1H-indol-3-yl]-4-hydroxy-pyrrolidine-2-carboxylic acid dimethylamide, levorotatory diastereomer

A) 5-Chloro-3-hydroxy-3-(2-methoxy-phenyl)-1,3-dihydroindol-2-one

Magnesium turnings (40 g, 1.65 mol) are introduced into diethyl ether (100 ml) and, while stirring, a solution of 2-bromoanisole (206 ml, 1.65 mol) in diethyl ether (450 ml) is added dropwise. The reaction can be initiated, if necessary, by adding iodine crystals. During the addition, the reaction mixture should boil gently. After the addition, the mixture was stirred at room temperature for 1 hour. A slurry of 5-chloroisatin (75 g, 0.41 mol) in THF (750 ml) was added to the Grignard solution while cooling slightly (temperature 18-24° C.), and the mixture was stirred at room temperature for 30 min. The reaction mixture was stirred into ammonium chloride solution and extracted several times with ethyl acetate. The combined organic phase was washed four times with water, dried over magnesium sulfate and concentrated under reduced pressure. The remaining residue was stirred with 2-propanol. The resulting precipitate was filtered off, washed with 2-propanol and diethyl ether and dried. 106 g of the desired intermediate were obtained.

B) (2S,4R)-1-[5-Chloro-3-(2-methoxy-phenyl)-2-oxo-2,3-dihydro-1H-indol-3-yl]-4-hydroxy-pyrrolidine-2-carboxylic acid dimethylamide Pyridine (56 ml) and thionyl chloride (38 ml) were successively added dropwise to an ice-cold solution of the intermediate from step A (100 g, 0.345 mol) in dichloromethane (1 000 ml). The reaction mixture was stirred at 0° C. for 30 min and then stirred into ice-water. The organic phase was separated, and the aqueous phase was extracted once more with dichloromethane. The combined organic phase was washed several times with water, dried over magnesium sulfate and concentrated under reduced pressure. The residue was stirred with hot toluene. The resulting crystals were filtered off in the cold, washed with toluene and pentane and dried. 79 g of the desired 3-chloro intermediate were obtained.

(2S,4R)-4-Hydroxy-pyrrolidine-2-carboxylic acid dimethylamide hydrochloride (12.6 g, 65 mmol) was added to a solution of the 3-chloro intermediate (20.0 g, 65 mmol) in dichloromethane (400 ml) and DIPEA (28 ml, 162 mmol). The solution was stirred at room temperature overnight. The reaction mixture was diluted with dichloromethane and washed with dilute sodium bicarbonate and several times with water. The organic phase was dried over magnesium sulfate and concentrated under reduced pressure. The residue was recrystallized from acetone. 6.5 g of the less polar (as judged by thin-layer-chromatography on silica gel, 7% MeOH in dichloromethane) diastereomer were obtained. The mother liquor was concentrated under reduced pressure. Purification of the remaining residue by chromatography (silica gel, 7% MeOH in dichloromethane) resulted in 1.0 g of the less polar diastereomer and 17.3 g of the more polar diastereomer.

C) (2S,4R)-1-[5-Chloro-3-(2-methoxy-phenyl)-2-oxo-1-(quinoline-8-sulfonyl)-2,3-dihydro-1H-indol-3-yl]-4-hydroxy-pyrrolidine-2-carboxylic acid dimethylamide, levorotatory diastereomer Potassium tert-butoxide (38 mg, 0.34 mmol) was added to an ice-cold solution of the more polar diastereomer from step B (150 mg, 0.34 mmol) in DMF (3 ml), and the mixture was stirred at 0° C. for 30 min. After addition of 8-quinolinesulfonyl chloride (79 mg, 0.34 mmol), the reaction mixture was left to stir at room temperature for 3 hours. Water was added to the reaction mixture, which was then extracted with ethyl acetate. The organic layer was washed with water and saturated brine and dried over magnesium sulfate. Purification by chromatography (silica gel, 7% MeOH in dichloromethane) resulted in 159 mg of the product.

$[\alpha]_D^{20°\ C.}$ (c=0.20, CHCl$_3$): −148;

$^1$H-NMR (D$_6$-DMSO): δ=1.4-1.6 (5H), 1.7 (2H), 1.9 (2H), 2.15-2.35 (4H), 2.45 (3H), 2.9 (2H), 3.25 (4H), 3.7 (3H), 4.15 (2H), 6.55 (1H), 6.6 (1H), 6.75-6.90 (3H), 7.05-7.2 (2H), 7.40 (1H), 7.65 (1H), 7.9 (1H), 8.0 (1H), 8.15 (1H) and 8.85 (1H) ppm; MS (API-ES, pos) m/z=621 [M+H]

Examples 29 to 61 can be prepared in analogous fashion to Example 28 using Example 28B (more polar diastereomer) as the starting material in the sulfonylation reaction. Heterocyclic sulfonyl chlorides were acquired from commercial suppliers or synthesized according to standard methods, for example according to the following procedure:

5-Methyl-pyridine-2-sulfonyl chloride

Chlorine gas was bubbled through a solution of 2-mercapto-5-methylpyridine (64 mmol, 8.00 g, from Ubichem) in conc. hydrochloric acid (80 mL) at 0° C. After 1 h, the reaction mixture was poured into an ice-water mixture (200 mL). The suspension was extracted several times with dichloromethane and the combined organic layers were washed with sodium bicarbonate solution. After drying over sodium sulfate, the volatiles were evaporated in vacuo to yield 9.80 g (80%) of a colorless oil which solidified in the refrigerator.

5-Trifluoromethyl-pyridine-2-sulfonyl chloride, 5-Bromo-pyridine-2-sulfonyl chloride, 5-Bromo-3-methyl-pyridine-2-sulfonyl chloride, Pyridine-2-sulfonyl chloride, 4-Methyl-pyridine-2-sulfonyl chloride, 6-Methyl-pyridine-2-sulfonyl chloride, 5-Chloro-pyridine-2-sulfonyl chloride were prepared in analogous fashion.

Example 29

(2S,4R)-1-[5-Chloro-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethyl-amide, levorotatory diastereomer $^1$H-NMR (D$_6$-DMSO): δ=1.65 (1H), 2.05 (1H), 2.4-2.6 (6H), 2.8 (1H), 3.0 (3H), 3.1 (1H), 4.3 (1H), 4.45 (1H), 4.95 (1H, OH), 6.8 (1H), 6.9 (1H), 7.0 (1H), 7.25-7.35 (2H), 7.4 (1H), 7.65 (1H) and 8.0-8.2 (3H) ppm; MS (API-ES, pos) m/z=576 [M+H]

Example 30

(2S,4R)-1-[5-Chloro-3-(2-methoxy-phenyl)-2-oxo-1-(thiophene-3-sulfonyl)-2,3-dihydro-1H-indol-3-yl]-4-hydroxy-pyrrolidine-2-carboxylic acid dimethyl-amide trifluoroacetate Example 31

(2S,4R)-1-[5-Chloro-1-(5-chloro-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.12, CHCl$_3$): −131;
$^1$H-NMR (D$_6$-DMSO): δ=1.7 (1H), 2.0 (1H), 2.35-2.55 (6H), 2.65 (1H), 2.95 (1H), 3.2 (3H), 4.25 (1H), 4.45 (1H), 4.7 (broad, 1H, OH), 6.8 (1H), 6.9 (1H), 7.0 (1H), 7.25 (1H), 7.30 (1H), 7.35 (1H), 7.60 (1H), 7.90 (1H) and 8.05 (1H) ppm.

Example 32

(2S,4R)-1-[1-(3-Bromo-5-chloro-thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.17, CHCl$_3$): −142;
$^1$H-NMR (CDCl$_3$) δ=1.75 (1H), 1.9 (1H), 2.3 (1H), 2.4 (3H), 2.75 (3H), 3.3 (1H), 3.6 (3H), 4.65 (1H), 4.8 (1H), 6.8 (1H), 7.0 (2H), 7.1 (1H), 7.3 (1H), 7.8 (1H) and 7.9 (1H) ppm.

Example 33

(2S,4R)-1-[1-(4-Bromo-5-chloro-thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide trifluoroacetate Example 34

(2S,4R)-1-[5-Chloro-1-(5-methyl-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide Example 35

(2S,4R)-1-[5-Chloro-1-(4,5-dichloro-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide trifluorocetate Example 36

(2S,4R)-1-[5-Chloro-1-(3-methylbenzo[b]thiophene-2-sulfonyl)-3-(2-methoxyphenyl)-2-oxo-2,3-dihydro-1H-indol-3-yl]-4-hydroxy-pyrrolidine-2-carboxylic acid dimethylamide Example 37

(2S,4R)-1-[1-(Benzo[b]thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.18, CHCl$_3$): −146;
$^1$H-NMR (D$_6$-DMSO): δ=1.65 (1H), 2.0 (1H), 2.3-2.5 (7H), 2.75 (1H), 2.85 (3H), 4.3 (1H), 4.45 (1H), 4.9 (1H, OH), 6.8 (1H), 6.95 (1H), 7.0 (1H), 7.25 (1H), 7.45 (1H), 7.55 (1H), 7.6 (1H), 7.7 (1H), 8.05 (1H), 8.1 (1H), 8.15 (1H), and 8.55 (1H) ppm.

Example 38

(2S,4R)-1-[5-Chloro-1-(5-chloro-3-methyl-benzo[b]thiophene-2-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.19, CHCl$_3$): −104;
$^1$H-NMR (CDCl$_3$): δ=1.7 (2H), 2.4 (3H), 2.5-2.8 (4H), 2.9 (3H), 3.3-3.5 (4H), 4.55 (1H), 4.7 (1H), 6.7 (1H), 7.0 (1H), 7.1 (1H), 7.25 (1H), 7.45 (1H), 7.75 (1H) and 7.7-7.9 (3H) ppm.

Example 39

(2S,4R)-1-[5-Chloro-3-(2-methoxy-phenyl)-1-(1-methyl-1H-imidazole-4-sulfonyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.20, CHCl$_3$): −152;
$^1$H-NMR (D$_6$-DMSO): δ=1.7 (2H), 2.3-2.5 (8H), 3.1 (3H), 3.75 (3H), 4.35 (1H), 4.55 (1H), 4.9 (1H, OH), 6.85 (1H), 6.9 (1H), 7.0 (1H), 7.3 (1H), 7.4 (1H), 7.75 (1H), 7.85 (1H) and 8.25 (1H) ppm.

Example 40

(2S,4R)-1-[5-Chloro-1-(1,2-dimethyl-1H-imidazole-4-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.20, CHCl$_3$): −161

Example 41

(2S,4R)-1-[5-Chloro-1-(5-chloro-1,3-dimethyl-1H-pyrazole-4-sulfonyl)-3-(2-methoxy-phenyl)-2-oxo-2,3-dihydro-1H-indol-3-yl]-4-hydroxy-pyrrolidine-2-carboxylic acid dimethylamide trifluoroacetate

Example 42

(2S,4R)-1-[5-Chloro-3-(2-methoxy-phenyl)-2-oxo-1-(1,3,5-trimethyl-1H-pyrazole-4-sulfonyl)-2,3-dihydro-1H-indol-3-yl]-4-hydroxy-pyrrolidine-2-carboxylic acid dimethylamide trifluoroacetate

Example 43

(2S,4R)-1-[5-Chloro-3-(2-methoxy-phenyl)-1-(5-methyl-1-phenyl-1H-pyrazole-4-sulfonyl)-2-oxo-2,3-dihydro-1H-indol-3-yl]-4-hydroxy-pyrrolidine-2-carboxylic acid dimethylamide trifluoroacetate

Example 44

(2S,4R)-1-[5-Chloro-1-(3,5-dimethyl-isoxazole-4-sulfonyl)-3-(2-methoxy-phenyl)-2-oxo-2,3-dihydro-1H-indol-3-yl]-4-hydroxy-pyrrolidine-2-carboxylic acid dimethylamide trifluoroacetate

Example 45

(2S,4R)-1-[5-Chloro-1-(2,4-dimethyl-thiazole-5-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.21, CHCl$_3$): −152;
$^1$H-NMR (CDCl$_3$) δ=1.75 (1H), 1.9 (1H), 2.4 (3H), 2.6-2.9 (10H), 3.3 (1H), 3.5 (3H), 4.6 (1H), 4.75 (1H), 6.75 (1H), 6.95 (1H), 7.1 (1H), 7.2 (2H), 7.8 (1H) and 7.9 (1H) ppm; MS (API-ES, pos) m/z=605 [M+H]

Example 46

(2S,4R)-1-[5-Chloro-1-(6-chloro-imidazo[2,1-b]thiazole-5-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $[\alpha]_D^{20°\ C.}$ (c=0.22, CHCl$_3$): −127;
MS (API-ES, pos) m/z=650 [M+H]

Example 47

(2S,4R)-1-[5-Chloro-3-(2-methoxy-phenyl)-2-oxo-1-(pyridine-2-sulfonyl)-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.80 (1H), 8.35 (1H), 8.25 (1H), 8.00 (1H), 7.80 (2H), 7.45 (1H), 7.30 (1H), 7.00 (1H), 6.95 (1H), 6.85 (1H), 4.95 (1H), 4.50 (1H), 4.30 (1H), 3.10 (3H), 2.45 (4H), 1.65 (1H); MS (API-ES, pos) m/z=571 [M+H]

Example 48

(2S,4R)-1-[1-(5-Bromo-pyridine-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.95 (1H), 8.50 (1H), 8.30 (1H), 8.00 (1H), 7.77 (1H), 7.40 (1H), 7.30 (1H), 7.03 (1H), 6.97 (1H), 6.90 (1H), 4.90 (1H), 4.45 (1H), 4.30 (1H), 3.27, 2.40 (4H), 1.60 (1H); MS (API-ES, pos) m/z=649 [M+H]

Example 49

(2S,4R)-1-[5-Chloro-1-(5-trifluoro-methyl-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide

Example 50

(2S,4R)-1-[5-Chloro-1-(5-methoxy-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide

Example 51

(2S,4R)-1-[5-Chloro-3-(2-methoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.63 (1H), 8.25 (1H), 8.00 (2H), 7.80 (1H), 7.40 (1H), 7.25 (1H), 7.00 (1H), 7.95 (1H), 6.85 (1H), 4.90 (1H), 4.50 (1H), 4.30 (1H), 3.15, 2.45 (7H), 1.65 (1H); MS (API-ES, pos) m/z=585 [M+H]

Example 52

(2S,4R)-1-[5-Chloro-1-(5-chloro-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.85 (1H), 8.35 (2H), 8.00 (1H), 7.75 (1H), 7.40 (1H), 7.30 (1H), 7.00 (2H), 6.40 (1H), 4.90 (1H), 4.40 (1H), 4.30 (1H), 3.30, 2.40, 1.60 (1H); MS (API-ES, pos) m/z=605 [M+H]

Example 53

(2S,4R)-1-[1-(5-Bromo-3-methyl-pyridine-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.75 (1H), 8.40 (1H), 8.00 (1H), 7.70 (1H), 7.40 (1H), 7.30 (1H), 7.00 (2H), 6.93 (1H), 5.00 (1H), 4.50 (1H), 4.35 (1H), 3.45 (3H), 2.80 (3H), 2.35, 1.65 (1H); MS (API-ES, pos) m/z=663 [M+H]

Example 54

(2S,4R)-1-[5-Chloro-1-(3,5-dimethyl-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.43 (1H), 7.95 (1H), 7.85 (1H), 7.75 (1H), 7.40 (1H), 7.30 (1H), 7.00 (2H), 6.90 (1H), 4.95 (1H), 4.55 (1H), 4.40 (1H), 3.40 (3H), 2.75 (3H), 2.35, 1.63 (1H); MS (API-ES, pos) m/z=599 [M+H]

Example 55

(2S,4R)-1-[5-Chloro-3-(2-methoxy-phenyl)-2-oxo-1-(pyridine-3-sulfonyl)-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 9.33 (1H), 8.90 (1H), 8.60 (1H), 8.10 (1H), 7.75 (2H), 7.40 (1H), 7.30 (1H), 7.05 (1H), 7.00 (1H), 6.85 (1H), 4.95 (1H), 4.45 (1H), 4.20 (1H), 3.20 (3H), 3.15 (1H), 2.70 (1H), 2.30 (3H), 2.00 (1H), 1.60 (1H); MS (API-ES, pos) m/z=571 [M+H]

Example 56

(2S,4R)-1-[5-Chloro-3-(2-methoxy-phenyl)-1-(6-morpholin-4-yl-pyridine-3-sulfonyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.75 (1H), 8.12 (1H), 8.00 (1H), 7.70 (1H), 7.37 (1H), 7.30 (1H), 7.00 (2H), 6.93 (1H), 6.87 (1H), 4.90 (1H), 4.47 (1H), 4.25 (1H), 3.65 (8H), 3.20 (3H), 2.30-2.45 (5H), 2.00 (1H), 1.65 (1H); MS (API-ES, pos) m/z=656 [M+H]

Example 57

(2S,4R)-1-[5-Chloro-3-(2-methoxy-phenyl)-2-oxo-1-(6-phenoxy-pyridine-3-sulfonyl)-2,3-dihydro-1H-indol-3-yl]-4-hydroxy-pyrrolidine-2-carboxylic acid dimethylamide trifluoroacetate

Example 58

(2S,4R)-1-[5-Chloro-1-(6-methoxypyridine-3-sulfonyl)-3-(2-methoxyphenyl)-2-oxo-2,3-dihydro-1H-indol-3-yl]-4-hydroxy-pyrrolidine-2-carboxylic acid dimethylamide

Example 59

(2S,4R)-1-[5-Chloro-1-(5-bromo-6-chloropyridine-3-sulfonyl)-3-(2-methoxy-phenyl)-2-oxo-2,3-dihydro-1H-indol-3-yl]-4-hydroxy-pyrrolidine-2-carboxylic acid dimethylamide

Example 60

(2S,4R)-1-[5-Chloro-3-(2-methoxy-phenyl)-1-(4-methyl-3,4-dihydro-2H-benzo[1,4]oxazine-7-sulfonyl)-2-oxo-2,3-dihydro-1H-indol-3-yl]-4-hydroxy-pyrrolidine-2-carboxylic acid dimethylamide trifluoroacetate

Example 61

(2S,4R)-1-[5-Chloro-3-(2-methoxy-phenyl)-2-oxo-1-(1,2,3,4-tetrahydro-isoquinoline-7-sulfonyl)-2,3-dihydro-1H-indol-3-yl]-4-hydroxy-pyrrolidine-2-carboxylic acid dimethylamide, levorotatory diastereomer (−)-(2S,4R)-1-{5-Chloro-3-(2-methoxy-phenyl)-2-oxo-1-[2-(2,2,2-trifluoro-acetyl)-1,2,3,4-tetrahydro-isoquinoline-7-sulfonyl]-2,3-dihydro-1H-indol-3-yl}-4-hydroxy-pyrrolidine-2-carboxylic acid dimethylamide (obtained from Example 28B (more polar diastereomer) and commercially available 2-(2,2,2-Trifluoro-acetyl)-1,2,3,4-tetrahydro-isoquinoline-7-sulfonyl chloride) (1.39 mmol, 1.00 g) was deprotected using $K_2CO_3$ (1 eq.) at RT for 6 h in a 9:1 MeOH:$H_2O$ mixture (22 mL). The solution was evaporated in vacuo. The residue was dissolved in a 1:1 $CH_2Cl_2$:$H_2O$ mixture and the phases were separated. The organic phase was dried over magnesium sulfate and evaporated in vacuo to afford 850 mg of the required product.

$^1$H-NMR (400 MHz, DMSO-$d_6$) δ 9.06 (2H, s br.), 8.22-7.91 (3H, m), 7.72 (1H, d), 7.56 (1H, d), 7.38 (1H, d), 7.27 (1H, t), 7.02 (1H, t), 6.96 (1H, s), 6.83 (1H, d), 3.40 (2H, s br.), 3.08 (2H, t), 3.02 (2H, s br.), 2.05 (1H, m br.), 1.72-1.57 (1H, m); MS (API-ES, pos) m/z=625 [M+H]

Example 62

5-Chloro-1-(2,4-dimethox-benzenesulfonyl)-3-hydroxy-3-(3-methyl-thiophen-2-yl)-1,3-dihydro-indol-2-one A) 5-Chloro-3-hydroxy-3-(3-methyl-thiophen-2-yl)-1,3-dihydro-indol-2-one Magnesium turnings (6.8 g, 0.27 mmol) are introduced into diethyl ether (30 ml), and, while stirring, a solution of 2-bromo-3-methyl-thiophene (50 g, 0.282 mol) in diethyl ether (100 ml) is added dropwise. The reaction can be initiated if necessary by adding iodine crystals. During the addition, the reaction mixture should boil gently. After the addition, the mixture was stirred at room temperature for 1 hour. A suspension of 5-chloroisatin (19 g, 0.105 mol) in THF (200 ml) was added to the Grignard solution while cooling slightly (temperature 18-24° C.) and the mixture was stirred at room temperature for 30 min. The reaction mixture was stirred into ammonium chloride solution and extracted several times with ethyl acetate. The combined organic phases were washed with saturated brine, dried over magnesium sulfate and concentrated under reduced pressure. The residue was stirred with diethyl ether. The resulting precipitate was filtered off, washed with diethyl ether and dried. 26 g of the desired intermediate were obtained.

B) 5-Chloro-1-(2,4-dimethoxy-benzenesulfonyl)-3-hydroxy-3-(3-methyl-thiophen-2-yl)-1,3-dihydro-indol-2-one Potassium tert-butoxide (1.21 g, 10.8 mmol) was added to an ice-cold solution of the intermediate from step A (3.00 g, 10.8 mmol) in DMF (30 ml), and the mixture was stirred at 0° C. for 30 min. After addition of 2,4-dimethoxy-benzenesulfonyl chloride (2.5 g, 10.8 mmol), the reaction mixture was left to stir at 0° C. for 1 hour. Further addition of 0.2 equivalent each of potassium tert-butoxide and sulfonyl chloride led to no further advance in the reaction according to thin-layer chromatography. The reaction mixture was stirred into dilute potassium carbonate solution, and the resulting precipitate was filtered off. The precipitate was taken up in ethyl acetate, and the extract was washed with saturated brine and dried over magnesium sulfate. Purification by chromatography (silica gel, gradient 30% to 50% ethyl acetate in heptane) and recrystallization from diethyl ether resulted in 0.96 g of the desired product.

$^1$H-NMR (D$_6$-DMSO) δ=1.55 (3H), 3.6 (3H), 3.85 (3H), 6.7 (1H), 6.75 (2H), 7.2 (1H), 7.35 (1H), 7.55 (1H), 7.6 (1H), 7.8 (1H) and 7.9 (1H) ppm.

Example 63

(4-Chloro-phenyl)-carbamic acid 5-chloro-1-(2,4-dimethoxy-benzenesulfonyl)-3-(3-methyl-thiophen-2-yl)-2-oxo-2,3-dihydro-1H-indol-3-yl ester 4-Chlorophenyl isocyanate (32 mg, 0.208 mmol) and DMAP (5 mg) were successively added to a solution of example 62 (100 mg, 0.21 mmol) in toluene (20 ml) and stirred at 90° C. for 30 min. The solvent was removed under reduced pressure, and the residue was taken up in ethyl acetate. The organic phase was washed with dilute citric acid solution and saturated sodium chloride solution, dried over magnesium sulfate and concentrated under reduced pressure. Recrystallization from methanol resulted in 80 mg of the desired product.

$^1$H-NMR (D$_6$-DMSO) δ=1.95 (3H), 3.85 (3H), 3.9 (3H), 6.6 (1H), 6.7 (1H), 6.75 (1H), 7.05 (1H), 7.7 (1H), 7.4-7.5 (2H), 7.6-7.75 (5H) and 9.25 (1H) ppm.

Example 64

5-Chloro-3-hydroxy-3-(2-methoxy-phenyl)-1-(quinoline-8-sulfonyl)-1,3-dihydro-indol-2-one Potassium tert-butoxide (0.81 g, 7.25 mmol) was added to an ice-cold solution of Example 28A (2.00 g, 6.90 mmol) in DMF (24 ml), and the mixture was stirred at 0° C. for 60 min. After addition of 8-quinoline-sulfonyl chloride (1.65 g, 7.25 mmol), the reaction mixture was left to stir at 0° C. for 2 hours and then at room temperature overnight. The reaction mixture was stirred into dilute potassium carbonate solution, and the resulting precipitate was filtered off, washed with water and dried. Purification by chromatography (silica gel, 10% MeOH in dichloromethane) resulted in 1.8 g of the product.

$^1$H-NMR (D$_6$-DMSO) δ=2.75 (3H), 6.75 (1H), 6.8 (1H), 7.05 (1H), 7.1 (1H), 7.3 (1H), 7.55 (1H), 7.7 (1H), 7.75 (1H), 7.9 (1H), 8.2 (1H), 8.45 (1H), 8.6 (1H), 8.65 (1H) and 8.85 (1H) ppm.

Example 65

Piperidine-1-carboxylic acid 5-chloro-3-(2-methoxy-phenyl)-2-oxo-1-(quinoline-8-sulfonyl)-2,3-dihydro-1H-indol-3-yl ester A) Carbonic acid 5-chloro-3-(2-methoxy-phenyl)-2-oxo-1-(quinoline-8-sulfonyl)-2,3-dihydro-1H-indol-3-yl ester phenyl ester Phenyl chloroformate (0.35 ml, 2.79 mmol) was added dropwise to a solution of example 64 (300 mg, 0.624 mmol) in pyridine (6 ml) while cooling slightly. The reaction mixture was stirred at room temperature overnight. After addition of ice-water, the mixture was extracted with ethyl acetate, and the organic phase was washed several times with dilute citric acid solution and water. The organic phase was dried over magnesium sulfate and concentrated under reduced pressure. The residue was triturated with diethyl ether, and the resulting precipitate was filtered off, washed with diethyl ether and dried. 310 mg of the desired intermediate were obtained.

B) Piperidine-1-carboxylic acid 5-chloro-3-(2-methoxy-phenyl)-2-oxo-1-(quinoline-8-sulfonyl)-2,3-dihydro-1H-indol-3-yl ester Piperidine (0.132 ml, 1.33 mmol) was added to a solution of the intermediate from step A (200 mg, 0.33 mmol) in THF (10 ml), and the reaction solution was stirred overnight. 2 M sodium hydroxide solution was added to the reaction mixture, which was then extracted with dichloromethane. The organic phase was washed three times with water and concentrated under reduced pressure. Recrystallization from dichloromethane/diethyl ether resulted in 112 mg of the desired product.

$^1$H-NMR (D$_6$-DMSO) δ=1.2 (2H), 2.85 (2H), 3.3 (3H), 3.5 (2H), 6.9 (1H), 7.05 (1H), 7.1 (1H), 7.35 (1H), 7.5 (1H), 7.6-7.7 (2H), 7.8 (1H), 8.1 (1H), 8.4 (1H), 8.55 (1H), 8.6 (1H) and 8.8 (1H) ppm.

Examples 66 to 76 can be prepared in analogous fashion to Example 65

Example 66

4-Pyridin-4-yl-piperazine-1-carboxylic acid 5-chloro-3-(2-methoxy-phenyl)-2-oxo-1-(quinoline-8-sulfonyl)-2,3-dihydro-1H-indol-3-yl ester

Example 67

3,4,5,6-Tetrahydro-2H-[4,4']bipyridinyl-1-carboxylic acid 5-chloro-3-(2-methoxy-phenyl)-2-oxo-1-(quinoline-8-sulfonyl)-2,3-dihydro-1H-indol-3-yl ester

Example 68

4-Pyridin-2-yl-piperazine-1-carboxylic acid 5-chloro-1-(2,4-dimethoxy-benzenesulfonyl)-3-(2,4-dimethoxy-pyrimidin-5-yl)-2-oxo-2,3-dihydro-1H-indol-3-yl ester

Example 69

4-Pyridin-2-yl-piperazine-1-carboxylic acid 5-chloro-1-(2,4-dimethoxy-benzenesulfonyl)-3-(2-methoxy-pyridin-3-yl)-2-oxo-2,3-dihydro-1H-indol-3-yl ester

Example 70

4-Pyridin-2-yl-piperazine-1-carboxylic acid 5-chloro-3-(2,4-dimethoxy-pyrimidin-5-yl)-2-oxo-1-(quinoline-8-sulfonyl)-2,3-dihydro-1H-indol-3-yl ester

Example 71

4-Pyridin-4-yl-piperazine-1-carboxylic acid 5-chloro-3-(2,4-dimethoxy-pyrimidin-5-yl)-2-oxo-1-(quinoline-8-sulfonyl)-2,3-dihydro-1H-indol-3-yl ester

Example 72

4-Pyridin-2-yl-piperazine-1-carboxylic acid 5-chloro-3-(2-methoxy-pyridin-3-yl)-2-oxo-1-(quinoline-8-sulfonyl)-2,3-dihydro-1H-indol-3-yl ester

Example 73

4-Pyridin-4-yl-piperazine-1-carboxylic acid 5-chloro-3-(2-methoxy-pyridin-3-yl)-2-oxo-1-(quinoline-8-sulfonyl)-2,3-dihydro-1H-indol-3-yl ester

Example 74

3,4,5,6-Tetrahydro-2H-[4,4']bipyridinyl-1-carboxylic acid 5-chloro-3-(2-methoxy-pyridin-3-yl)-2-oxo-1-(quinoline-8-sulfonyl)-2,3-dihydro-1H-indol-3-yl ester

Example 75

4-(1-Methyl-piperidin-4-yl)-piperazine-1-carboxylic acid 5-chloro-3-(2-methoxy-phenyl)-2-oxo-1-(quinoline-8-sulfonyl)-2,3-dihydro-1H-indol-3-yl ester bismethanesulfonate $^1$H-NMR (D$_6$-DMSO): δ=1.35 (2H), 1.65 (2H), 1.8 (2H), 2.05-2.2 (4H), 2.25 (2H), 2.45 (2H), 2.75 (2H), 2.85 (2H), 3.3 (3H), 3.45 (1H), 3.55 (1H), 6.90 (1H), 7.05 (1H), 7.15 (1H), 7.35 (1H), 7.5 (1H), 7.6-7.7 (2H), 7.8 (1H), 8.10 (1H), 8.4 (1H), 8.55 (1H), 8.65 (1H), 8.8 (1H) and 10.9 (broad) ppm.

Example 76

4-(1-Methyl-piperidin-4-yl)-piperazine-1-carboxylic acid 1-benzenesulfonyl-5-chloro-3-(2-methoxy-pyridin-3-yl)-2-oxo-2,3-dihydro-1H-indol-3-yl ester $^1$H NMR (400 MHz, DMSO-d$_6$) δ 8.20 (2H), 8.10 (2H), 7.80 (2H), 7.70 (2H), 7.50 (1H), 7.30 (1H), 7.20 (1H), 3.60 (2H), 3.10 (2H), 2.75 (2H), 2.35 (2H), 2.15 (4H), 1.85 (2H), 1.70 (2H), 1.40 (4H); MS (API-ES, pos) m/z=640 [M+H]

Examples 77 to 82 bearing an amide moiety in the 3-position of the oxindole core were prepared employing synthetic methods that are outlined in synthetic scheme 3:

Example 77

N-[5-Chloro-3-(2-methoxy-phenyl)-2-oxo-1-(quinoline-8-sulfonyl)-2,3-dihydro-1H-indol-3-yl]-acetamide $^1$H-NMR (D$_6$-DMSO): δ=1.8 (3H), 3.55 (3H), 6.75 (1H), 7.0 (1H), 7.05 (1H), 7.2-7.35 (1H), 7.65 (1H), 7.85 (1H), 7.95 (1H), 8.4 (1H), 8.55 (1H), 8.65 (1H), 8.75 (1H) and 8.95 (1H) ppm.

Example 78

3,4,5,6-Tetrahydro-2H-[1,4']bipyridinyl-4-carboxylic acid [5-chloro-3-(2-methoxy-phenyl)-2-oxo-1-(quinoline-8-sulfonyl)-2,3-dihydro-1H-indol-3-yl]-amide

Example 79

3,4,5,6-Tetrahydro-2H-[1,4']bipyridinyl-4-carboxylic acid [5-chloro-3-(2-methoxy-pyridin-3-yl)-2-oxo-1-(quinoline-8-sulfonyl)-2,3-dihydro-1H-indol-3-yl]-amide

Example 80

(E)-N-[5-Chloro-3-(2-methoxy-phenyl)-2-oxo-1-(quinoline-8-sulfonyl)-2,3-dihydro-1H-indol-3-yl]-3-pyridin-4-yl-acrylamide $^1$H-NMR (D$_6$-DMSO): δ=3.85 (3H), 6.45 (1H), 6.65 (1H), 6.85 (1H), 6.9 (1H), 7.15 (1H), 7.3 (3H), 7.35 (2H), 7.4-7.6 (2H), 7.75 (1H), 8.1-8.3 (4H), 8.6 (1H) and 8.75-8.85 (2H) ppm.

Example 81

(E)-N-[3-(2-Methoxy-phenyl)-2-oxo-1-(thiophene-2-sulfonyl)-2,3-dihydro-1H-indol-3-yl]-3-pyridin-4-yl-acrylamide

Example 82

3,4,5,6-Tetrahydro-2H-[1,4']bipyridinyl-4-carboxylic acid [5-chloro-1-(2,4-dimethoxy-benzenesulfonyl)-3-(2-methoxy-pyridin-3-yl)-2-oxo-2,3-dihydro-1H-indol-3-yl]-amide $^1$H NMR (400 MHz, DMSO-d$_6$) δ 9.05 (1H), 8.20 (1H), 8.15 (2H), 7.90 (1H), 7.70 (1H), 7.50 (1H), 7.40 (1H), 7.35

(1H), 7.00 (1H), 6.80 (2H), 6.65 (2H), 3.80 (8H), 3.50 (3H), 2.90 (2H), 1.75 (1H), 1.60 (1H), 1.35 (2H); MS (API-ES, pos) m/z=678 [M+H]

The procedure for the synthesis of Example 83 is representative for the synthesis of examples that bear a urea moiety in the 3-position of the oxindole.

Example 83

4-(1-Methyl-piperidin-4-yl)-piperazine-1-carboxylic acid [3-(2-ethoxy-phenyl)-5-methoxy-2-oxo-1-(quinoline-8-sulfonyl)-2,3-dihydro-1H-indol-3-yl]-amide A) 3-(2-Ethoxy-phenyl)-3-hydroxy-5-methoxy-1,3-dihydro-indol-2-one 40 g (1.65 mol) of magnesium chips and 5% of the total amount of the 2-bromo-1-ethoxy benzene were added to 100 ml diethyl ether and after adding a few crystals iodine the mixture was carefully heated to initiate the reaction. To the refluxing mixture the remaining amount of 203 ml (1.65 mol) 2-bromo-1-ethoxy benzene, dissolved in 450 ml diethyl ether, was added slowly to maintain the reaction. Then 75 g (0.41 mol) of 5-methoxyisatine, suspended in 750 ml THF, were added to the cooled reaction mixture. After stirring the reaction mixture for 30 minutes at ambient temperature, the mixture was poured into an ice/aqueous NH$_4$Cl mixture. The aqueous phase was extracted with ethyl acetate several times and the combined organic phase was washed with H$_2$O, dried over magnesium sulfate and the solvent was removed in vacuo.

B) 3-Chloro-3-(2-ethoxy-phenyl)-5-methoxy-1,3-dihydro-indol-2-one 5 g (16.7 mmol) of the intermediate from step A and 2.6 g (33.4 mmol) pyridine were dissolved in 50 mL CH$_2$Cl$_2$ and at 0° C. 3 g (25.1 mmol) SOCl$_2$ were added slowly. Then the reaction mixture was stirred for 30 min. at 0° C. The reaction mixture was poured into an ice/water mixture and the organic phase was separated, washed with H$_2$O, dried over magnesium sulfate and finally the solvent was removed in vacuo. The resulting residue was suspended in ether. The solid residue was separated and dried to give 3.2 g of the intermediate, which was used without further purification.

C) 3-Amino-3-(2-ethoxy-phenyl)-5-methoxy-1,3-dihydro-indol-2-one 3.2 g (10 mmol) of the intermediate from step B were suspended in 40 ml CH$_2$Cl$_2$. 50 ml of a 2M solution of NH$_3$ in ethanol were added and the reaction mixture was stirred for 16 h at ambient temperature. The mixture was poured into an ice/water mixture and the precipitate was separated. The precipitate was redissolved in ethyl acetate. This organic phase was washed with 2M aqueous HCl. The aqueous phase was made alkaline (pH=8-9) and then extracted with ethyl acetate. The organic phase was dried over magnesium sulfate and the solvent was removed in vacuo to yield 1.7 g of the intermediate.

D) [3-(2-Ethoxy-phenyl)-5-methoxy-2-oxo-2,3-dihydro-1H-indol-3-yl]-carbamic acid phenyl ester 1.8 g (6 mmol) of the intermediate from step C were dissolved in 20 ml pyridine. At 0° C. 0.99 g (6.3 mmol) phenyl chloroformate were added and afterwards the reaction mixture was stirred for 1 h at 0° C. This mixture was poured into an ice/water mixture. The pH of the aqueous phase was adjusted to 5 and the resulting mixture was extracted with ethyl acetate. The organic phase was separated, dried over magnesium sulfate and the solvent was removed in vacuo. The resulting solid (2 g) was used in the next step without further purification.

E) 4-(1-Methyl-piperidin-4-yl)-piperazine-1-carboxylic acid [3-(2-ethoxy-phenyl)-5-methoxy-2-oxo-2,3-dihydro-1H-indol-3-yl]-amide 1.9 g (4.5 mmol) of the intermediate from step D and 1.75 g (9.5 mmol) 1-(1-methylpiperidine-4-yl)-piperazine were dissolved in 30 ml dry THF and refluxed for 90 minutes. The volatiles were removed in vacuo. The resulting residue was dissolved in ethyl acetate, washed with H$_2$O and dried over magnesium sulfate and the solvent was removed in vacuo. The residue was treated with H$_2$O and the resulting precipitate was separated to yield 1.5 g of the intermediate.

F) 4-(1-Methyl-piperidin-4-yl)-piperazine-1-carboxylic acid [3-(2-ethoxy-phenyl)-5-methoxy-2-oxo-1-(quinoline-8-sulfonyl)-2,3-dihydro-1H-indol-3-yl]-amide 200 mg (0.39 mmol) of the intermediate from step E were dissolved in 30 ml THF. At 0° C. 19 mg (0.43 mmol) NaH (55%) were added. After stirring the reaction mixture for 20 min, 99 mg (0.43 mmol) 1-quinoline-8-sulfonylchloride were added. The reaction mixture was stirred for 1 h. The solvent was removed in vacuo. The residue was recrystallized from CH$_3$OH/H$_2$O to obtain 180 mg of Example 83.

$^1$H-NMR (CDCl$_3$): δ=1.4-1.6 (5H), 1.7 (2H), 1.9 (2H), 2.15-2.35 (4H), 2.45 (3H), 2.9 (2H), 3.25 (4H), 3.7 (3H), 4.15 (2H), 6.55 (1H), 6.6 (1H), 6.75-6.90 (3H), 7.05-7.2 (2H), 7.40 (1H), 7.65 (1H), 7.9 (1H), 8.0 (1H), 8.15 (1H) and 8.85 (1H) ppm.

The following examples bearing a carbamate or urea moiety in the 3-position of the oxindole core can be synthesized in analogous fashion to Example 65 or Example 83, respectively.

Example 100

4-Methyl-piperazine-1-carboxylic acid 5-chloro-3-(2-methoxy-phenyl)-2-oxo-1-(quinoline-8-sulfonyl)-2,3-dihydro-1H-indol-3-yl ester $^1$H-NMR (D$_6$-DMSO): δ=2.0-2.2 (5H), 2.75 (2H), 2.9 (2H), 3.3 (3H), 3.45 (1H), 3.65 (1H), 6.90 (1H), 7.05 (1H), 7.15 (1H), 7.35 (1H), 7.5 (1H), 7.6-7.75 (2H), 7.8 (1H), 8.1 (1H), 8.4 (1H), 8.55 (1H), 8.65 (1H) and 8.8 (1H) ppm.

Example 101

Dimethyl-carbamic acid 5-chloro-3-(2-methoxy-phenyl)-2-oxo-1-(quinoline-8-sulfonyl)-2,3-dihydro-1H-indol-3-yl ester $^1$H-NMR (D$_6$-DMSO): δ=2.45 (3H), 2.95 (3H), 3.3 (3H), 6.90 (1H), 7.05 (1H), 7.15 (1H), 7.35 (1H), 7.5 (1H), 7.65 (1H), 7.75 (1H), 7.8 (1H), 8.1 (1H), 8.4 (1H), 8.55 (1H), 8.65 (1H) and 8.8 (1H) ppm.

Example 102

[1,4']Bipiperidinyl-1-carboxylic acid 5-chloro-3-(2-methoxy-phenyl)-2-oxo-1-(quinoline-8-sulfonyl)-2,3-dihydro-1H-indol-3-yl ester hydrochloride ¹H-NMR (D₆-DMSO): δ=1.2-1.4 (4H), 1.6-1.85 (6H), 1.95 (1H), 2.1 (1H), 2.6 (1H), 2.8-3.0 (3H), 3.25 (3H), 3.3 (1H), 3.4 (1H), 4.2 (1H), 6.90 (1H), 7.05 (1H), 7.15 (1H), 7.35 (1H), 7.5 (1H), 7.6-7.75 (2H), 7.8 (1H), 8.15 (1H), 8.4 (1H), 8.55 (2H), 8.6 (1H), 8.8 (1H) and 9.9 (broad) ppm.

Example 103

4-(4-Methyl-piperazin-1-yl)-piperidine-1-carboxylic acid 1-benzenesulfonyl-5-chloro-3-(2-methoxy-pyridin-3-yl)-2-oxo-2,3-dihydro-1H-indol-3-yl ester ¹H NMR (400 MHz, DMSO-d₆) δ 8.20 (2H), 8.10 (2H), 7.80 (2H), 7.70 (2H), 7.50 (1H), 7.27 (1H), 7.20 (1H), 4.20 (1H), 3.55 (1H), 3.05 (1H), 2.65 (1H), 2.40 (8H), 2.15 (3H), 1.80 (1H), 1.65 (1H), 1.40 (1H), 1.10 (1H); MS (API-ES, pos) m/z=640 [M+H]

Example 104

4-(1-Methyl-piperidin-4-yl)-piperazine-1-carboxylic acid 5-chloro-1-(2,4-dimethoxy-benzenesulfonyl)-2-oxo-3-pyridin-2-yl-2,3-dihydro-1H-indol-3-yl ester trishydrochloride ¹H-NMR (D₆-DMSO): δ=2.1 (2H), 2.3 (2H), 2.7 (3H), 2.8-3.9 (18H), 4.4 (1H), 6.7 (2H), 7.35 (2H), 7.5 (1H), 7.7-8.0 (4H), 8.3 (1H), and 11.5 (broad, N⁺H) and 11.8 (broad, N⁺H) ppm.

Example 105

4-(1-Methyl-piperidin-4-yl)-piperazine-1-carboxylic acid 5-chloro-1-(2,4-dimethoxy-benzenesulfonyl)-3-(2-methoxy-pyridin-3-yl)-2-oxo-2,3-dihydro-1H-indol-3-yl ester ¹H NMR (400 MHz, DMSO-d₆) δ 8.20 (1H), 8.15 (1H), 7.90 (1H), 7.80 (1H), 7.50 (1H), 7.25 (1H), 7.15 (1H), 6.70 (2H), 3.85 (3H), 3.60 (7H), 3.50 (1H), 3.10 (2H), 2.80 (2H), 2.30 (2H), 2.15 (4H), 1.80 (2H), 1.65 (2H), 1.35 (4H); MS (API-ES, pos) m/z=700 [M+H]

Example 106

4-(1-Methyl-piperidin-4-yl)-piperazine-1-carboxylic acid 1-(2,4-dimethoxy-benzenesulfonyl)-3-(2-methoxy-pyridin-3-yl)-2-oxo-2,3-dihydro-1H-indol-3-yl ester ¹H NMR (400 MHz, DMSO-d₆) δ 8.20 (1H), 8.10 (1H), 7.90 (1H), 7.75 (1H), 7.40 (1H), 7.15 (1H), 7.10 (2H), 6.70 (2H), 3.85 (3H), 3.40-3.70 (8H), 3.10 (2H), 2.80 (2H), 2.40 (3H), 2.10 (3H), 1.80 (2H), 1.65 (2H), 1.35 (4H); MS (API-ES, pos) m/z=666 [M+H]

Example 107

4-(4-Methyl-piperazin-1-yl)-piperidine-1-carboxylic acid 1-(2,4-dimethoxy-benzenesulfonyl)-3-(2-methoxy-pyridin-3-yl)-5-methyl-2-oxo-2,3-dihydro-1H-indol-3-yl ester ¹H-NMR (400 MHz, CDCl₃) δ 8.20-8.06 (2H, m), 7.92 (1H, d), 7.82 (1H, d), 7.13 (1H, d), 6.94 (1H, t), 6.76 (1H, s), 6.54 (1H, d), 6.43 (1H, s), 4.21 (1H, d), 3.85 (6H, d), 3.77 (1H, m), 3.63 (3H, s), 2.92 (1H, t), 2.71-2.18 (16H, incl. 2.29 (3H, s), 2.24 (3H, s), 1.64 (4H, s br.); MS (API-ES, pos) m/z=680 [M+H]

Example 108

4-(1-Methyl-piperidin-4-yl)-piperazine-1-carboxylic acid 5-cyano-1-(2,4-dimethoxy-benzenesulfonyl)-3-(2-methoxy-pyridin-3-yl)-2-oxo-2,3-dihydro-1H-indol-3-yl ester ¹H NMR (400 MHz, DMSO-d₆) δ 8.20 (2H), 7.90 (3H), 7.75 (1H), 7.17 (1H), 6.70 (2H), 3.85 (3H), 3.60 (4H), 3.55 (3H), 3.50 (1H), 3.10 (2H), 2.75 (2H), 2.30 (2H), 2.15 (4H), 1.80 (2H), 1.65 (2H), 1.20-1.50 (4H); MS (API-ES, pos) m/z=691 [M+H]

Example 109

4-(1-Methyl-piperidin-4-yl)-piperazine-1-carboxylic acid 1-(2,4-dimethoxy-benzenesulfonyl)-3-(2-methoxy-pyridin-3-yl)-5-methyl-2-oxo-2,3-di hydro-1H-indol-3-yl ester ¹H-NMR (400 MHz, CDCl₃) δ 8.10 (2H, m), 7.92 (1H, d), 7.79 (1H, d), 7.14 (1H, d), 6.94 (1H, m), 6.76 (1H, s), 6.54 (1H, d), 6.41 (1H, s), 3.84 (6H, d), 3.63 (3H, s), 3.58 (2H, s br.), 3.17 (2H, s br.), 2.92 (2H, d), 2.53 (2H, s br.), 2.40 (2H, s br.), 2.26 (3H, s), 2.24 (3H, s), 1.94 (2H, t), 1.85-1.47 (8H, m); MS (API-ES, pos) m/z=680 [M+H]

Example 110

4-(1-Methyl-piperidin-4-yl)-piperazine-1-carboxylic acid 1-(2,4-dimethoxy-benzenesulfonyl)-5-methoxy-3-(2-methyl-pyridin-3-yl)-2-oxo-2,3-dihydro-1H-indol-3-yl ester trishydrochloride ¹H-NMR (D₆-DMSO): δ=2.1 (2H), 2.3 (2H), 2.7 (6H), 3.0 (2H), 3.15 (1H), 3.3-4.0 (18H), 4.3 (1H), 6.6 (1H), 6.7 (1H), 6.9 (1H), 7.15 (1H), 7.3 (1H), 7.4 (1H), 7.7 (1H), 7.8 (1H), 8.6 (1H), 10.6 (broad, N⁺H) and 11.6 (broad, N⁺H) ppm.

Example 111

4-(1-Methyl-piperidin-4-yl)-piperazine-1-carboxylic acid 5-chloro-1-(2-fluoro-benzenesulfonyl)-3-(2-methoxy-pyridin-3-yl)-2-oxo-2,3-dihydro-1H-indol-3-yl ester diacetate MS (ESI, pos) m/z=658 [M+H]

Example 112

4-(1-Methyl-piperidin-4-yl)-piperazine-1-carboxylic acid 5-chloro-1-(4-fluoro-benzenesulfonyl)-3-(2-methoxy-pyridin-3-yl)-2-oxo-2,3-dihydro-1H-indol-3-yl ester diacetate MS (ESI, pos) m/z=658 [M+H]

Example 113

4-(1-Methyl-piperidin-4-yl)-piperazine-1-carboxylic acid 5-chloro-1-(4-cyano-benzenesulfonyl)-3-(2-methoxy-pyridin-3-yl)-2-oxo-2,3-dihydro-1H-indol-3-yl ester diacetate MS (ESI, pos) m/z=665 [M+H]

Example 114

4-(1-Methyl-piperidin-4-yl)-piperazine-1-carboxylic acid 5-chloro-1-(3-methoxy-benzenesulfonyl)-3-(2-methoxy-pyridin-3-yl)-2-oxo-2,3-dihydro-1H-indol-3-yl ester diacetate MS (ESI, pos) m/z=670 [M+H]

Example 115

4-(1-Methyl-piperidin-4-yl)-piperazine-1-carboxylic acid 5-chloro-1-(4-methoxy-benzenesulfonyl)-3-(2-methoxy-pyridin-3-yl)-2-oxo-2,3-dihydro-1H-indol-3-yl ester diacetate MS (ESI, pos) m/z=670 [M+H]

Example 116

4-(1-Methyl-piperidin-4-yl)-piperazine-1-carboxylic acid 5-chloro-1-(2-chloro-benzenesulfonyl)-3-(2-methoxy-pyridin-3-yl)-2-oxo-2,3-dihydro-1H-indol-3-yl ester diacetate MS (ESI, pos) m/z=674 [M+H]

Example 117

4-(1-Methyl-piperidin-4-yl)-piperazine-1-carboxylic acid 5-chloro-1-(3-chloro-benzenesulfonyl)-3-(2-methoxy-pyridin-3-yl)-2-oxo-2,3-dihydro-1H-indol-3-yl ester diacetate MS (ESI, pos) m/z=674 [M+H]

Example 118

4-(1-Methyl-piperidin-4-yl)-piperazine-1-carboxylic acid 5-chloro-1-(4-chloro-benzenesulfonyl)-3-(2-methoxy-pyridin-3-yl)-2-oxo-2,3-dihydro-1H-indol-3-yl ester diacetate MS (ESI, pos) m/z=674 [M+H]

Example 119

4-(1-Methyl-piperidin-4-yl)-piperazine-1-carboxylic acid 5-chloro-1-(2,4-difluoro-benzenesulfonyl)-3-(2-methoxy-pyridin-3-yl)-2-oxo-2,3-dihydro-1H-indol-3-yl ester diacetate MS (ESI, pos) m/z=677 [M+H]

Example 120

4-(1-Methyl-piperidin-4-yl)-piperazine-1-carboxylic acid 5-chloro-1-(4-isopropyl-benzenesulfonyl)-3-(2-methoxy-pyridin-3-yl)-2-oxo-2,3-dihydro-1H-indol-3-yl ester diacetate MS (ESI, pos) m/z=682 [M+H]

Example 121

4-(1-Methyl-piperidin-4-yl)-piperazine-1-carboxylic acid 5-chloro-1-(3,4-dimethoxy-benzenesulfonyl)-3-(2-methoxy-pyridin-3-yl)-2-oxo-2,3-dihydro-1H-indol-3-yl ester diacetate MS (ESI, pos) m/z=700 [M+H]

Example 122

4-(1-Methyl-piperidin-4-yl)-piperazine-1-carboxylic acid 5-chloro-3-(2-methoxy-pyridin-3-yl)-2-oxo-1-(4-trifluoromethyl-benzenesulfonyl)-2,3-dihydro-1H-indol-3-yl ester diacetate MS (ESI, pos) m/z=708 [M+H]

Example 123

4-(1-Methyl-piperidin-4-yl)-piperazine-1-carboxylic acid 5-chloro-3-(2-methoxy-pyridin-3-yl)-2-oxo-1-(4-trifluoromethoxy-benzenesulfonyl)-2,3-dihydro-1H-indol-3-yl ester diacetate MS (ESI, pos) m/z=724 [M+H]

Example 124

Dimethyl-carbamic acid 3-benzofuran-7-yl-5-chloro-1-(2,4-dimethoxy-benzenesulfonyl)-2-oxo-2,3-dihydro-1H-indol-3-yl ester

Example 125

4-(1-Methyl-piperidin-4-yl)-piperazine-1-carboxylic acid [3-(2-ethoxy-phenyl)-5-methoxy-1-(3-methoxy-thiophene-2-sulfonyl)-2-oxo-2,3-dihydro-1H-indol-3-yl]-amide $^1$H-NMR (CDCl$_3$): δ=1.3 (3H), 1.6-1.8 (2H), 1.8-2.0 (4H), 2.2-2.6 (8 h), 3.1 (2H), 3.2-3.4 (4H), 3.75 (6H), 4.2 (2H), 6.7-7.0 (7H), 7.2 (1H), 7.5 (1H), and 7.8 (1H) ppm.

Example 126

4-(1-Methyl-piperidin-4-yl)-piperazine-1-carboxylic acid 5-methoxy-3-(2-methoxy-phenyl)-2-oxo-1-(thiophene-2-sulfonyl)-2,3-dihydro-1H-indol-3-yl ester dihydrochloride $^1$H-NMR (D$_6$-DMSO): δ=2.1 (2H), 2.3 (2H), 2.7 (3H), 2.8-3.8 (18H), 4.3 (1H), 6.7 (1H), 6.95 (2H), 7.05 (1H), 7.25 (1H), 7.35 (1H), 7.65 (1H), 7.95 (1H), 8.15 (1H), 10.8 (broad, N$^+$H) and 11.8 (broad, N$^+$H) ppm.

Example 127

4-(1-Methyl-piperidin-4-yl)-piperazine-1-carboxylic acid 3-(2-methoxy-phenyl)-5-methyl-2-oxo-1-(pyridine-2-sulfonyl)-2,3-dihydro-1H-indol-3-yl ester dihydrochloride $^1$H-NMR (D$_6$-DMSO): δ=2.0 (2H), 2.15 (3H), 2.3 (2H), 2.7 (3H), 2.9-3.8 (15H), 4.3 (1H), 6.85 (1H), 6.90 (1H), 7.1 (1H), 7.2 (1H), 7.35 (1H), 7.7 (1H), 7.8 (2H), 8.2 (2H), 10.6 (broad, N$^+$H), and 11.7 (broad, N$^+$H) ppm.

Example 128

4-(4-Methyl-piperazin-1-yl)-piperidine-1-carboxylic acid 3-(2-methoxy-phenyl)-5-methyl-2-oxo-1-(pyridine-2-sulfonyl)-2,3-dihydro-1H-indol-3-yl ester dihydrochloride $^1$H-NMR (D$_6$-DMSO): δ=1.4 (1H), 1.6 (1H), 2.0 (1H), 2.2 (3H), 2.65 (2H), 2.8 (3H), 3.0 (2H), 3.2-3.8 (12H), 4.3 (1H), 6.85 (1H), 6.9 (1H), 7.1 (1H), 7.15 (1H), 7.35 (1H), 7.7 (1H), 7.75 (1H), 8.2 (2H), and 8.8 (1H) ppm.

Example 129

4-(1-Methyl-piperidin-4-yl)-piperazine-1-carboxylic acid 3-(2-methoxy-phenyl)-5-methyl-2-oxo-1-(thiophene-2-sulfonyl)-2,3-dihydro-1H-indol-3-yl ester dihydrochloride $^1$H-NMR (D$_6$-DMSO): δ=2.1 (2H), 2.2 (3H), 2.3 (2H), 2.7 (3H), 2.9-3.8 (15H), 4.3 (1H), 6.9 (2H), 7.1 (1H), 7.2 (1H), 7.25 (1H), 7.35 (1H), 7.6 (1H), 7.8 (1H), 7.95 (1H), 8.1 (1H), 10.6 (broad, N$^+$H) and 11.8 (broad, N$^+$H) ppm.

Example 130

4-(4-Methyl-piperazin-1-yl)-piperidine-1-carboxylic acid 3-(2-methoxy-phenyl)-5-methyl-2-oxo-1-(thiophene-2-sulfonyl)-2,3-dihydro-1H-indol-3-yl ester dihydrochloride $^1$H-NMR (D$_6$-DMSO): δ=1.4 (1H), 1.65 (1H), 2.0 (1H), 2.2 (3H), 2.7 (2H), 2.8 (3H), 3.0 (2H), 3.2-3.8 (12H), 4.35 (1H), 6.85 (2H), 6.0 (1H), 7.1 (1H), 7.15 (1H), 7.25 (1H), 7.35 (1H), 7.6 (1H), 7.8 (1H), 8.0 (1H) and 8.1 (1H) ppm.

Example 131

4-(1-Methyl-piperidin-4-yl)-piperazine-1-carboxylic acid 5-methyl-2-oxo-1-(thiophene-2-sulfonyl)-3-o-tolyl-2,3-dihydro-1H-indol-3-yl ester dihydrochloride $^1$H-NMR (D$_6$-DMSO): δ=2.0 (2H), 2.2-2.4 (8H), 2.7 (3H), 2.9-3.8 (12H), 4.3 (1H), 6.8 (1H), 7.1-7.2 (2H), 7.2-7.4 (4H), 7.7 (1H), 7.85 (1H), 8.1 (1H), 10.6 (broad, N$^+$H) and 11.8 (broad, N$^+$H) ppm.

Example 132

4-(4-Methyl-piperazin-1-yl)-piperidine-1-carboxylic acid 5-methyl-2-oxo-1-(thiophene-2-sulfonyl)-3-o-tolyl-2,3-dihydro-1H-indol-3-yl ester dihydrochloride $^1$H-NMR (D$_6$-DMSO): δ=1.5 (1H), 2.1 (1H), 2.25-2.4 (6H), 2.7 (2H), 2.8 (3H), 3.0 (2H), 3.2-3.9 (10H), 4.25 (1H), 6.75 (1H), 7.0-7.2 (2H), 7.2-7.4 (4H), 7.7 (1H), 7.8 (1H) and 8.1 (1H) ppm.

Example 133

4-(1-Methyl-piperidin-4-yl)-piperazine-1-carboxylic acid [3-(2-methoxy-phenyl)-5-methyl-2-oxo-1-(thiophene-2-sulfonyl)-2,3-dihydro-1H-indol-3-yl]-amide dihydrochloride $^1$H-NMR (D$_6$-DMSO): δ=2.1 (2H), 2.2 (3H), 2.3 (3H), 2.7 (3H), 2.8-3.7 (14H), 3.9 (1H), 4.1 (1H), 6.9-7.1 (4H), 7.25 (1H), 7.3 (1H), 7.5 (1H), 7.85 (1H), 7.9 (1H), 8.1 (1H), 10.6 (broad, N$^+$H) and 11.4 (broad, N$^+$H) ppm.

Example 134

4-(1-Methyl-piperidin-4-yl)-piperazine-1-carboxylic acid 5-cyano-2-oxo-1-(pyridine-2-sulfonyl)-3-o-tolyl-2,3-dihydro-1H-indol-3-yl ester dihydrochloride $^1$H-NMR (D$_6$-DMSO): δ=1.9-2.1 (2H), 2.25 (2H), 2.4 (3H), 2.7 (3H), 2.8-3.8 (14H), 6.7 (1H), 7.15 (1H), 7.2-7.35 (2H), 7.75 (1H), 7.9 (1H), 8.05 (2H), 8.15 (2H), 8.6 (1H), 10.3 (broad, N$^+$H) and 11.3 (broad, N$^+$H) ppm.

Example 135

4-(1-Methyl-piperidin-4-yl)-piperazine-1-carboxylic acid 5-cyano-2-oxo-1-(thiophene-2-sulfonyl)-3-o-tolyl-2,3-dihydro-1H-indol-3-yl ester dihydrochloride $^1$H-NMR (D$_6$-DMSO): δ=2.1 (2H), 2.3 (2H), 2.4 (3H), 2.7 (3H), 2.8-3.2 (6H), 3.25-3.8 (7H), 4.1-4.4 (1H), 6.75 (1H), 7.15 (1H), 7.2-7.4 (3H), 7.9 (1H), 8.0 (2H), 8.05 (1H), 8.2 (1H), 10.8 (broad, N$^+$H) and 11.9 (broad, N$^+$H) ppm.

Example 136

4-(1-Methyl-piperidin-4-yl)-piperazine-1-carboxylic acid 5-fluoro-3-(2-methoxy-phenyl)-2-oxo-1-(thiophene-2-sulfonyl)-2,3-dihydro-1H-indol-3-yl ester $^1$H NMR (400 MHz, DMSO-d$_6$) δ 8.15 (1H), 8.00 (1H), 7.80 (1H), 7.75 (1H), 7.40 (1H), 7.25 (2H), 7.15 (1H), 7.05

(1H), 6.95 (1H), 3.60 (2H), 3.10 (2H), 2.80 (2H), 2.45 (2H), 2.35 (2H), 2.15 (4H), 1.90 (2H), 1.70 (2H), 1.40 (2H); MS (API-ES, pos) m/z=629 [M+H]

Example 137

4-(1-Methyl-piperidin-4-yl)-piperazine-1-carboxylic acid 5-methoxy-1-(1-methyl-1H-imidazole-4-sulfonyl)-2-oxo-3-o-tolyl-2,3-dihydro-1H-indol-3-yl ester dihydrochloride $^1$H-NMR (D$_6$-DMSO): δ=2.1 (2H), 2.25-2.4 (5H), 2.7 (3H), 2.9-3.1 (4H), 3.2 (1H), 3.3-4.0 (13H), 4.3 (1H), 6.7 (1H), 6.8 (1H), 7.1 (2H), 7.2-7.3 (2H), 7.7 (2H), 8.1 (1H), 10.6 (broad, N$^+$H) and 11.6 (broad, N$^+$H) ppm.

Example 138

4-(1-Methyl-piperidin-4-yl)-piperazine-1-carboxylic acid 5-methoxy-3-(2-methoxy-phenyl)-2-oxo-1-(pyridine-2-sulfonyl)-2,3-dihydro-1H-indol-3-yl ester dihydrochloride $^1$H-NMR (D$_2$O): δ=1.95 (2H), 2.4 (2H), 2.85 (3H), 3.1 (2H), 3.2-3.8 (16H), 4.0 (1H), 6.7 (1H), 6.9 (1H), 7.0 (1H), 7.1 (1H), 7.4 (1H), 7.7-7.9 (3H), 8.2 (1H), 8.3 (1H), and 8.7 (1H) ppm.

Example 139

4-(1-Methyl-piperidin-4-yl)-piperazine-1-carboxylic acid 3-(2-ethoxy-phenyl)-5-methoxy-2-oxo-1-(thiophene-2-sulfonyl)-2,3-dihydro-1H-indol-3-yl ester $^1$H-NMR (CDCl$_3$): δ=1.25 (3H), 1.55 (2H), 1.7 (2H), 1.9 (2H), 2.2-2.35 (4H), 2.4 (2H), 2.4-2.6 (2H), 2.9 (2H), 3.05 (2H), 3.6 (2H), 3.7 (3H), 3.75 (1H), 3.95 (1H), 6.55 (1H), 6.75 (1H), 6.8 (1H), 7.0 (1H), 7.05 (1H), 7.25 (1H), 7.6 (1H), 7.7 (1H), 7.8 (1H) and 7.9 (1H) ppm.

Example 140

4-(1-Methyl-piperidin-4-yl)-piperazine-1-carboxylic acid 3-(2-ethoxy-phenyl)-5-methoxy-2-oxo-1-(pyridine-2-sulfonyl)-2,3-dihydro-1H-indol-3-yl ester

Example 141

4-(1-Methyl-piperidin-4-yl)-piperazine-1-carboxylic acid 3-(2-ethoxy-phenyl)-5-methoxy-1-(1-methyl-1H-imidazole-4-sulfonyl)-2-oxo-2,3-dihydro-1H-indol-3-yl ester $^1$H-NMR (CDCl$_3$): δ=1.2 (3H), 1.4-1.7 (4H), 1.75 (2H), 1.9 (2H), 2.2-2.5 (7H), 2.6 (2H), 2.9 (2H), 3.1 (1H), 3.25 (1H), 3.6 (2H), 3.7 (3H), 3.75 (1H), 4.0 (1H), 6.5 (1H), 6.75 (1H), 6.8 (1H), 7.0 (1H), 7.25 (1H), 7.45 (1H), 7.7 (1H), 7.8 (1H) and 7.9 (1H) ppm.

Example 142

4-(1-Methyl-piperidin-4-yl)-piperazine-1-carboxylic acid 5-chloro-3-(2-ethoxy-phenyl)-2-oxo-1-(thiophene-2-sulfonyl)-2,3-dihydro-1H-indol-3-yl ester $^1$H-NMR (CDCl$_3$): δ=1.25 (3H), 1.45-1.6 (2H), 1.75 (2H), 1.9 (2H), 2.2-2.3 (4H), 2.4 (2H), 2.4-2.65 (2H), 2.9 (2H), 2.95-3.15 (2H), 3.6 (2H), 3.8 (1H), 4.0 (1H), 6.8 (1H), 6.95 (1H), 7.0 (1H), 7.1 (1H), 7.25-7.35 (2H), 7.65 (1H), 7.7 (1H), 7.85 (1H) and 7.9 (1H) ppm.

Example 143

4-(1-Methyl-piperidin-4-yl)-piperazine-1-carboxylic acid 5-chloro-3-(2-ethoxy-phenyl)-1-(3-methoxy-thiophene-2-sulfonyl)-2-oxo-2,3-dihydro-1H-indol-3-yl ester $^1$H-NMR (CDCl$_3$): δ=1.25 (3H), 1.55 (2H), 1.75 (2H), 1.9 (2H), 2.2-2.3 (4H), 2.3-2.7 (4H), 2.9 (2H), 3.1 (2H), 3.6 (2H), 3.75 (3H), 3.8 (1H), 4.0 (1H), 6.75 (2H), 6.95 (1H), 7.0 (1H), 7.3 (2H), 7.5 (1H), 7.7 (1H) and 7.9 (1H) ppm.

Example 144

4-(1-Methyl-piperidin-4-yl)-piperazine-1-carboxylic acid 5-chloro-3-(2-ethoxy-phenyl)-2-oxo-1-(pyridine-2-sulfonyl)-2,3-dihydro-1H-indol-3-yl ester $^1$H-NMR (CDCl$_3$): δ=1.25 (3H), 1.5-1.65 (2H), 1.7 (2H), 1.9 (2H), 2.2-2.35 (6H), 2.4-2.7 (2H), 2.9 (3H), 3.0 (1H), 3.45-3.6 (2H), 3.8 (1H), 4.0 (1H), 6.75 (2H), 6.9 (1H), 7.0 (1H), 7.2-7.4 (3H), 7.5 (1H), 7.65 (1H), 7.9 (1H), 8.05 (1H), 8.25 (1H) and 8.7 (1H) ppm.

Example 145

4-(1-Methyl-piperidin-4-yl)-piperazine-1-carboxylic acid 5-chloro-3-(2-ethoxy-phenyl)-1-(5-methyl-pyridine-2-sulfonyl)-2-oxo-2,3-dihydro-1H-indol-3-yl ester $^1$H-NMR (CDCl$_3$): δ=1.3 (3H), 1.5-1.65 (2H), 1.7 (2H), 1.9 (2H), 2.2-2.4 (9H), 2.4-2.6 (2H), 2.8-3.0 (3H), 3.05 (1H), 3.6 (2H), 3.8 (1H), 4.0 (1H), 6.75 (1H), 6.9 (1H), 7.0 (1H), 7.2-7.4 (2H), 7.65 (2H), 7.65 (1H), 8.0 (1H), 8.15 (1H) and 8.5 (1H) ppm.

Example 146

4-(1-Methyl-piperidin-4-yl)-piperazine-1-carboxylic acid [3-(2-ethoxy-phenyl)-5-methoxy-2-oxo-1-(thiophene-2-sulfonyl)-2,3-dihydro-1H-indol-3-yl]-amide $^1$H-NMR (CDCl$_3$): δ=1.4-1.6 (5H), 1.75 (2H), 1.9 (2H), 2.15-2.35 (4H), 2.4-2.5 (4H), 2.9 (2H), 3.1-3.4 (4H), 3.7 (3H), 4.1-4.3 (2H), 6.75-6.95 (6H), 7.05 (1H), 7.25 (1H), 7.6 (1H), 7.75 (1H) and 7.9 (1H) ppm.

Example 147

4-(1-Methyl-piperidin-4-yl)-piperazine-1-carboxylic acid [5-chloro-3-(2-ethoxy-phenyl)-2-oxo-1-(thiophene-2-sulfonyl)-2,3-dihydro-1H-indol-3-yl]-amide $^1$H-NMR (CDCl$_3$): δ=1.4-1.65 (5H), 1.75 (2H), 1.9 (2H), 2.2-2.35 (4H), 2.8-3.1 (4H), 2.9 (2H), 3.15-3.3 (4H), 4.1-4.3

(2H), 6.6 (1H), 6.8-7.0 (2H), 7.0 (1H), 7.1 (1H), 7.2-7.35 (3H), 7.6 (1H), 7.8 (1H) and 7.95 (1H) ppm.

Example 148

4-(1-Methyl-piperidin-4-yl)-piperazine-1-carboxylic acid [5-chloro-3-(2-ethoxy-phenyl)-2-oxo-1-(pyridine-2-sulfonyl)-2,3-dihydro-1H-indol-3-yl]-amide dihydrochloride $^1$H-NMR (D$_6$-DMSO): δ=1.2 (3H), 1.9-2.1 (2H), 2.3 (2H), 2.7 (3H), 2.75-3.6 (13H), 3.8-4.0 (2H), 6.95 (2H), 7.2 (1H), 7.25-7.4 (2H), 7.5 (1H), 7.75 (2H), 7.9 (1H), 8.15 (2H), 8.8 (1H), 10.4 (broad, N$^+$H) and 11.1 (broad, N$^+$H) ppm.

Example 149

4-(1-Methyl-piperidin-4-yl)-piperazine-1-carboxylic acid [5-chloro-3-(2-ethoxy-phenyl)-2-oxo-1-(thiophene-3-sulfonyl)-2,3-dihydro-1H-indol-3-yl]-amide $^1$H-NMR (CDCl$_3$): δ=1.4-1.65 (5H), 1.75 (2H), 1.95 (2H), 2.2-2.35 (4H), 2.4-2.55 (4H), 2.9 (2H), 3.15-3.3 (4H), 4.1-4.3 (2H), 6.7 (1H), 6.8-6.95 (2H), 7.0 (1H), 7.2-7.35 (4H), 7.55 (1H), 7.75 (1H) and 8.35 (1H) ppm.

Example 150

4-(1-Methyl-piperidin-4-yl)-piperazine-1-carboxylic acid [5-chloro-3-(2-ethoxy-phenyl)-1-(5-methylpyridine-2-sulfonyl)-2-oxo-2,3-dihydro-1H-indol-3-yl]-amide $^1$H-NMR (CDCl$_3$): δ=1.4-1.8 (7H), 1.9 (2H), 2.2-2.35 (4H), 2.4-2.55 (7H), 2.9 (2H), 3.15-3.35 (4H), 4.1-4.3 (2H), 6.8 (1H), 6.85-6.95 (2H), 7.0 (1H), 7.2-7.35 (3H), 7.65 (1H), 7.9 (1H), 8.15 (1H) and 8.50 (1H) ppm.

Example 151

4-(1-Methyl-piperidin-4-yl)-piperazine-1-carboxylic acid 3-(2-ethoxy-phenyl)-5-fluoro-2-oxo-1-(thiophene-2-sulfonyl)-2,3-dihydro-1H-indol-3-yl ester $^1$H-NMR (CDCl$_3$): δ=1.25 (3H), 1.6 (2H), 1.75 (2H), 2.0 (2H), 2.3 (4H), 2.35 (2H), 2.5 (1H), 2.6 (1H), 2.95 (2H), 3.0-3.15 (2H), 3.55 (2H), 3.75 (1H), 4.0 (1H), 6.7 (1H), 6.75 (1H), 6.95-7.15 (2H), 7.2-7.4 (2H), 7.6 (1H), 7.7 (1H), 7.85 (1H) and 7.9 (1H) ppm.

Example 152

4-(1-Methyl-piperidin-4-yl)-piperazine-1-carboxylic acid 3-(2-ethoxy-phenyl)-5-fluoro-1-(5-methyl-pyridine-2-sulfonyl)-2-oxo-2,3-dihydro-1H-indol-3-yl ester $^1$H-NMR (CDCl$_3$): δ=1.25 (3H), 1.6-1.9 (6H), 2.05 (2H), 2.3-2.6 (9H), 2.9-3.2 (4H), 3.55 (2H), 3.8 (1H), 4.05 (1H), 6.65 (1H), 6.75 (1H), 6.95-7.1 (2H), 7.25 (1H), 7.65 (1H), 8.0 (1H), 8.15 (1H) and 8.50 (1H) ppm.

Example 153

(2-Diethylamino-ethyl)-methyl-carbamic acid 5-chloro-3-(2-methoxy-phenyl)-2-oxo-1-(quinoline-8-sulfonyl)-2,3-dihydro-1H-indol-3-yl ester $^1$H-NMR (CDCl$_3$): δ=0.85 (3H), 1.0 (3H), 2.1 (1H), 2.3 (2H), 2.5-2.7 (3H), 2.75 (1H), 2.45 and 3.0 (3H), 3.35 (1H), 3.65 and 3.7 (3H), 6.80 (1H), 6.95 (1H), 7.0 (1H), 7.3 (2H), 7.4 (1H), 7.6-7.8 (2H), 8.05 (1H), 8.15 (2H) and 8.75-8.9 (2H) ppm.

Example 154

4-(1-Methyl-piperidin-4-yl)-piperazine-1-carboxylic acid 3-(2-ethoxy-phenyl)-5-methoxy-2-oxo-1-(quinoline-8-sulfonyl)-2,3-dihydro-1H-indol-3-yl ester $^1$H-NMR (CDCl$_3$): δ=1.25 (3H), 1.40-1.8 (6H), 1.90 (2H), 2.10-2.40 (4H), 2.45 (2H), 2.80 (2H), 2.9 (2H), 3.5 (2H), 3.70 (3H), 3.8 (1H), 4.1 (1H), 6.55 (1H), 6.80 (1H), 6.85-7.0 (2H), 7.25 (1H), 7.40 (1H), 7.60 (2H), 8.00 (1H), 8.05-8.2 (2H) and 8.75-8.9 (2H) ppm.

Example 155

4-(1-Methyl-piperidin-4-yl)piperazine-1-carboxylic acid 5-chloro-3-(2-ethoxy-phenyl)-2-oxo-1-(quinoline-8-sulfonyl)-2,3-dihydro-1H-indol-3-yl ester $^1$H-NMR (CDCl$_3$): δ=1.25 (3H), 1.40-1.8 (6H), 1.90 (2H), 2.10-2.40 (4H), 2.45 (2H), 2.70 (2H), 2.9 (2H), 3.5 (2H), 3.8 (1H), 4.05 (1H), 6.80 (1H), 6.85-7.0 (2H), 7.25 (1H), 7.3-7.5 (2H), 7.5-7.7 (2H), 8.05 (1H), 8.15 (1H), 8.25 (1H) and 8.75 (2H) ppm.

Example 156

4-(1-Methyl-piperidin-4-yl)piperazine-1-carboxylic acid [5-chloro-3-(2-ethoxy-phenyl)-2-oxo-1-(quinoline-8-sulfonyl)-2,3-dihydro-1H-indol-3-yl]-amide $^1$H-NMR (CDCl$_3$): δ=1.5 (3H), 1.6 (2H), 1.75 (2H), 1.95 (2H), 2.2-2.35 (4H), 2.45 (4H), 2.9 (2H), 3.2 (4H), 4.2 (2H), 6.55 (1H), 6.6 (1H), 6.90 (2H), 7.15 (1H), 7.30 (2H), 7.45 (1H), 7.65 (1H), 8.05 (2H), 8.20 (1H), 8.75 (1H) and 8.80 (1H) ppm.

Example 157

4-(1-Methyl-piperidin-4-yl)piperazine-1-carboxylic acid 3-(2-ethoxy-phenyl)-5-fluoro-2-oxo-1-(quinoline-8-sulfonyl)-2,3-dihydro-1H-indol-3-yl ester $^1$H-NMR (CDCl$_3$): δ=1.25 (3H), 1.4-1.9 (6H), 2.0-2.6 (8H), 2.7 (2H), 3.05 (2H), 3.50 (2H), 3.8 (1H), 4.05 (1H), 6.65 (1H), 6.75 (1H), 6.95 (1H), 7.1 (1H), 7.30 (1H), 7.40 (1H), 7.60 (1H), 7.65 (1H), 8.05 (1H), 8.15 (1H), 8.25 (1H) and 8.75 (2H) ppm.

Example 158

4-(1-Methyl-piperidin-4-yl)piperazine-1-carboxylic acid 5-cyano-3-(2-ethoxy-phenyl)-2-oxo-1-(quinoline-8-sulfonyl)-2,3-dihydro-1H-indol-3-yl ester $^1$H-NMR (CDCl$_3$): δ=1.25 (3H), 1.40-1.75 (5H), 1.90 (2H), 2.10-2.30 (5H), 2.45 (2H), 2.60 (2H), 2.9 (2H), 3.45 (2H), 3.70 (1H), 4.05 (1H), 6.75 (1H), 6.95 (1H), 7.20 (1H), 7.30 (1H), 7.40 (1H), 7.60-7.80 (3H), 8.05 (1H), 8.15 (1H), 8.50 (1H), 8.70 (1H) and 8.75 (1H) ppm.

Example 159

4-(1-Methyl-piperidin-4-yl)piperazine-1-carboxylic acid 5-chloro-3-(2-methoxy-pyridin-3-yl)-2-oxo-1-(thiophene-2-sulfonyl)-2,3-dihydro-1H-indol-3-yl ester $^1$H NMR (400 MHz, DMSO-d$_6$) δ 8.20 (3H), 8.00 (1H), 7.75 (1H), 7.50 (1H), 7.30 (2H), 7.20 (1H), 3.60 (2H), 3.35 (3H), 3.10 (2H), 2.75 (2H), 2.35 (2H), 2.10 (4H), 1.80 (2H), 1.65 (2H), 1.35 (4H); MS (API-ES, pos) m/z=646 [M+H]

Example 160

4-(1-Methyl-piperidin-4-yl)-piperazine-1-carboxylic acid 5-methoxy-3-(2-methoxy-pyridin-3-yl)-2-oxo-1-(pyridine-2-sulfonyl)-2,3-dihydro-1H-indol-3-yl ester $^1$H-NMR (400 MHz, CDCl$_3$) δ (ppm): 8.73 (1H, d), 8.32 (1H, d), 8.11 (1H, m), 8.00-7.84 (3H, m), 7.56-7.45 (1H, m), 6.94 (1H, t), 6.86 (1H, d), 6.52 (1H, s), 3.73 (1H, d), 3.70 (3H, s), 3.56 (2H, s br.), 3.14 (2H, q br.), 2.94 (2H, d br.), 2.65-1.47 (13H, m br.); MS (API-ES, pos) m/z=637 [M+H]

Example 161

4-(4-Methyl-piperazin-1-yl)-piperidine-1-carboxylic acid 5-methoxy-3-(2-methoxy-pyridin-3-yl)-2-oxo-1-(pyridine-2-sulfonyl)-2,3-dihydro-1H-indol-3-yl ester $^1$H-NMR (400 MHz, CDCl$_3$) δ (ppm): 8.74 (1H, d), 8.32 (1H, d), 8.11 (1H, m), 8.00-7.86 (3H, m), 7.56-7.50 (1H, m), 6.94 (1H, t), 6.86 (1H, d), 6.52 (1H, s), 3.73 (3H, s), 3.70 (3H, s), 3.56 (2H, s br.), 3.13 (2H, q br.), 2.91 (2H, d br.), 2.65-1.39 (13H, m br.); MS (API-ES, pos) m/z=637 [M+H]

Example 162

4-(1-Methyl-piperidin-4-yl)-piperazine-1-carboxylic acid 5-cyano-3-(2-methoxy-pyridin-3-yl)-2-oxo-1-(thiophene-2-sulfonyl)-2,3-dihydro-1H-indol-3-yl ester $^1$H NMR (400 MHz, DMSO-d$_6$) δ 8.20 (3H), 8.05 (1H), 7.95 (2H), 7.75 (1H), 7.30 (1H), 7.20 (1H), 3.60 (2H), 3.10 (2H), 2.80 (2H), 2.35 (2H), 2.15 (4H), 2.00 (1H), 1.85 (2H), 1.65 (2H), 1.35 (3H); MS (API-ES, pos) m/z=637 [M+H]

Example 163

4-(1-Methyl-piperidin-4-yl)-piperazine-1-carboxylic acid 5-chloro-1-(4,5-dichloro-thiophene-2-sulfonyl)-3-(2-methoxy-pyridin-3-yl)-2-oxo-2,3-dihydro-1H-indol-3-yl ester diacetate MS (ESI, pos) m/z=716 [M+H]

Example 164

4-(1-Methyl-piperidin-4-yl)-piperazine-1-carboxylic acid 5-chloro-1-(5-chloro-thiophene-2-sulfonyl)-3-(2-methoxy-pyridin-3-yl)-2-oxo-2,3-dihydro-1H-indol-3-yl ester diacetate MS (ESI, pos) m/z=680 [M+H]

Example 165

4-(1-Methyl-piperidin-4-yl)-piperazine-1-carboxylic acid 5-chloro-3-(2-methoxy-pyridin-3-yl)-1-(1-methyl-1H-imidazole-4-sulfonyl)-2-oxo-2,3-dihydro-1H-indol-3-yl ester diacetate MS (ESI, pos) m/z=646 [M+H]

Example 166

4-(1-Methyl-piperidin-4-yl)-piperazine-1-carboxylic acid 5-chloro-1-(1,2-dimethyl-1H-imidazole-4-sulfonyl)-3-(2-methoxy-pyridin-3-yl)-2-oxo-2,3-dihydro-1H-indol-3-yl ester diacetate MS (ESI, pos) m/z=658 [M+H]

Example 167

4-(1-Methyl-piperidin-4-yl)-piperazine-1-carboxylic acid 5-chloro-3-(2-methoxy-pyridin-3-yl)-1-(4-methyl-thiophene-2-sulfonyl)-2-oxo-2,3-dihydro-1H-indol-3-yl ester diacetate MS (ESI, pos) m/z=660 [M+H]

Example 168

4-(1-Methyl-piperidin-4-yl)-piperazine-1-carboxylic acid 5-chloro-3-(2-methoxy-pyridin-3-yl)-1-(5-methyl-thiophene-2-sulfonyl)-2-oxo-2,3-dihydro-1H-indol-3-yl ester diacetate MS (ESI, pos) m/z=660 [M+H]

Example 169

4-(1-Methyl-piperidin-4-yl)-piperazine-1-carboxylic acid 5-chloro-1-(2,5-dimethyl-thiophene-3-sulfonyl)-3-(2-methoxy-pyridin-3-yl)-2-oxo-2,3-dihydro-1H-indol-3-yl ester diacetate MS (ESI, pos) m/z=674 [M+H]

Example 170

4-(1-Methyl-piperidin-4-yl)-piperazine-1-carboxylic acid 1-(benzo[b]thiophene-3-sulfonyl)-5-chloro-3-(2-methoxy-pyridin-3-yl)-2-oxo-2,3-dihydro-1H-indol-3-yl ester diacetate MS (ESI, pos) m/z=696 [M+H]

Example 171

4-(1-Methyl-piperidin-4-yl)-piperazine-1-carboxylic acid 5-chloro-3-(2-methoxy-pyridin-3-yl)-2-oxo-1-(thiophene-3-sulfonyl)-2,3-dihydro-1H-indol-3-yl ester diacetate MS (ESI, pos) m/z=646 [M+H]

Example 172

4-(1-Methyl-piperidin-4-yl)-piperazine-1-carboxylic acid 1-(benzo[b]thiophene-2-sulfonyl)-5-chloro-3-(2-methoxy-pyridin-3-yl)-2-oxo-2,3-dihydro-1H-indol-3-yl ester diacetate MS (ESI, pos) m/z=696 [M+H]

Example 173

4-(4-Methyl-piperazin-1-yl)-piperidine-1-carboxylic acid 5-chloro-3-(3-methyl-thiophen-2-yl)-2-oxo-1-(quinoline-8-sulfonyl)-2,3-dihydro-1H-indol-3-yl ester dihydrochloride $^1$H-NMR (D$_6$-DMSO): δ=1.4-1.6 (3H), 1.8-2.1 (3H), 2.8-3.6 (15H), 3.7 (1H), 4.1 (1H), 6.6 (1H), 6.95 (1H), 7.2-7.4 (3H), 7.55 (2H), 7.95 (1H), 8.0-8.2 (2H) and 8.5 (1H) ppm.

Example 174

4-(1-Methyl-piperidin-4-yl)-piperazine-1-carboxylic acid 5-chloro-3-(3-methyl-thiophen-2-yl)-2-oxo-1-(quinoline-8-sulfonyl)-2,3-dihydro-1H-indol-3-yl ester $^1$H-NMR (CDCl$_3$): δ=1.4 (2H), 1.65 (2H), 1.8-2.0 (5H), 2.05-2.15 (4H), 2.35 (2H), 2.45 (2H), 2.8 (2H), 3.05 (2H), 3.4 (2H), 6.8 (1H), 7.3 (1H), 7.4 (1H), 7.55 (1H), 7.65 (1H), 7.8 (1H), 8.0 (1H), 8.4 (1H), 8.5 (2H) and 8.6 (1H) ppm.

Example 175

Benzyl-methyl-carbamic acid 5-chloro-3-(2-methoxy-phenyl)-2-oxo-1-(quinoline-8-sulfonyl)-2,3-dihydro-1H-indol-3-yl ester

Example 176

4-Benzyl-piperazine-1-carboxylic acid 5-chloro-3-(2-methoxy-phenyl)-2-oxo-1-(quinoline-8-sulfonyl)-2,3-dihydro-1H-indol-3-yl ester

Example 177

4-Methyl-piperazine-1-carboxylic acid 5-chloro-3-(2-methoxy-phenyl)-2-oxo-1-(thiophene-2-sulfonyl)-2,3-dihydro-1H-indol-3-yl ester

Example 178

Pyridin-4-ylmethyl-carbamic acid 5-chloro-1-(2,4-dimethoxy-benzenesulfonyl)-3-(3-methyl-thiophen-2-yl)-2-oxo-2,3-dihydro-1H-indol-3-yl ester

Example 179

Benzyl-carbamic acid 5-chloro-1-(2,4-dimethoxy-benzenesulfonyl)-3-(3-methyl-thiophen-2-yl)-2-oxo-2,3-dihydro-1H-indol-3-yl ester

Example 180

Pyridin-4-ylmethyl-carbamic acid 5-chloro-3-(2-methoxy-phenyl)-2-oxo-1-(thiophene-2-sulfonyl)-2,3-dihydro-1H-indol-3-yl ester

Example 181

(3-Imidazol-1-yl-propyl)-carbamic acid 5-chloro-1-(2,4-dimethoxy-benzenesulfonyl)-3-(3-methyl-thiophen-2-yl)-2-oxo-2,3-dihydro-1H-indol-3-yl ester

Example 182

(3-Morpholin-4-yl-propyl)-carbamic acid 5-chloro-1-(2,4-dimethoxy-benzenesulfonyl)-3-(3-methyl-thiophen-2-yl)-2-oxo-2,3-dihydro-1H-indol-3-yl ester

Example 183

4-Benzoylamino-piperidine-1-carboxylic acid 5-chloro-3-(2-methoxy-phenyl)-2-oxo-1-(quinoline-8-sulfonyl)-2,3-dihydro-1H-indol-3-yl ester

Example 184

3-Phenyl-piperidine-1-carboxylic acid 5-chloro-3-(2-methoxy-phenyl)-2-oxo-1-(quinoline-8-sulfonyl)-2,3-dihydro-1H-indol-3-yl ester

Example 185

1,3-Dihydro-isoindole-2-carboxylic acid 5-chloro-3-(2-methoxy-phenyl)-2-oxo-1-(quinoline-8-sulfonyl)-2,3-dihydro-1H-indol-3-yl ester

Example 186

4-Phenyl-piperidine-1-carboxylic acid 5-chloro-3-(2-methoxy-phenyl)-2-oxo-1-(quinoline-8-sulfonyl)-2,3-dihydro-1H-indol-3-yl ester

Example 187

(2-Diethylamino-ethyl)-carbamic acid 5-chloro-3-(2-methoxy-phenyl)-2-oxo-1-(quinoline-8-sulfonyl)-2,3-dihydro-1H-indol-3-yl ester hydrochloride

Example 188

(2-Dimethylamino-ethyl)-carbamic acid 5-chloro-3-(3-methyl-thiophen-2-yl)-2-oxo-1-(quinoline-8-sulfonyl)-2,3-dihydro-1H-indol-3-yl ester

Example 189

4-Methyl-piperazine-1-carboxylic acid 5-chloro-1-(2,4-dimethoxy-benzenesulfonyl)-3-(3-methyl-pyridin-2-yl)-2-oxo-2,3-dihydro-1H-indol-3-yl ester

Example 190

Dimethyl-carbamic acid 5-chloro-1-(2,4-dimethoxy-benzenesulfonyl)-3-(3-methyl-pyridin-2-yl)-2-oxo-2,3-dihydro-1H-indol-3-yl ester

Example 191

(2-Pyridin-4-yl-ethyl)-carbamic acid 5-chloro-3-(3-methyl-thiophen-2-yl)-2-oxo-1-(quinoline-8-sulfonyl)-2,3-dihydro-1H-indol-3-yl ester

Example 192

6-Methoxy-3,4-dihydro-1H-isoquinoline-2-carboxylic acid 5-chloro-3-(2-methoxy-phenyl)-2-oxo-1-(quinoline-8-sulfonyl)-2,3-dihydro-1H-indol-3-yl ester

Example 193

(4-Cyano-thiazol-2-ylmethyl)-carbamic acid 5-chloro-3-(2-methoxy-phenyl)-2-oxo-1-(quinoline-8-sulfonyl)-2,3-dihydro-1H-indol-3-yl ester

Example 194

Dimethyl-carbamic acid 5-chloro-3-(2,4-dimethoxy-pyrimidin-5-yl)-2-oxo-1-(quinoline-8-sulfonyl)-2,3-dihydro-1H-indol-3-yl ester

Example 195

4-Isopropyl-piperazine-1-carboxylic acid 5-chloro-3-(2,4-dimethoxy-pyrimidin-5-yl)-2-oxo-1-(quinoline-8-sulfonyl)-2,3-dihydro-1H-indol-3-yl ester

Example 196

(5-Dimethylamino-pentyl)-carbamic acid 1-benzenesulfonyl-5-chloro-3-(2-methoxy-pyridin-3-yl)-2-oxo-2,3-dihydro-1H-indol-3-yl ester

Example 197

4-(2-Morpholin-4-yl-ethyl)piperazine-1-carboxylic acid 1-benzenesulfonyl-5-chloro-3-(2-methoxy-pyridin-3-yl)-2-oxo-2,3-dihydro-1H-indol-3-yl ester

Example 198

4-(2-Imidazol-1-yl-ethyl)-piperazine-1-carboxylic acid 1-benzenesulfonyl-5-chloro-3-(2-methoxy-pyridin-3-yl)-2-oxo-2,3-dihydro-1H-indol-3-yl ester

Example 199

4-(1-Methyl-piperidin-4-yl)-piperazine-1-carboxylic acid 3-benzofuran-7-yl-5-chloro-1-(2,4-dimethoxy-benzenesulfonyl)-2-oxo-2,3-dihydro-1H-indol-3-yl ester dihydrochloride

Example 200

4-(1-Methyl-piperidin-4-yl)-piperazine-1-carboxylic acid 2-oxo-1-(thiophene-2-sulfonyl)-3-o-tolyl-2,3-dihydro-1H-indol-3-yl ester dihydrochloride

Example 201

4-(4-Methyl-piperazin-1-yl)-piperidine-1-carboxylic acid 2-oxo-1-(thiophene-2-sulfonyl)-3-o-tolyl-2,3-dihydro-1H-indol-3-yl ester dihydrochloride

Example 202

4-(1-Methyl-piperidin-4-yl)-piperazine-1-carboxylic acid 1-(2,4-dimethyl-thiazole-5-sulfonyl)-5-methoxy-2-oxo-3-o-tolyl-2,3-dihydro-1H-indol-3-yl ester dihydrochloride

Example 203

4-(1-Methyl-piperidin-4-yl)-piperazine-1-carboxylic acid 1-(2,5-dimethyl-thiophene-3-sulfonyl)-3-(2-isopropoxy-phenyl)-5-methoxy-2-oxo-2,3-dihydro-1H-indol-3-yl ester dihydrochloride

Example 204

4-(1-Methyl-piperidin-4-yl)-piperazine-1-carboxylic acid 3-(2-isopropoxy-phenyl)-5-methoxy-1-(1-methyl-1H-imidazole-4-sulfonyl)-2-oxo-2,3-dihydro-1H-indol-3-yl ester dihydrochloride

Example 205

4-(1-Methyl-piperidin-4-yl)-piperazine-1-carboxylic acid 1-(2,5-dimethyl-thiophene-3-sulfonyl)-3-(2-ethoxy-phenyl)-5-methoxy-2-oxo-2,3-dihydro-1H-indol-3-yl ester dihydrochloride

Example 206

4-(1-Methyl-piperidin-4-yl)-piperazine-1-carboxylic acid 1-(2,5-dimethyl-thiophene-3-sulfonyl)-5-methoxy-2-oxo-3-(2-propoxy-phenyl)-2,3-dihydro-1H-indol-3-yl ester dihydrochloride

Example 207

4-(1-Methyl-piperidin-4-yl)-piperazine-1-carboxylic acid 5-methoxy-2-oxo-3-(2-propoxy-phenyl)-1-(thiophene-2-sulfonyl)-2,3-dihydro-1H-indol-3-yl ester dihydrochloride

Example 208

4-(1-Methyl-piperidin-4-yl)-piperazine-1-carboxylic acid 3-(2-ethoxy-phenyl)-5-fluoro-1-(1-methyl-1H-imidazole-4-sulfonyl)-2-oxo-2,3-dihydro-1H-indol-3-yl ester

Example 209

4-(1-Methyl-piperidin-4-yl)-piperazine-1-carboxylic acid 1-(1,2-dimethyl-1H-imidazole-4-sulfonyl)-3-(2-ethoxy-phenyl)-5-fluoro-2-oxo-2,3-dihydro-1H-indol-3-yl ester

Example 210

4-(1-Methyl-piperidin-4-yl)-piperazine-1-carboxylic acid 1-(3,5-dimethyl-isoxazole-4-sulfonyl)-3-(2-ethoxy-phenyl)-5-fluoro-2-oxo-2,3-dihydro-1H-indol-3-yl ester

Example 211

4-(1-Methyl-piperidin-4-yl)-piperazine-1-carboxylic acid 1-(2,5-dimethyl-thiophene-3-sulfonyl)-3-(2-ethoxy-phenyl)-5-fluoro-2-oxo-2,3-dihydro-1H-indol-3-yl ester

Example 212

4-(1-Methyl-piperidin-4-yl)-piperazine-1-carboxylic acid 3-(2-ethoxy-phenyl)-5-fluoro-1-(3-methoxy-thiophene-2-sulfonyl)-2-oxo-2,3-dihydro-1H-indol-3-yl ester

Example 213

4-(1-Methyl-piperidin-4-yl)-piperazine-1-carboxylic acid 1-(2,4-dimethyl-thiazole-5-sulfonyl)-3-(2-ethoxy-phenyl)-5-fluoro-2-oxo-2,3-dihydro-1H-indol-3-yl ester dihydrochloride

Example 214

4-(1-Methyl-piperidin-4-yl)-piperazine-1-carboxylic acid [1-(3,5-dimethyl-isoxazole-4-sulfonyl)-3-(2-ethoxy-phenyl)-5-methoxy-2-oxo-2,3-dihydro-1H-indol-3-yl]-amide

Example 215

4-(1-Methyl-piperidin-4-yl)-piperazine-1-carboxylic acid [1-(5-chloro-thiophene-2-sulfonyl)-3-(2-ethoxy-phenyl)-5-methoxy-2-oxo-2,3-dihydro-1H-indol-3-yl]-amide

Example 216

4-(1-Methyl-piperidin-4-yl)-piperazine-1-carboxylic acid [1-(2,5-dimethyl-thiophene-3-sulfonyl)-3-(2-ethoxy-phenyl)-5-methoxy-2-oxo-2,3-dihydro-1H-indol-3-yl]-amide

Example 217

4-(1-Methyl-piperidin-4-yl)-piperazine-1-carboxylic acid 5-cyano-3-(2-ethoxy-phenyl)-2-oxo-1-(thiophene-3-sulfonyl)-2,3-dihydro-1H-indol-3-yl ester

Example 218

4-(1-Methyl-piperidin-4-yl)-piperazine-1-carboxylic acid [5-cyano-3-(2-ethoxy-phenyl)-2-oxo-1-(thiophene-3-sulfonyl)-2,3-dihydro-1H-indol-3-yl]-amide dihydrochloride Unless stated otherwise, the following examples bearing amines in the 3-position of the oxindole core can be synthesized according to synthesis scheme 1 in analogous fashion to Examples 1 to 6.

The amide derivatives of amino acids were acquired from commercial suppliers or synthesized according to standard methods, for example according to the following procedure:

(S)—N,N-Dimethyl-2-methylamino-propionamide hydrochloride

To a solution of (S)-Boc-N-Me-Ala-OH (9.8 mmol, 2.00 g, from Bachem) in DMF (10 mL) were added 1-Hydroxy-1H-benzotriazole (10.8 mmol, 1.46 g) and EDCI (10.8 mmol, 2.08 g). The reaction mixture was stirred for 10 min before a 2M solution of dimethylamine in THF (11.8 mmol, 5.9 mL) was added. After stirring for 18 h at room temperature, water was added and the mixture was extracted several times with ethyl acetate. The combined organic layers were washed with 1N aqueous hydrochloric acid, aqueous sodium bicarbonate solution and water. After drying over magnesium sulfate, the volatiles were removed in vacuo. Yield: 1.86 g of a colorless oil (82%). The Boc-protected coupling product was dissolved in MeOH (19 mL) and treated with a 4N solution of HCl in dioxane (32.3 mmol, 8.1 mL). After stirring for 18 h at room temperature, the reaction mixture was evaporated to dryness to leave 1.41 g of a white solid (quantitative yield).

(S)-Pyrrolidine-2-carboxylic acid dimethylamide hydrochloride, (S)-Pyrrolidine-2-carboxylic acid methylamide hydrochloride, (S)-Piperidine-2-carboxylic acid dimethylamide hydrochloride, (S)-Azetidine-2-carboxylic acid dimethylamide hydrochloride, (S)-2,5-Dihydro-1H-pyrrole-2-carboxylic acid dimethylamide hydrochloride, (2S,4R)-4-Fluoro-pyrrolidine-2-carboxylic acid dimethylamide hydrochloride, (2S,4S)-4-Hydroxy-pyrrolidine-2-carboxylic acid dimethylamide hydrochloride, (2S,4R)-4-Hydroxy-piperidine-2-carboxylic acid dimethylamide hydrochloride, N,N-Dimethyl-2-methylamino-acetamide hydrochloride, 2-Amino-N,N-dimethyl-acetamide hydrochloride, Pyrrolidine-3-carboxylic acid dimethylamide hydrochloride, (S)-2-Amino-N,N-dimethyl-propionamide hydrochloride, (S)-2-Amino-N,N-dimethyl-butyramide hydrochloride were prepared in analogous fashion.

Example 220

(S)-2-{[5-Chloro-1-(2,4-dimethoxy-benzenesulfonyl)-3-(2-methoxy-pyridin-3-yl)-2-oxo-2,3-dihydro-1H-indol-3-yl]-methyl-amino}-N,N-dimethyl-propionamide, levorotatory diastereomer $[\alpha]_D^{20°\,C.}$ (c=0.1, CHCl$_3$): −197;
$^1$H NMR (400 MHz, DMSO-d$_6$) δ 8.10 (1H), 7.95 (2H), 7.85 (1H), 7.50 (1H), 7.15 (1H), 6.90 (1H), 6.75 (2H), 4.00 (1H), 3.85 (3H), 3.75 (3H), 3.25 (3H), 2.75 (3H), 2.35 (3H), 0.90 (3H); MS (API-ES, pos) m/z=603 [M+H]

Example 221

(S)-2-[5-Chloro-1-(2,4-dimethoxy-benzenesulfonyl)-3-(2-methoxy-pyridin-3-yl)-2-oxo-2,3-dihydro-1H-indol-3-ylamino]-N,N-dimethyl-propionamide, levorotatory diastereomer $[\alpha]_D^{20°\,C.}$ (c=0.1, CHCl$_3$): −152;
$^1$H NMR (400 MHz, DMSO-d$_6$) δ 8.20 (1H), 8.10 (1H), 7.95 (1H), 7.85 (1H), 7.50 (1H), 7.10 (1H), 7.00 (1H), 6.80 (1H), 6.75 (1H), 3.90 (1H), 3.80 (3H), 3.40 (2H), 3.25 (3H), 2.75 (3H), 2.65 (3H), 0.90 (3H); MS (API-ES, pos) m/z=589 [M+H]

Example 222

(2S,4R)-1-[5-Chloro-1-(2,4-dimethoxy-benzenesulfonyl)-3-(3-methyl-pyridin-2-yl)-2-oxo-2,3-dihydro-1H-indol-3-yl]-4-hydroxy-pyrrolidine-2-carboxylic acid dimethylamide, levorotatory diastereomer $^1$H-NMR (D$_6$-DMSO): δ=1.65 (1H), 1.9 (3H), 2.0 (1H), 2.45 (3H), 2.6 (3H), 2.65 (1H), 3.3 (1H), 3.5 (3H), 3.9 (3H), 4.3 (1H), 4.7 (1H), 5.6 (1H), 6.7 (1H), 6.75 (1H), 7.1 (1H), 7.25 (1H), 7.45 (1H), 7.55 (1H), 7.75 (1H), 7.95 (1H) and 8.15 (1H) ppm.

Example 223

(2S,4R)-1-[1-Benzenesulfonyl-5-chloro-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.45 (1H), 8.25 (2H), 8.10 (1H), 7.70-7.90 (4H), 7.45 (1H), 7.10 (1H), 7.05 (1H), 5.00 (1H), 4.45 (1H), 4.27 (1H), 3.25 (1H), 2.95 (3H), 2.70 (1H), 2.40 (3H), 2.05 (1H), 1.70 (1H); MS (API-ES, pos) m/z=571 [M+H]

Example 224

(2S,4R)-1-[5-Chloro-1-(2,4-dimethoxy-benzenesulfonyl)-2-oxo-3-(2-oxo-1,2-dihydro-pyridin-3-yl)-2,3-dihydro-1H-indol-3-yl]-4-hydroxy-pyrrolidine-2-carboxylic acid dimethylamide, levorotatory diastereomer A solution of example 5 (0.16 mmol, 100 mg) and sodium iodide (0.32 mmol, 109 mg) in acetic acid (1 mL) was heated overnight at 40° C. The reaction mixture was diluted with ethyl acetate and washed with aqueous sodium dithionate solution, water and brine. The organic layer was dried over magnesium sulfate and concentrated in vacuo. Chromatographic purification over silica gel (gradient from 4% to 12% MeOH in dichloromethane) yielded 59 mg (60%) of a white crystalline solid.

$^1$H NMR (400 MHz, DMSO-d$_6$) δ 11.55 (1H), 7.90 (2H), 7.70 (1H), 7.40 (1H), 7.30 (1H), 7.00 (1H), 6.70 (1H), 6.65 (1H), 6.70 (1H), 4.90 (1H), 4.60 (1H), 4.30 (1H), 3.85 (3H), 3.55 (3H), 2.90 (1H), 2.60 (3H), 2.55 (3H), 2.25 (1H), 1.60 (1H); MS (API-ES, pos) m/z=617 [M+H]

Example 225

(2S,4R)-1-[1-(2,4-Dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer $[\alpha]_D^{20° C.}$ (c=0.1, CHCl$_3$): −285;
$^1$H NMR (400 MHz, DMSO-d$_6$) δ 8.20 (1H), 8.10 (1H), 8.00 (1H), 7.80 (1H), 7.37 (1H), 6.90-7.15 (3H), 6.77 (1H), 6.70 (1H), 4.90 (1H), 4.55 (1H), 4.45 (1H), 3.85 (3H), 3.70 (3H), 3.40 (3H), 2.85 (1H), 2.60 (3H), 2.35 (3H), 2.15 (1H), 1.30-1.70 (2H); MS (API-ES, pos) m/z=597 [M+H]

Example 226

(S)-1-[1-(2,4-Dimethoxy-benzenesulfonyl)-3-(2-methoxy-pyridin-3-yl)-2-oxo-2,3-dihydro-1H-indol-3-yl]-pyrrolidine-2-carboxylic acid dimethylamide, levorotatory diastereomer $[\alpha]_D^{20° C.}$ (c=0.1, CHCl$_3$): −210;
$^1$H NMR (400 MHz, DMSO-d$_6$) δ 8.10 (2H), 7.95 (1H), 7.80 (1H), 7.40 (1H), 7.15 (1H), 7.00 (2H), 6.77 (2H), 4.50 (1H), 3.87 (3H), 3.65 (3H), 3.50 (3H), 2.70 (3H), 2.40 (3H), 2.20 (1H), 1.75 (1H), 1.40 (3H); MS (API-ES, pos) m/z=581 [M+H]

Example 227

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid dimethylamide, levorotatory diastereomer $[\alpha]_D^{20° C.}$ (c=0.1, CHCl$_3$): −242;
$^1$H NMR (400 MHz, DMSO-d$_6$) δ 8.10 (2H), 7.95 (1H), 7.80 (1H), 7.50 (1H), 7.05 (2H), 6.80 (2H), 4.50 (1H), 3.87 (3H), 3.70 (3H), 3.50 (3H), 2.75 (1H), 2.70 (3H), 2.45 (3H), 2.20 (1H), 1.75 (1H), 1.40 (3H); MS (API-ES, pos) m/z=615 [M+H]

Example 228

(2S,4R)-1-[1-(2,4-Dimethoxy-benzenesulfonyl)-3-(2-methoxy-pyridin-3-yl)-5-methyl-2-oxo-2,3-dihydro-1H-indol-3-yl]-4-hydroxy-pyrrolidine-2-carboxylic acid dimethylamide fumarate, levorotatory diastereomer $[\alpha]_D^{° C.}$ (c=0.1, CHCl$_3$): −200;
$^1$H-NMR (400 MHz, DMSO-d$_6$) δ 8.15 (1H, s br.), 8.07 (1H, m), 7.97 (1H, d), 7.67 (1H, d), 7.17 (1H, d), 7.01 (1H, t), 6.86-6.66 (3H, m), 4.87 (1H, s), 4.56 (1H, d), 4.34 (1H, sext.), 3.86 (3H, s), 3.70 (3H, s), 2.59 (3H, s br.), 2.35 (3H, s), 2.21 (3H, s), 1.60 (1H, m); MS (API-ES, pos) m/z=611 [M+H]

Example 229

(2S,4R)-1-[1-Benzenesulfonyl-3-(2-methoxy-pyridin-3-yl)-5-methyl-2-oxo-2,3-dihydro-1H-indol-3-yl]-4-hydroxy-pyrrolidine-2-carboxylic acid dimethylamide fumarate, levorotatory diastereomer $^1$H-NMR (400 MHz, CDCl$_3$) δ 8.27 (1H, d), 8.22 (2H, s br.), 8.03 (1H, m), 7.79 (1H, d), 7.68 (1H, t), 7.60 (2H, m), 7.10 (1H, d), 6.90 (1H, t), 6.77 (1H, s), 4.74 (1H, s br.), 4.55 (1H, m), 3.22 (3H, s br.), 2.73 (3H, s br.), 2.42 (3H, s br.), 2.20 (3H, s), 1.94 (1H, m), 1.84 (1H, s br.); MS (API-ES, pos) m/z=551 [M+H]

Example 230

(2S,4R)-1-[1-(2,4-Dimethoxy-benzenesulfonyl)-5-methoxy-3-(2-methoxy-pyridin-3-yl)-2-oxo-2,3-dihydro-1H-indol-3-yl]-4-hydroxy-pyrrolidine-2-carboxylic acid dimethylamide fumarate, levorotatory diastereomer $[\alpha]_D^{20° C.}$ (c=0.1, CHCl$_3$): −137;

¹H-NMR (500 MHz, DMSO-d₆) δ 8.17 (1H, d), 8.06 (1H, d), 7.99 (1H, d), 7.70 (1H, d), 7.00 (1H, t), 6.94 (1H, d), 6.72 (1H, d), 6.70 (1H, s), 6.47 (1H, s), 4.70 (1H, s br.), 4.58 (1H, d), 4.36 (1H, s br.), 3.86 (3H, s), 3.72 (3H, s), 3.67 (3H, s), 3.42 (3H, s), 2.94 (1H, s br.), 2.60 (3H, m), 2.38 (3H, m), 2.20 (1H, s br.), 1.66-1.47 (2H, m); MS (API-ES, pos) m/z=627 [M+H]

Example 231

(2S,4R)-1-[1-Benzenesulfonyl-5-methoxy-3-(2-methoxy-pyridin-3-yl)-2-oxo-2,3-dihydro-1H-indol-3-yl]-4-hydroxy-pyrrolidine-2-carboxylic acid dimethylamide fumarate, levorotatory diastereomer $[\alpha]_D^{20°\ C.}$ (c=0.1, CHCl₃): −192;
¹H-NMR (500 MHz, DMSO-d₆) δ 8.37 (1H, m), 8.17 (2H, d), 8.02 (1H, m), 7.76 (1H, t), 7.68 (2H, t), 7.62 (1H, d), 7.02 (1H, t), 6.90 (1H, d), 6.44 (1H, s), 4.80 (1H, s br.), 4.47 (1H, m), 4.30 (1H, s br.), 3.64 (3H, s), 3.04 (3H, s), 2.60 (1H, m br.), 2.44 (6H, s), 1.96 (1H, s br.), 1.70 (1H, m); MS (API-ES, pos) m/z=567 [M+H]

Example 232

(2S,4R)-1-[5-Cyano-1-(2,4-dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer A) 3-Hydroxy-5-iodo-3-(2-methoxy-pyridin-3-yl)-1,3-dihydro-indol-2-one A 1.7 M solution of tert-butyllithium in pentane (35 ml, 60 mmol) was added to THF (100 ml) at −78° C. 2-Bromomesitylene (4.6 ml, 30 mmol) was added dropwise and the mixture stirred at −78° C. for 1 h. 2-Methoxypyridine (3.2 ml, 30 mmol) was added at −78° C. and then the mixture was stirred at 0° C. for 1.5 h. The ice-cold solution of the lithiated 2-methoxypyridine was transferred (via a transfer needle) into an ice-cold suspension of 5-iodoisatin (4.1 g, 15 mmol) in THF (150 ml). The reaction mixture was allowed to warm to room temperature and then saturated ammonium chloride solution was added. The mixture was extracted three times with ethyl acetate, and the collected extracts were washed with saturated brine. The organic phase was dried over magnesium sulfate, filtered and concentrated under reduced pressure. Purification by crystallization from dichloromethane yielded 2.9 g of the intermediate. MS (API-ES, pos) m/z=383 [M+H]

B) (2S,4R)-4-Hydroxy-1-[5-iodo-3-(2-methoxy-pyridin-3-yl)-2-oxo-2,3-dihydro-1H-indol-3-yl]-pyrrolidine-2-carboxylic acid dimethylamide The chlorination/amination sequence was performed as described for examples 5 and 6 (step B and C). The two diastereomers were separated by flash chromatography over silica gel (gradient from 4% to 10% MeOH in dichloromethane). The major diastereomer was the later eluting one and led to the required levorotatory product.

MS (API-ES, pos) m/z=523 [M+H]

C) (2S,4R)-1-[1-(2,4-Dimethoxy-benzenesulfonyl)-5-iodo-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer The sulfonylation was performed as described for example 5 (step D).
MS (API-ES, pos) m/z=723 [M+H]

D) Example 232

(2S,4R)-1-[5-Cyano-1-(2,4-Dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer A solution of Example 232C (0.69 mmol, 500 mg), zinc zyanide (0.69 mmol, 81 mg) and palladium(0)-tetrakis-triphenylphosphine (15 mg) in DMF (3 mL) was heated at 75° C. for 24 h. The reaction mixture was poured into water and extracted with ethyl acetate. The organic layer was washed with water and brine. After drying over magnesium sulfate, the volatiles were evaporated in vacuo. The remaining oil was triturated with dichloromethane and the white solid was collected by filtration. The crude product was purified by flash chromatography over silica gel (gradient from 4% to 10% MeOH in dichloromethane). Yield: 315 mg of the desired product as a white solid (73%).
¹H NMR (400 MHz, DMSO-d₆) δ 8.32 (1H), 8.08 (1H), 8.00 (1H), 7.92 (1H), 7.86 (1H), 7.54 (1H), 7.05 (1H), 6.72-6.80 (2H), 4.98 (1H), 4.55 (1H), 4.32 (1H), 3.88 (3H), 3.73 (3H), 3.03 (1H), 2.45 (3H), 1.55-1.80 (2H); MS (API-ES, pos) m/z=622 [M+H]

Example 233

(S)-1-[5-Cyano-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid dimethylamide, 1:1 mixture of diastereomers MS (API-ES, pos) m/z=606 [M+H]

Example 234

(2S,4R)-1-[5-Chloro-1-(2,4-dimethoxy-benzenesulfonyl)-3-(3-methoxy-pyridin-4-yl)-2-oxo-2,3-dihydro-1H-indol-3-yl]-4-hydroxy-pyrrolidine-2-carboxylic acid dimethylamide, levorotatory diastereomer A) 5-Chloro-3-hydroxy-3-(3-methoxy-pyridin-4-yl)-1,3-dihydro-indol-2-one A 1.7 M solution of tert-butyllithium in pentane (57.8 mL) was added to THF (200 ml) at −78° C. 2-Bromomesitylene (3.6 mL) was added dropwise, keeping the temperature below −60° C., and the mixture stirred at −78° C. for 1 h. 3-Methoxypyridine (3.6 mL) was added dropwise at −78° C. and then the mixture was allowed to warm to −5° C. over 2 h. The reaction mixture was re-cooled to −78° C. and a slurry of 5-chloroisatin (3.26 g) in THF (100 mL) was added portionwise keeping the temperature below −60° C. The reaction mixture was stirred at −78° C. for 1 h. The cooling bath was removed and the reaction mixture was stirred for 30 min. The reaction mixture was quenched with 10% aqueous ammonium chloride solution and extracted several times with ethyl acetate. The combined organic layers were washed with water, dried over magnesium sulfate and evaporated to low volume. Upon standing, 0.73 g of a pale yellow solid separated which was filtered off, washed with ethyl acetate and dried in vacuo.

The subsequent steps were performed in analogous fashion to Examples 5 and 6.

Example 234

$[\alpha]_D^{20°\,C.}$ (c=0.1, CHCl$_3$): −212;
$^1$H NMR (400 MHz, DMSO-d$_6$) δ 8.25 (2H), 8.00 (1H), 7.85 (1H), 7.75 (1H), 7.45 (1H), 7.00 (1H), 6.75 (2H), 4.95 (1H), 4.55 (1H), 4.35 (1H), 3.85 (3H), 3.75 (3H), 3.40 (3H), 3.00 (1H), 2.55 (3H), 2.40 (3H), 2.30 (1H), 1.65 (1H); MS (API-ES, pos) m/z=631 [M+H]

Example 235

(2S,4R)-1-[5-Chloro-1-(2,4-dimethoxy-benzenesulfonyl)-2-oxo-3-pyridin-2-yl-2,3-dihydro-1H-indol-3-yl]-4-hydroxy-pyrrolidine-2-carboxylic acid dimethylamide, levorotatory diastereomer $[\alpha]_D^{20°\,C.}$ (c=0.1, CHCl$_3$): −23;
$^1$H-NMR (400 MHz, CDCl$_3$) δ 8.13 (1H, d), 8.06 (1H, d), 7.99 (1H, d), 7.88 (1H, d), 7.70 (1H, t), 7.09 (1H, m), 6.61 (1H, dd), 6.47 (1H, s), 4.35 (1H, s br.), 3.98 (1H, m), 3.89 (3H, s), 3.54 (dd, 1H), 3.46 (3H, s), 2.74 (3H, s), 2.67 (1H, d), 2.55 (3H, s), 2.11 (1H, m), 1.91 (1H, m); MS (API-ES, pos) m/z=601 [M+H]

Example 236

(2S,4R)-1-[5-Chloro-3-(2,4-dimethoxy-pyrimidin-5-yl)-1-(4-methoxy-benzenesulfonyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.95 (1H), 8.10 (2H), 7.70 (1H), 7.40 (1H), 7.20 (3H), 5.05 (1H), 4.40 (1H), 4.25 (1H), 3.85 (6H), 3.25 (1H), 3.15 (3H), 2.75 (1H), 2.35 (3H), 2.00 (1H), 1.65 (1H); MS (API-ES, pos) m/z=632 [M+H]

Example 237

(S)-1-[5-Chloro-1-(2,4-dimethoxy-benzenesulfonyl)-3-(2-methoxy-pyridin-3-yl)-2-oxo-2,3-dihydro-1H-indol-3-yl]-piperidine-2-carboxylic acid dimethylamide, levorotatory diastereomer $[\alpha]_D^{20°\,C.}$ (c=0.1, CHCl$_3$): −195;
$^1$H NMR (400 MHz, DMSO-d$_6$) δ 8.20 (1H), 8.05 (1H), 7.95 (1H), 7.85 (1H), 7.50 (1H), 7.15 (1H), 6.85 (1H), 6.75 (2H), 3.70-3.95 (8H), 2.95 (3H), 2.65 (3H), 2.20 (3H), 1.85 (1H), 1.30-1.70 (5H); MS (API-ES, pos) m/z=629 [M+H]

Example 238

(2S,4R)-1-[5-Chloro-1-(2,4-dimethoxy-benzenesulfonyl)-3-(2,6-dimethoxy-pyridin-3-yl)-2-oxo-2,3-dihydro-1H-indol-3-yl]-4-hydroxy-pyrrolidine-2-carboxylic acid dimethylamide, levorotatory diastereomer A) 5-Chloro-3-hydroxy-3-(2,6-dimethoxy-pyridin-3-yl)-1,3-dihydro-indol-2-one To a stirred solution of 2,6-dimethoxypyridine (50 mmol, 6.61 mL) in THF (100 mL) was added slowly a 1.6 M solution of n-butyllithium in hexanes (55 mmol, 34.4 mL) at −78° C. The mixture was allowed to warm slowly to 10° C. and kept at this temperature for 30 min. The reaction mixture was re-cooled to −78° C. and a slurry of 5-chloroisatin (20 mmol, 3.63 g) in THF (150 mL) was added portionwise, keeping the temperature below 60° C. The reaction was allowed to come to room temperature. The mixture was quenched with 10% aqueous ammonium chloride solution and extracted several times with ethyl acetate. The combined organic layers were washed with water, dried over magnesium sulfate and evaporated in vacuo. Recrystallization from ethyl acetate yielded 4.56 g (71%) of the desired intermediate as a white crystalline solid (71%).

MS (API-ES, pos) m/z=321 [M+H]

The subsequent steps were performed as described for Example 5 and Example 6.

Example 238

$^1$H NMR (400 MHz, DMSO-d$_6$) δ 8.05 (1H), 8.00 (1H), 7.80 (1H), 7.45 (1H), 7.00 (1H), 6.75 (2H), 6.40 (1H), 4.90 (1H), 4.55 (1H), 4.30 (1H), 3.85 (3H), 3.80 (3H), 3.70 (3H), 3.40 (3H), 2.90 (1H), 2.55 (3H), 2.45 (3H), 2.20 (1H), 1.60 (2H); MS (API-ES, pos) m/z=661 [M+H]

Example 239

(2S,4R)-1-[5-Chloro-1-(2,4-dimethoxy-benzenesulfonyl)-3-(2-ethoxy-pyridin-3-yl)-2-oxo-2,3-dihydro-1H-indol-3-yl]-4-hydroxy-pyrrolidine-2-carboxylic acid dimethylamide, levorotatory diastereomer Example 239 was synthesized in analogy to Example 5, substituting 2-methoxypyridine with 2-ethoxypyridine in step A.

$[\alpha]_D^{20°\,C.}$ (c=0.1, CHCl$_3$): −228;
$^1$H NMR (400 MHz, DMSO-d$_6$) δ 8.20 (1H), 8.10 (1H), 8.00 (1H), 7.80 (1H), 7.45 (1H), 7.00 (2H), 6.75 (2H), 4.95 (1H), 4.55 (1H), 4.30 (1H), 3.95 (2H), 3.85 (3H), 3.70 (3H), 2.90 (1H), 2.55 (3H), 2.45 (3H), 2.25 (1H), 1.60 (1H), 0.80 (3H); MS (API-ES, pos) m/z=645 [M+H]

Example 240

(2S,4R)-1-[5-Chloro-1-(4-methoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.40 (1H), 8.15 (2H), 8.05 (1H), 7.70 (1H), 7.40 (1H), 7.20 (2H), 7.10 (1H), 7.00 (1H), 5.00 (1H), 4.45 (1H), 4.30 (1H), 3.85 (3H), 3.20 (1H), 3.05 (3H), 2.65 (1H), 2.40 (3H), 2.05 (1H), 1.65 (1H); MS (API-ES, pos) m/z=601 [M+H]

Example 241

(2S,4R)-1-[5-Chloro-1-(2-methoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide levorotatory diastereomer $^1$H NMR (400 MHz, DMSO-d$_6$) δ 8.25 (1H), 8.10 (2H), 7.75 (2H), 7.45 (1H), 7.30 (1H), 7.20 (1H), 7.05 (2H), 4.95 (1H), 4.55 (1H), 4.35 (1H), 3.75 (3H), 3.00 (1H), 2.55 (3H), 2.45 (3H), 2.25 (1H), 1.65 (2H); MS (API-ES, pos) m/z=601 [M+H]

Example 242

(2S,4R)-1-[5-Cyano-1-(4-methoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.50 (1H), 8.15 (2H), 8.10 (1H), 7.85 (2H), 7.50 (1H), 7.20 (2H), 7.10 (1H), 5.05 (1H), 4.45 (1H), 4.30 (1H), 3.85 (3H), 3.20 (1H), 3.05 (3H), 2.70 (1H), 2.35 (3H), 2.05 (1H), 1.65 (1H); MS (API-ES, pos) m/z=592 [M+H]

Example 243

(2S,4R)-1-[1-(2,4-Dimethoxy-benzenesulfonyl)-5-iodo-3-(3-methoxy-pyrazin-2-yl)-2-oxo-2,3-dihydro-1H-indol-3-yl]-4-hydroxy-pyrrolidine-2-carboxylic acid dimethylamide, levorotatory diastereomer $[α]_D^{20° C.}$ (c=0.1, CHCl$_3$): −9;
$^1$H-NMR (400 MHz, CDCl$_3$) δ 8.17 (1H, d), 8.12 (2H, dd), 7.72 (1H, d), 7.63 (1H, d), 7.16 (1H, s), 6.58 (1H, dd), 6.51 (1H, s), 5.48 (1H, s br.), 4.71 (1H, t), 4.26 (1H, s), 3.83 (6H, d), 3.59 (3H, s), 3.32 (1H, dd), 3.10 (1H, d), 2.88 (3H, s), 2.56 (3H, s), 2.22 (1H, m sym.), 1.74 (1H, m sym.)

Example 244

(2S,4R)-1-[1-(2,4-Dimethoxy-benzenesulfonyl)-3-(2,4-dimethoxy-pyrimidin-5-yl)-5-methoxy-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.70 (1H), 8.00 (1H), 7.65 (1H), 6.95 (1H), 6.75 (2H), 6.60 (1H), 4.90 (1H), 4.60 (1H), 4.30 (1H), 3.85 (6H), 3.70 (6H), 3.40 (3H), 3.00 (1H), 2.55 (3H), 2.45 (3H), 2.25 (1H), 1.65 (1H); MS (API-ES, pos) m/z=658 [M+H]

Example 245

(2S,4R)-1-[1-(2,4-Dimethoxy-benzenesulfonyl)-3-(2-methoxy-pyridin-3-yl)-2-oxo-5-trifluoromethoxy-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.25 (1H), 8.10 (1H), 8.00 (1H), 7.90 (1H), 7.45 (1H), 7.05 (1H), 7.00 (1H), 6.80 (1H), 6.75 (1H), 4.95 (1H), 4.55 (1H), 4.35 (1H), 3.85 (3H), 3.70 (3H), 3.40 (3H), 2.90 (1H), 2.60 (3H), 2.40 (3H), 2.20 (1H), 1.65 (1H); MS (API-ES, pos) m/z=681 [M+H]

Example 246

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-fluoro-pyrrolidine-2-carboxylic acid dimethylamide, levorotatory diastereomer $[α]_D^{20° C.}$ (c=0.1, CHCl$_3$): −207;
$^1$H NMR (400 MHz, DMSO-$d_6$) δ 8.20 (1H), 8.10 (1H), 8.00 (1H), 7.75 (1H), 7.45 (1H), 7.10 (2H), 6.75 (2H), 5.25 (1H), 4.60 (1H), 3.85 (3H), 3.75 (3H), 3.40 (1H), 3.25 (3H), 2.85 (1H), 2.45 (6H), 2.30 (1H), 1.85 (1H); MS (API-ES, pos) m/z=633 [M+H]

Example 247

(S)-1-[5-Chloro-1-(2,4-dimethoxy-benzenesulfonyl)-3-(2-methoxy-pyridin-3-yl)-2-oxo-2,3-dihydro-1H-indol-3-yl]-2,5-dihydro-1H-pyrrole-2-carboxylic acid dimethylamide, mixture of diastereomers MS (API-ES, pos) m/z=613 [M+H]

Example 248

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid methyl ester, mixture of diastereomers

Example 249

(S)-1-[5-Chloro-3-(6-chloro-2-methoxy-pyridin-3-yl)-1-(2,4-dimethoxy-benzenesulfonyl)-2-oxo-2,3-dihydro-1H-indol-3-yl]-pyrrolidine-2-carboxylic acid dimethylamide, mixture of diastereomers

Example 250

(2S,4R)-1-[1-(Benzo[b]thiophene-3-sulfonyl)-5-chloro-3-(2-methoxy-phenyl)-2-oxo-2,3-dihydro-1H-indol-3-yl]-4-hydroxy-pyrrolidine-2-carboxylic acid dimethylamide trifluoroacetate MS (ESI, pos) m/z=626 [M+H]

Example 251

(2S,4R)-1-[5-Chloro-3-(2-methoxy-phenyl)-1-(2-methyl-1,2,3,4-tetrahydro-isoquinoline-7-sulfonyl)-2-oxo-2,3-dihydro-1H-indol-3-yl]-4-hydroxy-pyrrolidine-2-carboxylic acid dimethylamide, levorotatory diastereomer Sodium acetoxyborohydride (0.36 mmol, 76.27 mg) was added to a solution of Example 61 (0.24 mmol, 0.15 g), acetic acid (0.24 mmol, 14.4 mg) and aq. formaldehyde (37%, 0.26 mmol, 21.42 mg). The mixture was stirred at RT for 12 h and evaporated in vacuo. The residue was solved in H$_2$O and extracted with ethyl acetate. The organic phase was dried, filtrated and evaporated. The crude product was then purified on a column of silicagel eluted with 5% MeOH in CH$_2$Cl$_2$ to afford 100 mg of the required product.
$[α]_D^{20° C.}$ (c=0.1, CHCl$_3$): −112;
MS (API-ES, pos) m/z=639 [M+H]

Example 252

(2S,4R)-1-[5-Chloro-3-(2-methoxy-phenyl)-1-(4-methyl-pyridine-2-sulfonyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-$d_6$) δ 8.65 (1H), 8.20 (1H), 8.00 (1H), 7.80 (1H), 7.65 (1H), 7.45 (1H), 7.30 (1H), 7.00

(1H), 6.95 (1H), 6.85 (1H), 4.95 (1H), 4.50 (1H), 4.30 (1H), 3.10 (3H), 2.40 (3H), 2.00 (1H), 1.65 (1H); MS (API-ES, pos) m/z=585 [M+H]

Example 253

(2S,4R)-1-[5-Chloro-3-(2-methoxy-phenyl)-1-(6-methyl-pyridine-2-sulfonyl)-2-oxo-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.20 (1H), 8.10 (1H), 8.00 (1H), 7.80 (1H), 7.65 (1H), 7.40 (1H), 7.30 (1H), 7.00 (1H), 6.95 (1H), 6.85 (1H), 4.90 (1H), 4.50 (1H), 4.30 (1H), 3.15 (3H), 2.55 (3H), 2.40 (4H), 1.60 (1H); MS (API-ES, pos) m/z=585 [M+H]

Example 254

(2S,4R)-1-[5-Fluoro-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.15 (1H), 8.10 (1H), 8.00 (1H), 7.70 (1H), 7.30 (2H), 7.20 (1H), 7.00 (1H), 6.80 (2H), 4.95 (1H), 4.50 (1H), 4.30 (1H), 2.95 (4H), 2.45 (3H), 2.00 (1H), 1.70 (1H); MS (API-ES, pos) m/z=560 [M+H]

Example 255

(S)-1-[5-Chloro-1-(2,4-dimethoxy-benzenesulfonyl)-3-(2-methoxy-pyridin-3-yl)-2-oxo-2,3-dihydro-1H-indol-3-yl]-azetidine-2-carboxylic acid dimethylamide, levorotatory diastereomer $^1$H NMR (400 MHz, DMSO-d$_6$) δ 8.10 (1H), 8.05 (2H), 7.85 (1H), 7.50 (1H), 7.00 (2H), 6.80 (2H), 4.80 (1H), 3.90 (3H), 3.75 (3H), 3.50 (3H), 2.80 (1H), 2.65 (4H), 2.35 (4H), 1.60 (1H); MS (API-ES, pos) m/z=601 [M+H]

Example 256

(2S,4R)-1-[5-Chloro-3-(2-methoxy-phenyl)-1-(3-methoxy-thiophene-2-sulfonyl)-2-oxo-2,3-dihydro-1H-indol-3-yl]-4-hydroxy-pyrrolidine-2-carboxylic acid dimethylamide, levorotatory diastereomer $[α]_D^{20° C.}$ (c=0.1, CHCl$_3$): −149;
$^1$H NMR (400 MHz, DMSO-d$_6$) δ 8.05 (1H), 7.85 (1H), 7.75 (1H), 7.40 (1H), 7.30 (1H), 7.15 (1H), 7.00 (1H), 6.90 (2H), 4.95 (1H), 4.55 (1H), 4.35 (1H), 3.85 (3H), 3.25 (3H), 2.35 (4H), 1.65 (1H); MS (API-ES, pos) m/z=606 [M+H]

Example 270

(2S,4R)-1-[5-Chloro-3-(2-methoxy-pyridin-3-yl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer $[α]_D^{20° C.}$ (c=0.1, CHCl$_3$): −110;
$^1$H NMR (400 MHz, DMSO-d$_6$) δ 8.45 (1H), 8.17 (1H), 8.07 (1H), 7.70 (2H), 7.43 (1H), 7.30 (1H), 7.03-7.15 (2H), 5.03 (1H), 4.45 (1H), 4.30 (1H), 3.25 (3H), 3.05 (3H), 2.70 (1H), 2.40 (3H), 2.05 (1H), 1.70 (1H); MS (API-ES, pos) m/z=577 [M+H]

Example 271

(2S,4R)-4-Hydroxy-1-[3-(2-methoxy-pyridin-3-yl)-1-(5-methyl-pyridine-2-sulfonyl)-2-oxo-2,3-dihydro-1H-indol-3-yl]-pyrrolidine-2-carboxylic acid dimethylamide, levorotatory diastereomer $^1$H NMR (400 MHz, DMSO-d$_6$) δ 8.85 (1H), 8.40 (1H), 8.00 (1H), 7.75 (1H), 7.45 (1H), 7.05 (1H), 6.95 (1H), 6.75 (2H), 4.95 (1H), 4.60 (1H), 4.35 (1H), 3.85 (3H), 3.75 (3H), 3.35 (3H), 3.00 (1H), 2.55 (3H), 2.45 (3H), 1.60 (2H); MS (API-ES, pos) m/z=552 [M+H]

Example 272

(2S,4R)-4-Hydroxy-1-[3-(2-methoxy-pyridin-3-yl)-5-methyl-2-oxo-1-(pyridine-2-sulfonyl)-2,3-dihydro-1H-indol-3-yl]-pyrrolidine-2-carboxylic acid dimethylamide fumarate, levorotatory diastereomer $[α]_D^{20° C.}$ (c=0.1, CHCl$_3$): −166;
$^1$H-NMR (500 MHz, DMSO-d$_6$) δ 8.79 (1H, d), 8.42 (2H, m), 8.28 (1H, t), 8.05 (1H, d), 7.77 (1H, m), 7.68 (1H, d), 7.14 (1H, d), 7.04 (1H, t), 6.77 (1H, s), 4.80 (1H, s), 4.44 (1H, m), 4.33 (1H, m), 3.25 (3H, s), 3.15 (3H, s), 2.58 (1H, s br.), 2.43 (3H, s), 2.39 (3H, s), 2.19 (3H, s), 1.85 (1H, s br.), 1.66 (1H, m); MS (API-ES, pos) m/z=552 [M+H]

Example 273

(2S,4R)-4-Hydroxy-1-[3-(2-methoxy-pyridin-3-yl)-5-methyl-2-oxo-1-(thiophene-2-sulfonyl)-2,3-dihydro-1H-indol-3-yl]-pyrrolidine-2-carboxylic acid dimethylamide fumarate, levorotatory diastereomer $[α]_D^{20° C.}$ (c=0.1, CHCl$_3$): −157;
$^1$H-NMR (400 MHz, CDCl$_3$) δ 8.25 (1H, s br.), 8.03 (2H, m), 7.72 (2H, m), 7.18 (1H, t), 7.09 (1H, d), 6.91 (1H, t), 6.81 (1H, s), 4.76 (1H, s br.), 4.57 (1H, m), 3.35 (3H, s br.), 2.72 (3H, s br.), 2.45 (3H, s), 2.22 (3H, s), 1.96 (2H, m); MS (API-ES, pos) m/z=557 [M+H]

Example 274

(2S,4R)-4-Hydroxy-1-[3-(2-methoxy-pyridin-3-yl)-5-methyl-1-(5-methyl-pyridine-2-sulfonyl)-2-oxo-2,3-dihydro-1H-indol-3-yl]-pyrrolidine-2-carboxylic acid dimethylamide fumarate, levorotatory diastereomer $[α]_D^{20° C.}$ (c=0.1, CHCl$_3$): −209;
$^1$H-NMR (400 MHz, CDCl$_3$) δ 8.54 (1H, s), 8.30 (1H, d), 8.20 (1H, s br.), 8.03 (1H, m), 7.80 (2H, m), 7.08 (1H, d), 6.90 (1H, t), 6.83 (1H, s), 4.74 (1H, s br.), 4.58 (1H, quint.), 3.58 (3H, s br.), 2.72 (3H, s br.), 2.44 (3H, s), 2.41 (3H, s), 2.21 (3H, s), 1.88 (1H, m), 1.68 (4H, s); MS (API-ES, pos) m/z=566 [M+H]

Example 275

(2S,4R)-4-Hydroxy-1-[5-methoxy-3-(2-methoxy-pyridin-3-yl)-2-oxo-1-(pyridine-2-sulfonyl)-2,3-dihydro-1H-indol-3-yl]-pyrrolidine-2-carboxylic acid dimethylamide fumarate, levorotatory diastereomer $[α]_D^{20° C.}$ (c=0.1, CHCl$_3$): −105;

¹H-NMR (400 MHz, DMSO-d₆) δ 8.81 (1H, d), 8.31 (1H, d), 8.22 (1H, t), 8.05 (1H, d), 7.82 (1H, m), 6.94 (1H, d), 6.48 (1H, s), 4.96 (1H, s br.), 4.47 (1H, s br.), 4.31 (1H, s br.), 3.66 (3H, s), 3.17 (3H, m), 2.38 (3H, s), 1.63 (1H, m); MS (API-ES, pos) m/z=568 [M+H]

Example 276

(2S,4R)-4-Hydroxy-1-[5-methoxy-3-(2-methoxy-pyridin-3-yl)-2-oxo-1-(thiophene-2-sulfonyl)-2,3-dihydro-1H-indol-3-yl]-pyrrolidine-2-carboxylic acid dimethylamide fumarate, levorotatory diastereomer $[\alpha]_D^{20°\,C.}$ (c=0.1, CHCl₃): −175;
¹H-NMR (400 MHz, DMSO-d₆) δ 8.41 (1H, s br.), 8.15 (1H, d), 8.04 (2H, m), 7.60 (1H, d), 7.30 (1H, t), 7.07 (1H, t), 6.92 (1H, d), 6.47 (1H, s), 4.99 (1H, s br.), 4.47 (1H, s br.), 4.31 (1H, s br.), 3.65 (3H, s), 3.02 (3H, s), 2.41 (6H, s), 2.00 (1H, m br.), 1.69 (1H, m); MS (API-ES, pos) m/z=573 [M+H]

Example 277

(2S,4R)-1-[5-Cyano-3-(2-methoxy-pyridin-3-yl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer ¹H NMR (400 MHz, DMSO-d₆) δ 8.50 (1H), 8.20 (1H), 8.15 (1H), 8.10 (1H), 7.85 (2H), 7.55 (1H), 7.35 (1H), 7.10 (1H), 5.05 (1H), 4.50 (1H), 4.30 (1H), 3.30 (1H), 3.05 (3H), 2.75 (1H), 2.35 (3H), 2.05 (1H), 1.70 (1H); MS (API-ES, pos) m/z=568 [M+H]

Example 278

(S)-1-[5-Chloro-3-(2-methoxy-pyridin-3-yl)-2-oxo-1-(thiophene-2-sulfonyl)-2,3-dihydro-1H-indol-3-yl]-pyrrolidine-2-carboxylic acid dimethylamide, levorotatory diastereomer $[\alpha]_D^{20°\,C.}$ (c=0.1, CHCl₃): −242;
¹H NMR (400 MHz, DMSO-d₆) δ 8.20 (1H), 8.10 (2H), 8.05 (1H), 7.75 (1H), 7.45 (1H), 7.35 (1H), 7.10 (2H), 4.40 (1H), 3.10 (3H), 3.05 (1H), 2.00 (1H), 1.60-1.90 (2H); MS (API-ES, pos) m/z=561 [M+H]

Example 279

(2S,4R)-4-Hydroxy-1-[5-methoxy-3-(2-methoxy-pyridin-3-yl)-1-(5-methyl-pyridine-2-sulfonyl)-2-oxo-2,3-dihydro-1H-indol-3-yl]-pyrrolidine-2-carboxylic acid dimethylamide fumarate m/z=582 [M+H]

Example 280

(2S,4R)-1-[5-Chloro-3-(2,6-dimethoxy-pyridin-3-yl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer ¹H NMR (400 MHz, DMSO-d₆) δ 8.30 (1H), 8.20 (1H), 8.10 (1H), 7.70 (1H), 7.40 (1H), 7.30 (1H), 7.05 (1H), 6.45 (1H), 5.00 (1H), 4.45 (1H), 4.30 (1H), 3.80 (3H), 3.25 (1H), 3.05 (3H), 2.70 (1H), 2.40 (3H), 2.00 (1H), 1.65 (1H); MS (API-ES, pos) m/z=607 [M+H]

Example 281

(2S,4R)-1-[5-Chloro-3-(2,4-dimethoxy-pyrimidin-5-yl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer ¹H NMR (400 MHz, DMSO-d₆) δ 8.95 (1H), 8.20 (1H), 8.10 (1H), 7.70 (1H), 7.45 (1H), 7.30 (1H), 7.25 (1H), 5.05 (1H), 4.45 (1H), 4.25 (1H), 3.90 (3H), 3.15 (3H), 2.80 (1H), 2.35 (3H), 2.05 (1H), 1.65 (1H); MS (API-ES, pos) m/z=608 [M+H]

Example 282

(2S,4R)-1-[5-Chloro-3-(2,4-dimethoxy-pyrimidin-5-yl)-1-(5-methyl-pyridine-2-sulfonyl)-2-oxo-2,3-dihydro-1H-indol-3-yl]-4-hydroxy-pyrrolidine-2-carboxylic acid dimethylamide, levorotatory diastereomer ¹H NMR (400 MHz, DMSO-d₆) δ 8.90 (1H), 8.65 (1H), 8.20 (1H), 8.05 (1H), 7.75 (1H), 7.45 (1H), 7.25 (1H), 5.05 (1H), 4.40 (1H), 4.25 (1H), 3.90 (3H), 3.25 (3H), 2.70 (1H), 2.45 (3H), 2.35 (3H), 2.00 (1H), 1.65 (1H); MS (API-ES, pos) m/z=617 [M+H]

Example 283

(2S,4R)-4-Hydroxy-1-[5-iodo-3-(3-methoxy-pyrazin-2-yl)-2-oxo-1-(thiophene-2-sulfonyl)-2,3-dihydro-1H-indol-3-yl]-pyrrolidine-2-carboxylic acid dimethylamide, levorotatory diastereomer $[\alpha]_D^{20°\,C.}$ (c=0.1, CHCl₃): −11;
¹H-NMR (400 MHz, CDCl₃) δ 8.14 (3H, m), 7.73 (1H, m), 7.66 (2H, s), 7.19 (1H, t), 7.12 (1H, s), 5.54 (1H, s br.), 4.58 (1H, t), 4.25 (1H, s), 3.40 (3H, s), 3.29 (1H, dd), 3.17 (1H, d), 2.80 (3H, s), 2.52 (3H, s), 2.27 (1H, m sym.), 1.70 (1H, m sym.); MS (API-ES, pos) m/z=671 [M+H]

Example 284

(2S,4R)-4-Hydroxy-1-[5-iodo-3-(3-methoxy-pyrazin-2-yl)-1-(5-methyl-pyridine-2-sulfonyl)-2-oxo-2,3-dihydro-1H-indol-3-yl]-pyrrolidine-2-carboxylic acid dimethylamide, levorotatory diastereomer $[\alpha]_D^{20°\,C.}$ (c=0.1, CHCl₃): −8;
¹H-NMR (400 MHz, CDCl₃) δ 8.55 (1H, s), 8.38 (1H, d), 8.12 (2H, m), 7.80 (2H, t), 7.65 (1H, d), 7.15 (1H, s), 4.56 (1H, t), 4.24 (1H, s), 3.52 (3H, s), 3.30 (1H, dd), 3.12 (1H, d), 2.77 (3H, s), 2.47 (6H, d), 2.26 (1H, m sym.), 1.71 (1H, m sym.); MS (API-ES, pos) m/z=679 [M+H]

Example 285

(2S,4R)-1-[5-Chloro-3-(2-methoxy-pyridin-3-yl)-1-(3-methoxy-thiophene-2-sulfonyl)-2-oxo-2,3-dihydro-1H-indol-3-yl]-4-hydroxy-pyrrolidine-2-carboxylic acid dimethylamide, levorotatory diastereomer ¹H NMR (400 MHz, DMSO-d₆) δ 8.35 (1H), 8.10 (2H), 7.80 (1H), 7.45 (1H), 7.20 (1H), 7.05 (1H), 7.00 (1H), 5.00 (1H), 4.50 (1H), 4.35 (1H), 3.90 (3H), 3.25 (3H), 3.15 (1H), 2.45 (3H), 1.85 (1H), 1.65 (1H); MS (API-ES, pos) m/z=607 [M+H]

Example 286

(2S,4R)-4-Hydroxy-1-[3-(2-methoxy-pyridin-3-yl)-1-(3-methoxy-thiophene-2-sulfonyl)-2-oxo-5-trifluoromethoxy-2,3-dihydro-1H-indol-3-yl]-pyrrolidine-2-carboxylic acid dimethylamide, levorotatory diastereomer $^1$H NMR (400 MHz, DMSO-d$_6$) δ 8.35 (1H), 8.10 (1H), 7.85 (1H), 7.40 (1H), 7.20 (1H), 7.05 (1H), 6.95 (1H), 5.00 (1H), 4.50 (1H), 4.35 (1H), 3.90 (3H), 3.25 (3H), 3.15 (1H), 2.40 (3H), 1.85 (1H), 1.70 (1H); MS (API-ES, pos) m/z=657 [M+H]

Example 287

(2S,4R)-1-[5-Chloro-3-(2,4-dimethoxy-pyrimidin-5-yl)-2-oxo-1-(quinoline-8-sulfonyl)-2,3-dihydro-1H-indol-3-yl]-4-hydroxy-pyrrolidine-2-carboxylic acid dimethylamide, mixture of the two diastereomers MS (API-ES, pos) m/z=653 [M+H]

Example 288

(2S,4R)-1-[5-Chloro-3-(2-methoxy-pyridin-3-yl)-2-oxo-1-(quinoline-8-sulfonyl)-2,3-dihydro-1H-indol-3-yl]-4-hydroxy-pyrrolidine-2-carboxylic acid dimethylamide, levorotatory diastereomer $^1$H NMR (400 MHz, DMSO-d$_6$) δ 8.85 (1H), 8.75 (1H), 8.60 (1H), 8.45 (1H), 8.30 (1H), 8.20 (1H), 8.05 (1H), 7.90 (1H), 7.70 (1H), 7.50 (1H), 7.00 (2H), 4.80 (1H), 4.55 (1H), 4.30 (1H), 3.05 (1H), 2.67 (3H), 1.55-1.90 (2H); MS (API-ES, pos) m/z=622 [M+H]

Example 289

(2S,4R)-1-[5-Chloro-3-(2,4-dimethoxy-pyrimidin-5-yl)-1-(5-methyl-pyridine-2-sulfonyl)-2-oxo-2,3-dihydro-1H-indol-3-yl]-4-hydroxy-pyrrolidine-2-carboxylic acid dimethylamide, levorotatory diastereomer $[\alpha]_D^{20\,°\,C.}$ (c=0.1, CHCl$_3$): −178;
$^1$H NMR (400 MHz, DMSO-d$_6$) δ 8.65 (1H), 8.40 (1H), 8.25 (1H), 8.10 (1H), 8.00 (1H), 7.80 (1H), 7.45 (1H), 7.05 (2H), 5.00 (1H), 4.45 (1H), 4.30 (1H), 3.20 (3H), 2.65 (1H), 2.45 (3H), 2.40 (3H), 2.38, 2.00 (1H), 1.65 (1H); MS (API-ES, pos) m/z=586 [M+H]

Example 302

5-Chloro-1-(2,4-dimethoxy-benzenesulfonyl)-3-(2-methoxy-pyridin-3-yl)-3-pyrrolidin-1-yl-1,3-dihydro-indol-2-one

Example 303

5-Chloro-3-(1,3-dihydro-isoindol-2-yl)-1-(2,4-dimethoxy-benzenesulfonyl)-3-(2-methoxy-pyridin-3-yl)-1,3-dihydro-indol-2-one

Example 304

5-Chloro-1-(2,4-dimethoxy-benzenesulfonyl)-3-((R)-3-hydroxy-pyrrolidin-1-yl)-3-(2-methoxy-pyridin-3-yl)-1,3-dihydro-indol-2-one

Example 305

3-Amino-5-chloro-1-(2,4-dimethoxy-benzenesulfonyl)-3-(2-methoxy-pyridin-3-yl)-1,3-dihydro-indol-2-one

Example 306

(2S,4R)-4-Hydroxy-1-[3-(2-methoxy-pyridin-3-yl)-2-oxo-1-(thiophene-2-sulfonyl)-2,3-dihydro-1H-indol-3-yl]-pyrrolidine-2-carboxylic acid dimethylamide, levorotatory diastereomer

Example 307

5-Chloro-1-(2,4-dimethoxy-benzenesulfonyl)-3-((S)-2-methoxymethyl-pyrrolidin-1-yl)-3-(2-methoxy-pyridin-3-yl)-1,3-dihydro-indol-2-one, levorotatory diastereomer

Example 308

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid amide, levorotatory diastereomer

Example 309

2-{[5-Chloro-1-(2,4-dimethoxy-benzenesulfonyl)-3-(2-methoxy-pyridin-3-yl)-2-oxo-2,3-dihydro-1H-indol-3-yl]-methyl-amino}-N,N-dimethyl-acetamide

Example 310

2-[5-Chloro-1-(2,4-dimethoxy-benzenesulfonyl)-3-(2-methoxy-pyridin-3-yl)-2-oxo-2,3-dihydro-1H-indol-3-ylamino]-N,N-dimethyl-acetamide

Example 311

(2S,4R)-1-[5-Chloro-3-(3-methyl-pyridin-2-yl)-2-oxo-1-(thiophene-2-sulfonyl)-2,3-dihydro-1H-indol-3-yl]-4-hydroxy-pyrrolidine-2-carboxylic acid dimethylamide methanesulfonate, levorotatory diastereomer

Example 312

(2S,4R)-1-[5-Chloro-1-(5-methyl-pyridine-2-sulfonyl)-3-(3-methyl-pyridin-2-yl)-2-oxo-2,3-dihydro-1H-indol-3-yl]-4-hydroxy-pyrrolidine-2-carboxylic acid dimethylamide methanesulfonate, levorotatory diastereomer

Example 313

5-Chloro-1-(2,4-dimethoxy-benzenesulfonyl)-3-(2-methoxy-pyridin-3-yl)-3-((S)-2-trifluoromethyl-pyrrolidin-1-yl)-1,3-dihydro-indol-2-one, levorotatory diastereomer

Example 314

5-Chloro-1-(2,4-dimethoxy-benzenesulfonyl)-3-(2-methoxy-pyridin-3-yl)-3-((S)-2-pyrrolidin-1-ylmethyl-pyrrolidin-1-yl)-1,3-dihydro-indol-2-one, levorotatory diastereomer

Example 315

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid tert-butyl ester, levorotatory diastereomer

Example 316

5-Chloro-1-(2,4-dimethoxy-benzenesulfonyl)-3-(2-methoxy-pyridin-3-yl)-3-[(S)-2-(4-methyl-piperazine-1-carbonyl)-pyrrolidin-1-yl]-1,3-dihydro-indol-2-one, levorotatory diastereomer

Example 317

(S)-4-[5-Chloro-1-(2,4-dimethoxy-benzenesulfonyl)-3-(2-methoxy-pyridin-3-yl)-2-oxo-2,3-dihydro-1H-indol-3-yl]-3-dimethylcarbamoyl-piperazine-1-carboxylic acid tert-butyl ester, levorotatory diastereomer

Example 318

(2S,4R)-1-[5-Chloro-3-(2-ethoxy-pyridin-3-yl)-2-oxo-1-(thiophene-2-sulfonyl)-2,3-dihydro-1H-indol-3-yl]-4-hydroxy-pyrrolidine-2-carboxylic acid dimethylamide, levorotatory diastereomer

Example 320

(S)-1-[5-Chloro-1-(2,4-dimethoxy-benzenesulfonyl)-3-(2-methoxy-pyridin-3-yl)-2-oxo-2,3-dihydro-1H-indol-3-yl]-piperazine-2-carboxylic acid dimethylamide trifluoroacetate

Example 321

(2S,4R)-1-[5-Cyano-3-(2-methoxy-pyridin-3-yl)-1-(5-methyl-pyridine-2-sulfonyl)-2-oxo-2,3-dihydro-1H-indol-3-yl]-4-hydroxy-pyrrolidine-2-carboxylic acid dimethylamide, levorotatory diastereomer

Example 322

5-Chloro-1-(2,4-dimethoxy-benzenesulfonyl)-3-(2-methoxy-pyridin-3-yl)-3-[(S)-2-(pyrrolidine-1-carbonyl)-pyrrolidin-1-yl]-1,3-dihydro-indol-2-one, levorotatory diastereomer

Example 324

(2S,4R)-1-[5-Chloro-3-(2,4-dimethoxy-pyrimidin-5-yl)-1-(3-methoxy-thiophene-2-sulfonyl)-2-oxo-2,3-dihydro-1H-indol-3-yl]-4-hydroxy-pyrrolidine-2-carboxylic acid dimethylamide, levorotatory diastereomer

Example 325

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid methylamide

Example 326

1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-3-carboxylic acid dimethylamide, mixture of diastereomers

Example 327

5-Chloro-1-(2,4-dimethoxy-benzenesulfonyl)-3-(2-dimethylamino-1-methyl-ethylamino)-3-(2-methoxy-pyridin-3-yl)-1,3-dihydro-indol-2-one, levorotatory diastereomer

Example 328

(S)-1-[5-Cyano-1-(4-methoxy-benzenesulfonyl)-3-(2-methoxy-pyridin-3-yl)-2-oxo-2,3-dihydro-1H-indol-3-yl]-pyrrolidine-2-carboxylic acid dimethylamide, levorotatory diastereomer

Example 329

(S)-1-[5-Cyano-3-(2-methoxy-pyridin-3-yl)-2-oxo-1-(thiophene-2-sulfonyl)-2,3-dihydro-1H-indol-3-yl]-pyrrolidine-2-carboxylic acid dimethylamide, levorotatory diastereomer

Example 330

(S)-2-[5-Chloro-1-(2,4-dimethoxy-benzenesulfonyl)-3-(2-methoxy-pyridin-3-yl)-2-oxo-2,3-dihydro-1H-indol-3-ylamino]-N,N-dimethyl-butyramide, levorotatory diastereomer

Example 331

(S)-1-[5-Chloro-1-(4-methoxy-benzenesulfonyl)-3-(2-methoxy-pyridin-3-yl)-2-oxo-2,3-dihydro-1H-indol-3-yl]-pyrrolidine-2-carboxylic acid dimethylamide, levorotatory diastereomer

Example 332

(2S,4R)-1-[5-Chloro-1-(4-methoxy-benzenesulfonyl)-3-(2-methoxy-pyridin-3-yl)-2-oxo-2,3-dihydro-1H-indol-3-yl]-4-fluoro-pyrrolidine-2-carboxylic acid dimethylamide, levorotatory diastereomer

Example 334

(2S,4R)-1-[5-Chloro-3-(2,6-dimethoxy-pyridin-3-yl)-1-(4-methoxy-benzenesulfonyl)-2-oxo-2,3-dihydro-1H-indol-3-yl]-4-hydroxy-pyrrolidine-2-carboxylic acid dimethylamide, levorotatory diastereomer

Example 335

1-[5-Cyano-3-(2-methoxy-phenyl)-2-oxo-1-(thiophene-2-sulfonyl)-2,3-dihydro-1H-indol-3-yl]-pyrrolidine-2-carboxylic acid dimethylamide, mixture ofdiastereomers

Example 336

(2S,4R)-1-[5-Chloro-3-(2-ethoxy-phenyl)-2-oxo-1-(thiophene-2-sulfonyl)-2,3-dihydro-1H-indol-3-yl]-4-hydroxy-pyrrolidine-2-carboxylic acid dimethylamide, mixture of diastereomers

Example 337

(2S,4R)-1-[5-Chloro-3-(2-ethoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide, levorotatory diastereomer

Example 339

(2S,4R)-1-[5-Cyano-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethylamide, mixture of diastereomers

Example 340

(2S,4R)-1-[5-Cyano-3-(2-methoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide, mixture of diastereomers

Example 341

(2S,4R)-1-[3-(2-Ethoxy-phenyl)-5-methoxy-1-(5-methyl-pyridine-2-sulfonyl)-2-oxo-2,3-dihydro-1H-indol-3-yl]-4-hydroxy-pyrrolidine-2-carboxylic acid dimethylamide, mixture of diastereomers

Example 342

(2S,4R)-1-[5-Cyano-3-(2-methoxy-phenyl)-2-oxo-1-(thiophene-3-sulfonyl)-2,3-dihydro-1H-indol-3-yl]-4-hydroxy-pyrrolidine-2-carboxylic acid dimethylamide, mixture of diastereomers

Example 343

(S)-2-{[5-Cyano-1-(4-methoxy-benzenesulfonyl)-3-(2-methoxy-pyridin-3-yl)-2-oxo-2,3-dihydro-1H-indol-3-yl]-methyl-amino}-N,N-dimethyl-propionamide, mixture of diastereomers

Example 344

(S)-2-{[5-Cyano-1-(2,4-dimethoxy-benzenesulfonyl)-3-(2-methoxy-pyridin-3-yl)-2-oxo-2,3-dihydro-1H-indol-3-yl]-methyl-amino}-N,N-dimethyl-propionamide, mixture of diastereomers

Example 345

(S)-2-[5-Chloro-1-(2,4-dimethoxy-benzenesulfonyl)-3-(2-methoxy-pyridin-3-yl)-2-oxo-2,3-dihydro-1H-indol-3-ylamino]-3,N,N-trimethyl-butyramide, levorotatory diastereomer

Example 346

(S)-1-[5-Cyano-1-(4-methoxy-benzenesulfonyl)-3-(2-methoxy-pyridin-3-yl)-2-oxo-2,3-dihydro-1H-indol-3-yl]-piperidine-2-carboxylic acid dimethylamide, levorotatory diastereomer

Example 347

(S)-1-[5-Cyano-3-(2-methoxy-pyridin-3-yl)-1-(5-methyl-pyridine-2-sulfonyl)-2-oxo-2,3-dihydro-1H-indol-3-yl]-piperidine-2-carboxylic acid dimethylamide, levorotatory diastereomer

Example 348

(2S,4R)-4-Hydroxy-1-[1-(4-methoxy-benzenesulfonyl)-3-(2-methoxy-pyridin-3-yl)-2-oxo-5-trifluoromethoxy-2,3-dihydro-1H-indol-3-yl]-pyrrolidine-2-carboxylic acid dimethylamide, levorotatory diastereomer

Example 349

(S)-1-[5-Cyano-3-(2-methoxy-pyridin-3-yl)-1-(5-methyl-pyridine-2-sulfonyl)-2-oxo-2,3-dihydro-1H-indol-3-yl]-pyrrolidine-2-carboxylic acid dimethylamide, levorotatory diastereomer

Example 350

(S)-1-[5-Chloro-3-(2-methoxy-pyridin-3-yl)-1-(5-methyl-pyridine-2-sulfonyl)-2-oxo-2,3-dihydro-1H-indol-3-yl]-pyrrolidine-2-carboxylic acid dimethylamide, levorotatory diastereomer

Example 351

2-[5-Chloro-1-(2,4-dimethoxy-benzenesulfonyl)-3-(2-methoxy-pyridin-3-yl)-2-oxo-2,3-dihydro-1H-indol-3-ylamino]-2,N,N-trimethyl-propionamide

Example 352

(2S,4R)-1-[5-Cyano-1-(2,4-dimethoxy-benzenesulfonyl)-3-(2-methoxy-pyridin-3-yl)-2-oxo-2,3-dihydro-1H-indol-3-yl]-4-fluoro-pyrrolidine-2-carboxylic acid dimethylamide, levorotatory diastereomer

Example 353

(2S,4R)-1-[5-Cyano-1-(4-methoxy-benzenesulfonyl)-3-(2-methoxy-pyridin-3-yl)-2-oxo-2,3-dihydro-1H-indol-3-yl]-4-fluoro-pyrrolidine-2-carboxylic acid dimethylamide, levorotatory diastereomer

Example 354

(2S,4R)-1-[5-Cyano-3-(2-methoxy-pyridin-3-yl)-1-(5-methyl-pyridine-2-sulfonyl)-2-oxo-2,3-dihydro-1H-indol-3-yl]-4-fluoro-pyrrolidine-2-carboxylic acid dimethylamide, levorotatory diastereomer

Example 355

(2S,4R)-1-[5-Chloro-3-(2-ethoxy-pyridin-3-yl)-1-(4-methoxy-benzenesulfonyl)-2-oxo-2,3-dihydro-1H-indol-3-yl]-4-hydroxy-pyrrolidine-2-carboxylic acid dimethylamide, mixture of diastereomers

Example 356

(S)-2-{[5-Chloro-1-(4-methoxy-benzenesulfonyl)-3-(2-methoxy-pyridin-3-yl)-2-oxo-2,3-dihydro-1H-indol-3-yl]-methyl-amino}-N,N-dimethyl-propionamide, levorotatory diastereomer

Example 357

(S)-2-{[5-Chloro-3-(2-methoxy-pyridin-3-yl)-1-(5-methyl-pyridine-2-sulfonyl)-2-oxo-2,3-dihydro-1H-indol-3-yl]-methyl-amino}-N,N-dimethyl-propionamide, levorotatory diastereomer

Example 358

(2S,4R)-1-[5-Chloro-3-(2-methoxy-pyridin-3-yl)-1-(5-methyl-pyridine-2-sulfonyl)-2-oxo-2,3-dihydro-1H-indol-3-yl]-4-fluoro-pyrrolidine-2-carboxylic acid dimethylamide, levorotatory diastereomer

Example 359

3-[(S)-2-(Azetidine-1-carbonyl)-pyrrolidin-1-yl]-5-chloro-1-(2,4-dimethoxy-benzenesulfonyl)-3-(2-methoxy-pyridin-3-yl)-1,3-dihydro-indol-2-one, levorotatory diastereomer

Example 360

(S)-1-[5-Chloro-1-(2,4-dimethoxy-benzenesulfonyl)-3-(2-methoxy-pyridin-3-yl)-2-oxo-2,3-dihydro-1H-indol-3-yl]-pyrrolidine-2-carboxylic acid ethyl-methyl-amide, levorotatory diastereomer

Example 361

(2S,4S)-1-[5-Chloro-1-(2,4-dimethoxy-benzenesulfonyl)-3-(2-methoxy-pyridin-3-yl)-2-oxo-2,3-dihydro-1H-indol-3-yl]-4-hydroxy-pyrrolidine-2-carboxylic acid dimethylamide, levorotatory diastereomer

Example 362

(2S,4S)-1-[5-Chloro-1-(2,4-dimethoxy-benzenesulfonyl)-3-(2-methoxy-pyridin-3-yl)-2-oxo-2,3-dihydro-1H-indol-3-yl]-4-methoxy-pyrrolidine-2-carboxylic acid dimethylamide, levorotatory diastereomer

Example 363

(2S,4S)-1-[5-Chloro-1-(2,4-dimethoxy-benzenesulfonyl)-3-(2-methoxy-pyridin-3-yl)-2-oxo-2,3-dihydro-1H-indol-3-yl]-4-phenoxy-pyrrolidine-2-carboxylic acid dimethylamide, levorotatory diastereomer

Example 364

(2S,4S)-1-[5-Chloro-1-(2,4-dimethoxy-benzenesulfonyl)-3-(2-methoxy-pyridin-3-yl)-2-oxo-2,3-dihydro-1H-indol-3-yl]-4-fluoro-pyrrolidine-2-carboxylic acid dimethylamide, levorotatory diastereomer

Example 365

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-methoxy-pyrrolidine-2-carboxylic acid dimethylamide, levorotatory diastereomer

Example 366

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-phenoxy-pyrrolidine-2-carboxylic acid dimethylamide, levorotatory diastereomer

Example 367

(S)-1-[5-Chloro-1-(2,4-dimethoxy-benzenesulfonyl)-3-(2-methoxy-pyridin-3-yl)-2-oxo-2,3-dihydro-1H-indol-3-yl]-4,4-difluoro-pyrrolidine-2-carboxylic acid dimethylamide, levorotatory diastereomer

Example 368

(2S,4R)-1-[5-Chloro-1-(2,4-dimethoxy-benzenesulfonyl)-3-(2-methoxy-pyridin-3-yl)-2-oxo-2,3-dihydro-1H-indol-3-yl]-4-hydroxy-piperidine-2-carboxylic acid dimethylamide, levorotatory diastereomer

Example 369

(2S,4S)-1-[5-Chloro-1-(2,4-dimethoxy-benzenesulfonyl)-3-(2-methoxy-pyridin-3-yl)-2-oxo-2,3-dihydro-1H-indol-3-yl]-4-fluoro-piperidine-2-carboxylic acid dimethylamide, levorotatory diastereomer

Example 370

(S)-1-[5-Chloro-1-(2,4-dimethoxy-benzenesulfonyl)-3-(2-methoxy-pyridin-3-yl)-2-oxo-2,3-dihydro-1H-indol-3-yl]-4,4-difluoro-piperidine-2-carboxylic acid dimethylamide, levorotatory diastereomer In the following Table 2 characteristic mass-spectroscopic data are shown for selected examples.

TABLE 2

Characteristic mass-spectroscopic data for selected examples (ESI, positive mode)

| Example # | Molecular ion peak |
|---|---|
| 1 | 657 |
| 2 | 657 |
| 3 | 662 |
| 4 | 662 |
| 5 | 631 |
| 6 | 631 |
| 9 | 631 |
| 10 | 631 |
| 13 | 632 |
| 28 | 621 |
| 29 | 576 |
| 30 | 576 |
| 31 | 610 |
| 32 | 690 |
| 33 | 690 |
| 35 | 646 |
| 37 | 626 |
| 38 | 674 |
| 39 | 574 |
| 40 | 588 |
| 41 | 622 |
| 42 | 602 |
| 43 | 650 |
| 44 | 589 |
| 45 | 605 |
| 46 | 650 |
| 47 | 571 |
| 48 | 649 |
| 53 | 663 |
| 54 | 599 |
| 55 | 571 |
| 56 | 656 |

TABLE 2-continued

Characteristic mass-spectroscopic data for selected examples
(ESI, positive mode)

| Example # | Molecular ion peak |
|---|---|
| 57 | 663 |
| 59 | 684 |
| 60 | 641 |
| 61 | 625 |
| 62 | 480 |
| 63 | 633 |
| 64 | 481 |
| 65 | 592 |
| 66 | 670 |
| 68 | 711 |
| 70 | 702 |
| 75 | 690 |

The invention claimed is:

1. A compound of the formula (II) or a pharmaceutically acceptable salt thereof

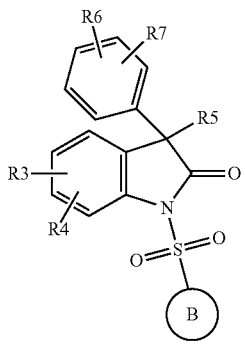

(II)

in which
B is selected from the group consisting of thiophene, furan, pyrrole, pyridine, quinoline, tetrahydroquinoline, isoquinoline, tetrahydroisoquinoline, benzothiophene, benzofuran, dihydrobenzofuran, indole,
an aromatic heteromonocyclic and an aromatic or partially aromatic heterobicyclic ring,
where the heterocycles are 5- or 6-membered rings and comprise 2 to 4 heteroatoms selected from the group consisting of N, O and S, and up to 2 oxo groups, and
B may be substituted by the radicals $R^{21}$, $R^{22}$ and/or $R^{23}$,
$R^{21}$, $R^{22}$ and $R^{23}$ at each occurrence are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl), N($C_1$-$C_4$-alkyl)$_2$, morpholin-4-yl, pyrrolidin-1-yl, piperidin-1-yl, 4-piperazin-1-yl, and 4-($C_1$-$C_4$-alkyl)-piperazin-1-yl,
$R^3$ and $R^4$ are selected independently of one another from the group consisting of hydrogen, chlorine, bromine, iodine, fluorine, CN, $CF_3$, $OCF_3$, $NO_2$, OH, O—$C_1$-$C_4$-alkyl, O-phenyl, O—$C_1$-$C_4$-alkylen-phenyl, phenyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$, or
$R^3$ and $R^4$ are connected to give —CH=CH—CH=CH—, —(CH$_2$)$_4$— or —(CH$_2$)$_3$—,
$R^5$ is a radical (W)—(X)—(Y)—Z,
where
W is selected from the group consisting of $C_1$-$C_4$-alkylen, $C_2$-$C_4$-alkenylen, $C_2$-$C_4$-alkynylen, O, O—($C_1$-$C_4$-alkylen), S, S—($C_1$-$C_4$-alkylen), $NR^{54}$, $NR^{54}$—($C_1$-$C_4$-alkylen) and a bond,
X is selected from the group consisting of CO, CO—O, $SO_2$, $NR^{54}$, $NR^{54}$—CO, $NR^{54}$—$SO_2$, CO—$NR^{58}$ and a bond,
Y is $C_1$-$C_6$-alkylen, $C_2$-$C_6$-alkenylen, $C_2$-$C_6$-alkynylen, or a bond,
Z is selected from the group consisting of hydrogen, E, O—$R^{52}$, $NR^{51}R^{52}$, and S—$R^{52}$,
where
E is an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, said ring may comprise up to two oxo groups, and may be substituted by radicals $R^{55}$, $R^{56}$, $R^{57}$ and/or up to three radicals $R^{53}$,
$R^{54}$ at each occurrence is independently selected from the group consisting of hydrogen, $C_1$-$C_6$-alkyl, $C_2$-$C_6$-alkenyl, $C_2$-$C_6$alkynyl, phenyl and $C_1$-$C_4$-alkylen-phenyl, where the phenyl ring may be substituted by up to two radicals $R^{53}$,
$R^{52}$ at each occurrence is independently selected from the group consisting of hydrogen, $C_1$-$C_6$-alkyl, $C_2$-$C_6$-alkenyl, $C_2$-$C_6$alkynyl, E and $C_1$-$C_4$-alkylen-E,
$R^{53}$ at each occurrence is independently selected from the group consisting of hydrogen, chlorine, bromine, iodine, fluorine, CN, $CF_3$, $OCF_3$, $NO_2$, OH, O—$C_1$-$C_4$-alkyl, $C_1$-$C_6$-alkyl, $C_2$-$C_6$-alkenyl, $C_2$-$C_6$-alkynyl, $NH_2$, NH($C_1$-$C_4$-alkyl) and N($C_1$-$C_4$-alkyl)$_2$,
$R^{54}$ at each occurrence is independently selected from the group consisting of hydrogen, $C_1$-$C_6$-alkyl, $C_2$-$C_6$-alkenyl, $C_2$-$C_6$-alkynyl, phenyl and $C_1$-$C_4$-alkylen-phenyl, where the phenyl ring may be substituted by up to two radicals $R^{59}$,
$R^{55}$ at each occurrence is independently selected from the group consisting of hydrogen, $C_1$-$C_6$-alkyl, $C_2$-$C_6$-alkenyl, $C_2$-$C_6$-alkynyl, phenyl, $C_1$-$C_4$-alkylen-phenyl, where the ring may be substituted by up to two radicals $R^{60}$, OH, O—$C_1$-$C_4$-alkyl, O-phenyl, O—$C_1$-$C_4$-alkylen-phenyl, $NH_2$, NH($C_1$-$C_4$-alkyl) and N($C_1$-$C_4$-alkyl)$_2$,
$R^{56}$ is a group $Q^1$-$Q^2$-$Q^3$, where
$Q^1$ is selected from the group consisting of a bond, $C_1$-$C_4$-alkylen, $C_2$-$C_4$-alkenylen, $C_2$-$C_4$-alkynylen, $C_1$-$C_4$-alkylen-N($C_1$-$C_4$-alkyl), N($C_1$-$C_4$-alkyl), $C_1$-$C_4$-alkylen-NH, NH, N($C_1$-$C_4$-alkyl)-$C_1$-$C_4$-alkylen, NH—$C_1$-$C_4$-alkylen, $C_1$-$C_4$-alkylen-O, O—$C_1$-$C_4$-alkylen, CO—NH, CO—N($C_1$-$C_4$-alkyl), NH—CO, N($C_1$-$C_4$-alkyl)-CO, CO, $SO_2$, SO, S, O, $SO_2$—NH, $SO_2$—N($C_1$-$C_4$-alkyl), NH—$SO_2$, N($C_1$-$C_4$-alkyl)-$SO_2$, O—CO—NH, O—CO—N($C_1$-$C_4$-alkyl), NH—CO—O, N($C_1$-$C_4$-alkyl)-CO—O, N($C_1$-$C_4$-alkyl)-CO—N($C_1$-$C_4$-alkyl), NH—CO—N($C_1$-$C_4$-alkyl), N($C_1$-$C_4$-alkyl)-CO—NH, and NH—CO—NH,
$Q^2$ is selected from the group consisting of $C_1$-$C_4$-alkylen, $C_2$-$C_4$-alkenylen, $C_2$-$C_4$-alkynylen, and a bond,
$Q^3$ is a hydrogen or an unsaturated, saturated or partially unsaturated mono-, bi- or tricyclic ring having a maximum of 14 carbon atoms and 0 to 5 nitrogen atoms, 0 to 2 oxygen atoms and/or 0 to 2 sulfur atoms, which may comprise up to two oxo groups and may be substituted by the radicals $R^{63}$, $R^{64}$ and/or $R^{65}$,
$R^{57}$ at each occurrence is independently selected from the group consisting of hydrogen, $C_1$-$C_6$-alkyl, phenyl, $C_1$-$C_4$-alkylen-phenyl, COOH, CO—O—$C_1$-$C_4$-alkyl, $CONH_2$, CO—NH—$C_1$-$C_4$-alkyl, CO—N($C_1$-$C_4$- alkyl)$_2$, CO—C$_1$-C$_4$-alkyl, CH$_2$—NH$_2$, CH$_2$—NH—C$_1$-C$_4$-alkyl and CH$_2$—N(C$_1$-C$_4$-alkyl)$_2$, R$^{58}$ at each occurrence is independently selected from the group consisting of hydrogen, C$_1$-C$_6$-alkyl, C$_2$-C$_6$-alkenyl, C$_2$-C$_6$-alkynyl, phenyl and C$_1$-C$_4$-alkylen-phenyl, where the phenyl ring may be substituted by up to two radicals R$^{62}$, R$^{59}$, R$^{60}$ and R$^{62}$ at each occurrence are selected independently of one another from the group consisting of hydrogen, chlorine, bromine, iodine, fluorine, CN, CF$_3$, OCF$_3$, NO$_2$, OH, O—C$_1$-C$_4$-alkyl, C$_1$-C$_6$-alkyl, C$_2$-C$_6$-alkenyl, C$_2$-C$_6$-alkynyl, NH$_2$, NH(C$_1$-C$_4$-alkyl) and N(C$_1$-C$_4$-alkyl)$_2$, R$^{63}$, R$^{64}$ and R$^{65}$ at each occurrence are selected independently of one another from the group consisting of hydrogen, chlorine, bromine, iodine, fluorine, CN, CF$_3$, OCF$_3$, NO$_2$, OH, O—C$_1$-C$_4$-alkyl, O-phenyl, O—C$_1$-C$_4$-alkylen-phenyl, phenyl, C$_1$-C$_6$-alkyl, C$_2$-C$_6$-alkenyl, C$_2$-C$_6$-alkynyl, NH$_2$, NH(C$_1$-C$_4$-alkyl) and N(C$_1$-C$_4$-alkyl)$_2$, and R$^6$ and R$^7$ at each occurrence are selected independently of one another from the group consisting of hydrogen, chlorine, bromine, iodine, fluorine, CN, CF$_3$, OCF$_3$, NO$_2$, OH, O—C$_1$-C$_4$-alkyl, O-phenyl, O—C$_1$-C$_4$-alkylen-phenyl, phenyl, C$_1$-C$_6$-alkyl, C$_2$-C$_6$-alkenyl, C$_2$-C$_6$-alkynyl, NH$_2$, NH(C$_4$-C$_4$-alkyl) and N(C$_4$-C$_4$-alkyl)$_2$.

2. The compound of claim 1, wherein B is selected from the group consisting of thiophene, furan, pyrrole, pyrazole, isoxazole, pyridine, pyrimidine, quinoline, isoquinoline, tetrahydroisoquinoline, benzothiophene, benzofuran, indole, imidazole, thiazole, imidazothiazole, benzooxazine and quinoxaline.

3. A pharmaceutical composition comprising a compound as claimed in claim 1 and a pharmaceutically acceptable carrier.

4. A method for the treatment of depressive and/or bipolar disorders, comprising administering to a mammal a therapeutically effective amount of a compound of claim 1, or a pharmaceutically acceptable salt thereof.

5. A method for the treatment of anxiety and/or stress-related disorders, comprising administering to a mammal a therapeutically effective amount of a compound of claim 1, or a pharmaceutically acceptable salt thereof.

6. The method of claim 4, wherein the disorder is selected from the group consisting of a dysthymic disorder, subsyndromal depression, a seasonal affective disorder, a premenstrual dysphoric disorder, and a psychotic disorder.

7. The method of claim 5, wherein the disorder is selected from the group consisting of a general anxiety disorder, a panic disorder, an obsessive-compulsive disorder, a post-traumatic disorder, an acute stress disorder, and a social phobia.

8. A compound of claim 1 or a pharmaceutically acceptable salt thereof, selected from the group consisting of
(2S,4R)-1-[5-Chloro-3-(2-methoxy-phenyl)-2-oxo-1-(quinoline-8-sulfonyl)-2,3-dihydro-1H-indol-3-yl]-4-hydroxy-pyrrolidine-2-carboxylic acid dimethylamide;
(2S,4R)-1-[5-Chloro-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethylamide;
(2S,4R)-1-[5-Chloro-3-(2-methoxy-phenyl)-2-oxo-1-(thiophene-3-sulfonyl)-2,3-dihydro-1H-indol-3-yl]-4-hydroxy-pyrrolidine-2-carboxylic acid dimethylamide trifluoroacetate;
(2S,4R)-1-[5-Chloro-1-(5-chloro-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[1-(3-Bromo-5-chloro-thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide
(2S,4R)-1-[1-(4-Bromo-5-chloro-thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-1-(5-methyl-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(4,5-dichloro-thiophene-2-sulfonyl)-3-(2-methoxy-phenyl)-2-oxo-2,3-dihydro-1H-indol-3-yl]-4-hydroxy-pyrrolidine-2-carboxylic acid dimethylamide trifluorocetate;
(2S,4R)-1-[5-Chloro-1-(3-methylbenzo[b]thiophene-2-sulfonyl)-3-(2-methoxyphenyl)-2-oxo-2,3-dihydro-1H-indol-3-yl]-4-hydroxy-pyrrolidine-2-carboxylic acid dimethylamide;
(2S,4R)-1-[1-(Benzo[b]thiophene-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(5-chloro-3-methyl-benzo[b]thiophene-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(1-methyl-1H-imidazole-4-sulfonyl)-2-oxo-2,3-dihydro-1H-indol-3-yl]-4-hydroxy-pyrrolidine-2-carboxylic acid dimethylamide;
(2S,4R)-1-[5-Chloro-1-(1,2-dimethyl-1H-imidazole-4-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(5-chloro-1,3-dimethyl-1H-pyrazole-4-sulfonyl)-3-(2-methoxy-phenyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-3-(2-methoxy-phenyl)-2-oxo-1-(1,3,5-trimethyl-1H-pyrazole-4-sulfonyl)-2,3-dihydro-1H-indol-3-yl]-4-hydroxy-pyrrolidine-2-carboxylic acid dimethylamide trifluoroacetate;
(2S,4R)-1-[5-Chloro-3-(2-methoxy-phenyl)-1-(5-methyl-1-phenyl-1H-pyrazole-4-sulfonyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-1-(3,5-dimethyl-isoxazole-4-sulfonyl)-3-(2-methoxy-phenyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-1-(2,4-dimethyl-thiazole-5-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(6-chloro-imidazo[2,1-b]thiazole-5-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-2-oxo-1-(pyridine-2-sulfonyl)-2,3-dihydro-1H-indol-3-yl]-4-hydroxy-pyrrolidine-2-carboxylic acid dimethylamide;

(2S,4R)-1-[1-(5-Bromo-pyridine-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(5-trifluoro-methyl-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(5-methoxy-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide;
(2S,4R)-1-[5-Chloro-1-(5-chloro-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[1-(5-Bromo-3-methyl-pyridine-2-sulfonyl)-5-chloro-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-1-(3,5-dimethyl-pyridine-2-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-2-oxo-1-(pyridine-3-sulfonyl)-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(6-morpholin-4-yl-pyridine-3-sulfonyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-2-oxo-1-(6-phenoxy-pyridine-3-sulfonyl)-2,3-dihydro-1H-indol-3-yl]-4-hydroxy-pyrrolidine-2-carboxylic acid dimethylamide trifluoroacetate;
(2S,4R)-1-[5-Chloro-1-(6-methoxypyridine-3-sulfonyl)-3-(2-methoxyphenyl)-2-oxo-2,3-dihydro-1H-indol-3-yl]-4-hydroxy-pyrrolidine-2-carboxylic acid dimethylamide;
(2S,4R)-1-[5-Chloro-1-(5-bromo-6-chloropyridine-3-sulfonyl)-3-(2-methoxy-phenyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(4-methyl-3,4-dihydro-2H-benzo[1,4]oxazine-7-sulfonyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-3-(2-methoxy-phenyl)-2-oxo-1-(1,2,3,4-tetrahydro-isoquinoline-7-sulfonyl)-2,3-dihydro-1H-indol-3-yl]-4-hydroxy-pyrrolidine-2-carboxylic acid dimethylamide;
N-[5-Chloro-3-(2-methoxy-phenyl)-2-oxo-1-(quinoline-8-sulfonyl)-2,3-dihydro-1H-indol-3-yl]-acetamide;
3,4,5,6-Tetrahydro-2H-[1,4]bipyridinyl-4-carboxylic acid [5-chloro-3-(2-methoxy-phenyl)-2-oxo-1-(quinoline-8-sulfonyl)-2,3-dihydro-1H-indol-3-yl]-amide;
(E)-N-[5-Chloro-3-(2-methoxy-phenyl)-2-oxo-1-(quinoline-8-sulfonyl)-2,3-dihydro-1H-indol-3-yl]-3-pyridin-4-yl-acrylamide;
(E)-N-[3-(2-Methoxy-phenyl)-2-oxo-1-(thiophene-2-sulfonyl)-2,3-dihydro-1H-indol-3-yl]-3-pyridin-4-yl-acrylamide;
4-(1-Methyl-piperidin-4-yl)-piperazine-1-carboxylic acid [3-(2-ethoxy-phenyl)-5-methoxy-2-oxo-1-(quinoline-8-sulfonyl)-2,3-dihydro-1H-indol-3-yl]-amide;
4-(1-Methyl-piperidin-4-yl)-piperazine-1-carboxylic acid [3-(2-ethoxy-phenyl)-5-methoxy-1-(3-methoxy-thiophene-2-sulfonyl)-2-oxo-2,3-dihydro-1H-indol-3-yl]-amide;
4-(1-Methyl-piperidin-4-yl)-piperazine-1-carboxylic acid [3-(2-methoxy-phenyl)-5-methyl-2-oxo-1-(thiophene-2-sulfonyl)-2,3-dihydro-1H-indol-3-yl]-amide dihydrochloride;
4-(1-Methyl-piperidin-4-yl)-piperazine-1-carboxylic acid [3-(2-ethoxy-phenyl)-5-methoxy-2-oxo-1-(thiophene-2-sulfonyl)-2,3-dihydro-1H-indol-3-yl]-amide;
4-(1-Methyl-piperidin-4-yl)-piperazine-1-carboxylic acid [5-chloro-3-(2-ethoxy-phenyl)-2-oxo-1-thiophene-2-sulfonyl)-2,3-dihydro-1H-indol-3-yl]-amide;
4-(1-Methyl-piperidin-4-yl)-piperazine-1-carboxylic acid [5-chloro-3-(2-ethoxy-phenyl)-2-oxo-1-(pyridine-2-sulfonyl)-2,3-dihydro-1H-indol-3-yl]-amide dihydrochloride;
4-(1-Methyl-piperidin-4-yl)-piperazine-1-carboxylic acid [5-chloro-3-(2-ethoxy-phenyl)-2-oxo-1-thiophene-3-sulfonyl)-2,3-dihydro-1H-indol-3-yl]-amide;
4-(1-Methyl-piperidin-4-yl)-piperazine-1-carboxylic acid [5-chloro-3-(2-ethoxy-phenyl)-1-(5-methyl-pyridine-2-sulfonyl)-2-oxo-2,3-dihydro-1H-indol-3-yl]-amide;
4-(1-Methyl-piperidin-4-yl)-piperazine-1-carboxylic acid [5-chloro-3-(2-ethoxy-phenyl)-2-oxo-1-quinoline-8-sulfonyl)-2,3-dihydro-1H-indol-3-yl]-amide;
4-(1-Methyl-piperidin-4-yl)-piperazine-1-carboxylic acid [1-(3,5-dimethyl-isoxazole-4-sulfonyl)-3-(2-ethoxy-phenyl)-5-methoxy-2-oxo-2,3-dihydro-1H-indol-3-yl]-amide;
4-(1-Methyl-piperidin-4-yl)-piperazine-1-carboxylic acid [1-(5-chloro-thiophene-2-sulfonyl)-3-(2-ethoxy-phenyl)-5-methoxy-2-oxo-2,3-dihydro-1H-indol-3-yl]-amide;
4-(1-Methyl-piperidin-4-yl)-piperazine-1-carboxylic acid [1-(2,5-dimethyl-thiophene-3-sulfonyl)-3-(2-ethoxy-phenyl)-5-methoxy-2-oxo-2,3-dihydro-1H-indol-3-yl]-amide;
4-(1-Methyl-piperidin-4-yl)-piperazine-1-carboxylic acid [5-cyano-3-(2-ethoxy-phenyl)-2-oxo-1-(thiophene-3-sulfonyl)-2,3-dihydro-1H-indol-3-yl]-amide dihydrochloride;
(2S,4R)-1-[1-(Benzo[b]thiophene-3-sulfonyl)-5-chloro-3-(2-methoxy-phenyl)-2-oxo-2,3-dihydro-1H-indol-3-yl]-4-hydroxy-pyrrolidine-2-carboxylic acid dimethylamide trifluoroacetate;
(2S,4R)-1-[5-Chloro-3-(2-methoxy-phenyl)-1-(2-methyl-1,2,3,4-tetrahydro-isoquinoline-7-sulfonyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(4-methyl-pyridine-2-sulfonyl)-2-oxo-2,3-dihydro-1H-indol-3-yl]-4-hydroxy-pyrrolidine-2-carboxylic acid dimethylamide;
(2S,4R)-1-[5-Chloro-3-(2-methoxy-phenyl)-1-(6-methyl-pyridine-2-sulfonyl)-2-oxo-2,3-dihydro-1H-indol-3-yl]-4-hydroxy-pyrrolidine-2-carboxylic acid dimethylamide;
(2S,4R)-1-[5-Fluoro-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethylamide;

(2S,4R)-1-[5-Chloro-3-(2-methoxy-phenyl)-1-(3-methoxy-thiophene-2-sulfonyl)-2-oxo-2,3-dihydro-1H-indol-3-yl]-4-hydroxy-pyrrolidine-2-carboxylic acid dimethylamide;

1-[5-Cyano-3-(2-methoxy-phenyl)-2-oxo-1-(thiophene-2-sulfonyl)-2,3-dihydro-1H-indol-3-yl]-pyrrolidine-2-carboxylic acid dimethylamide;

(2S,4R)-1-[5-Chloro-3-(2-ethoxy-phenyl)-2-oxo-1-(thiophene-2-sulfonyl)-2,3-dihydro-1H-indol-3-yl]-4-hydroxy-pyrrolidine-2-carboxylic acid dimethylamide;

(2S,4R)-1-[5-Chloro-3-(2-ethoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide;

(2S,4R)-1-[5-Cyano-3-(2-methoxy-phenyl)-2-oxo-1-(thiophene-2-sulfonyl)-2,3-dihydro-1H-indol-3-yl]-4-hydroxy-pyrrolidine-2-carboxylic acid dimethylamide;

(2S,4R)-1-[5-Cyano-3-(2-methoxy-phenyl)-1-(5-methyl-pyridine-2-sulfonyl)-2-oxo-2,3-dihydro-1H-indol-3-yl]-4-hydroxy-pyrrolidine-2-carboxylic acid dimethylamide;

(2S,4R)-1-[3-(2-Ethoxy-phenyl)-5-methoxy-1-(5-methyl-pyridine-2-sulfonyl)-2-oxo-2,3-dihydro-1H-indol-3-yl]-4-hydroxy-pyrrolidine-2-carboxylic acid dimethylamide; and (2S,4R)-1-[5-Cyano-3-(2-methoxy-phenyl)-2-oxo-1-(thiophene-3-sulfonyl)-2,3-dihydro-1H-indol-3-yl]-4-hydroxy-pyrrolidine-2-carboxylic acid dimethylamide.

* * * * *